US012622976B2

(12) United States Patent
James

(10) Patent No.: US 12,622,976 B2
(45) **Date of Patent: *May 12, 2026**

(54) TARGETING CLPTM1L FOR TREATMENT AND PREVENTION OF CANCER

(71) Applicant: The Medical College of Wisconsin, Inc., Milwaukee, WI (US)

(72) Inventor: Michael A. James, Big Bend, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/903,213

(22) Filed: Oct. 1, 2024

(65) Prior Publication Data

US 2025/0090876 A1 Mar. 20, 2025

Related U.S. Application Data

(63) Continuation of application No. 17/286,748, filed as application No. PCT/US2019/056251 on Oct. 15, 2019, now Pat. No. 12,129,305.

(60) Provisional application No. 62/750,450, filed on Oct. 25, 2018.

(51) Int. Cl.
| | |
|---|---|
| *A61P 35/00* | (2006.01) |
| *A61K 47/68* | (2017.01) |
| *C07K 16/30* | (2006.01) |
| *A61K 39/00* | (2006.01) |

(52) U.S. Cl.
CPC ...... *A61K 47/6851* (2017.08); *A61K 47/6803* (2017.08); *A61K 47/68033* (2023.08); *A61P 35/00* (2018.01); *C07K 16/30* (2013.01); *A61K 2039/505* (2013.01); *C07K 2317/21* (2013.01); *C07K 2317/52* (2013.01); *C07K 2317/622* (2013.01)

(58) Field of Classification Search
CPC ............... A61P 35/00; A61K 47/6803; A61K 47/68033; A61K 47/6851; A61K 2039/505; C07K 16/30; C07K 2317/52; C07K 2317/622; C07K 2317/34; C07K 2317/73; C07K 2317/76
USPC .................................................... 424/174.1
See application file for complete search history.

(56) References Cited

U.S. PATENT DOCUMENTS

| | | | |
|---|---|---|---|
| 4,444,887 A | 4/1984 | Hoffmann | |
| 4,716,111 A | 12/1987 | Osband et al. | |
| 4,816,567 A | 3/1989 | Cabilly et al. | |
| 5,225,539 A | 7/1993 | Winter | |
| 5,229,275 A | 7/1993 | Goroff | |
| 5,413,923 A | 5/1995 | Kucherlapati et al. | |
| 5,530,101 A | 6/1996 | Queen et al. | |
| 5,545,806 A | 8/1996 | Lonberg et al. | |
| 5,545,807 A | 8/1996 | Surani et al. | |
| 5,565,332 A | 10/1996 | Hoogenbloom et al. | |
| 5,567,610 A | 10/1996 | Borrebaeck et al. | |
| 5,569,825 A | 10/1996 | Lonberg et al. | |
| 5,585,089 A | 12/1996 | Queen et al. | |
| 5,591,669 A | 1/1997 | Krimpenfort et al. | |
| 5,625,126 A | 4/1997 | Longberg et al. | |
| 5,633,425 A | 5/1997 | Longberg et al. | |
| 5,639,641 A | 6/1997 | Pedersen et al. | |
| 5,661,016 A | 8/1997 | Longberg et al. | |
| 5,693,761 A | 12/1997 | Queen et al. | |
| 5,693,762 A | 12/1997 | Queen et al. | |
| 5,775,745 A | 7/1998 | Hoppe et al. | |
| 5,814,318 A | 9/1998 | Longberg et al. | |
| 5,821,337 A | 10/1998 | Carter et al. | |
| 5,837,234 A | 11/1998 | Gentile et al. | |
| 5,869,046 A | 2/1999 | Presta et al. | |

(Continued)

FOREIGN PATENT DOCUMENTS

| | | |
|---|---|---|
| EP | 0239400 A2 | 9/1987 |
| EP | 0519596 A1 | 12/1992 |

(Continued)

OTHER PUBLICATIONS

"Guidance for Industry: For the Submission of Chemistry, Manufacturing and Controls and Establishment Description Information for Human Blood and Blood Components Intended for Transfusion or for Further Manufacture and for the Completion of the Form FDA 356h, 'Application to Market a New Drug, Biologic or an Antibiotic Drug for Human Use;'" availability. Food and Drug Administration, HHS. Notice. Fed Regist. 1999;64(89):25049-50.

(Continued)

*Primary Examiner* — Yan Xiao

(74) *Attorney, Agent, or Firm* — Quarles & Brady LLP

(57) ABSTRACT

Provided herein are therapeutic agents having specificity for human CLPTM1L/CRR9 polypeptide, including therapeutic agents comprising one or more CLPTM1L-targeting agents, compositions comprising such therapeutic agents, and methods of using such compositions for treating or preventing a cancer, pre-cancerous lesion, or other disease condition associated with CLPTM1L/CRR9 protein dysfunction (e.g., pathogenic production, modification, or function). In particular, provided herein are fully human monoclonal antibodies against human CLPTM1L/CRR9 protein and methods of using such antibodies for treating or preventing a cancer, pre-cancerous lesion, or other disease condition associated with CLPTM1L/CRR9 protein dysfunction (e.g., pathogenic production, modification, or function).

10 Claims, 39 Drawing Sheets

Specification includes a Sequence Listing.

(56) References Cited

U.S. PATENT DOCUMENTS

| | | | |
|---|---|---|---|
| 5,885,793 | A | 3/1999 | Griffiths et al. |
| 5,916,771 | A | 6/1999 | Hori et al. |
| 5,922,845 | A | 7/1999 | Deo et al. |
| 5,929,212 | A | 7/1999 | Jolliffe et al. |
| 5,939,598 | A | 8/1999 | Kucherlapati et al. |
| 5,969,108 | A | 10/1999 | McCafferty et al. |
| 6,013,605 | A | 1/2000 | Rees et al. |
| 6,114,598 | A | 9/2000 | Kucherlapati et al. |
| 6,180,370 | B1 | 1/2001 | Queen et al. |
| 6,193,966 | B1 | 2/2001 | Deo et al. |
| 6,207,418 | B1 | 3/2001 | Hori et al. |
| 6,235,883 | B1 | 5/2001 | Jakobovits et al. |
| 6,300,064 | B1 | 10/2001 | Knappik et al. |
| 6,303,755 | B1 | 10/2001 | Deo et al. |
| 6,824,780 | B1 | 11/2004 | Devaux et al. |
| 7,064,244 | B2 | 6/2006 | Jakobovits et al. |
| 7,119,172 | B2 | 10/2006 | Pier et al. |
| 7,227,002 | B1 | 6/2007 | Kufer et al. |
| 7,241,877 | B2 | 7/2007 | Adair et al. |
| 7,244,615 | B2 | 7/2007 | Adair et al. |
| 7,244,832 | B2 | 7/2007 | Adair et al. |
| 7,262,050 | B2 | 8/2007 | Adair et al. |
| 7,635,666 | B1 | 12/2009 | McCafferty et al. |
| 7,723,270 | B1 | 5/2010 | McCafferty et al. |
| 7,820,877 | B2 | 10/2010 | Jakobovits et al. |
| 8,809,051 | B2 | 8/2014 | Jakobovits et al. |
| 9,156,913 | B2 | 10/2015 | Freimoser-Grundschober et al. |
| 10,266,586 | B2 | 4/2019 | James |
| 10,358,492 | B2 | 7/2019 | Bakker et al. |
| 10,829,548 | B2 | 11/2020 | James |
| 12,129,305 | B2 * | 10/2024 | James ............ A61K 47/68033 |
| 2006/0235206 | A1 | 10/2006 | Pier et al. |
| 2009/0149637 | A1 | 6/2009 | Kucherlapati et al. |
| 2012/0117669 | A1 | 5/2012 | Kucherlapati et al. |
| 2013/0117871 | A1 | 5/2013 | Kucherlapati et al. |
| 2014/0065152 | A1 | 3/2014 | Kwon |
| 2015/0353956 | A1 | 12/2015 | Schultheiss et al. |
| 2016/0264651 | A1 | 9/2016 | Freimoser-Grundschober et al. |
| 2017/0275362 | A1 | 9/2017 | Brentjens et al. |
| 2019/0352393 | A1 | 11/2019 | Bakker et al. |

FOREIGN PATENT DOCUMENTS

| | | | |
|---|---|---|---|
| WO | 96/16673 | A1 | 6/1996 |
| WO | 96/34096 | A1 | 10/1996 |

OTHER PUBLICATIONS

Jia J, Bosley AD, Thompson A, Hoskins JW, Cheuk A, Collins I, et al. CLPTM1L promotes growth and enhances aneuploidy in pancreatic cancer cells, Cancer Res., May 15, 2014; 74(10): 2785-2795.

Lee HW, Park WJ, Heo YR, Park TI, Park SY, Lee Jh. TERT-CLPTM1 locus polymorphism (rs401681) is associated with the prognosis of hepatocellular carcinoma. Onco Targets Ther. 2017;10:4853-8.

Li X, Wang X. The emerging roles and therapeutic potential of exosomes in epithelial ovarian cancer. Mol Cancer. 2017;16(1):92.

Mobuchon L, Battistella A, Bardel C, Scelo G, Renoud A, Houy A, et al. A GWAS in uveal melanoma identifies risk polymorphisms in the CLPTM1L locus. NPJ Genom Med. 2017;2.

Ni Z, Tao K, Chen G, Chen Q, Tang J, Luo X, et al. CLPTM1L is overexpressed in lung cancer and associated with apoptosis. PLoS One. 2012;7(12):e52598.

Patel GK, Khan MA, Bhardwaj A, Srivastava SK, Zubair H, Patton MC, et al. Exosomes confer chemoresistance to pancreatic cancer cells by promoting ROS detoxification and miR-155-mediated suppression of key gemcitabine-metabolising enzyme, DCK. Br J Cancer. 2017;116(5):609-19.

Puskas LG, Man I, Szebeni G, Tiszlavicz L, Tsai S, James MA. Novel Anti-CRR9/CLPTM1L Antibodies with Antitumorigenic Activity Inhibit Cell Surface Accumulation, PI3K Interaction, and Survival Signaling, Mol Cancer Ther., May 2016; 15(5):985-997.

Qiu J, Yang G, Feng M, Zheng S, Cao Z, You L, et al. Extracellular vesicles as mediators of the progression and chemoresistance of pancreatic cancer and their potential clinical applications. Mol Cancer. 2018;17(1):2.

Santos JC, Lima NDS, Sarian LO, Matheu A, Ribeiro ML, Derchain SFM. Exosome-mediated breast cancer chemoresistance via miR-155 transfer. Sci Rep. 2018;8(1):829.

Thakur PC, Miller-Ocuin JL, Nguyen K, Matsuda R, Singhi AD, Zeh HJ, et al. Inhibition of endoplasmic-reticulum-stress-mediated autophagy enhances the effectiveness of chemotherapeutics on pancreatic cancer. J Transl Med. 2018;16(1):190.

Trezise S, Karnowski A, Fedele PL, Mithraprabhu S, Liao Y, D'Costa K, et al. Mining the Plasma Cell Transcriptome for Novel Cell Surface Proteins. Int J Mol Sci. 2018;19(8).

Wang L, Zhang Y, Wang W, Zhu Y, Chen Y, Tian B. Gemcitabine treatment induces endoplasmic reticular (ER) stress and subsequently upregulates urokinase plasminogen activator (uPA) to block mitochondrial-dependent apoptosis in Panc-1 cancer stem-like cells (CSCs). PLoS One. 2017;12(8):e0184110.

Yamamoto K, Okamoto A, Isonishi S, Ochiai K, Ohtake Y. A novel gene, CRR9, which was up-regulated in CDDP-resistant ovarian tumor cell line, was associated with apoptosis. Biochem Biophys Res Commun. 2001;280(4):1148-54.

Yoshiura K, Machida J, Daack-Hirsch S, Patil SR, Ashworth LK, Hecht JT, et al. Characterization of a novel gene disrupted by a balanced chromosomal translocation t(2; 19)(q11.2;q13.3) in a family with cleft lip and palate. Genomics. 1998;54(2):231-40.

Zhang HD, Jiang LH, Hou JC, Zhong SL, Zhu LP, Wang DD, et al. Exosome: a novel mediator in drug resistance of cancer cells, Epigenomics, 2018, 10(11), 1499-1509.

Zhang R, Chen X, Zhang S, Zhang X, Li T, Liu Z, et al. Upregulation of miR-494 Inhibits Cell Growth and Invasion and Induces Cell Apoptosis by Targeting Cleft Lip and Palate Transmembrane 1-Like in Esophageal Squamous Cell Carcinoma. Dig Dis Sci. 2015;60(5):1247-55.

Sharma, A., Nanomedicine (Lond.), 2017, 12(17), 2137-2148.

Byers, T. (CA Cancer Journal, 1999, 49: 353-361).

Gura (Science, 1997; 278: 1041-1042).

Dennis (Nature, Aug. 7, 2006; 442: 739-741).

Reagan-Shaw et al. (FASEB J, 2007, 22: 659-61).

Omasists et al., Bioinformatics, 30(6): 884-6, 2014.

Chothia & Lesk, J. Mol. Biol., 196: 901-917 (1987).

Chothia et al., Nature 342:878-883 (1989).

Skerra & Pluckthun, Science 240:1038-41 (1988).

Bird et al., Science 242:423-26 (1988).

Huston et al., Proc. Natl. Acad. Sci. USA 85:5879-83 (1988).

Jakobovits et al., Proc. Natl. Acad. Sci. USA, 90:2551 (1993).

Jakobovits et al., Nature, 362:255-258 (1993).

Bruggemann et al., Year in Immuno., 7:33 (1993).

Scatchard et al., Ann. N.Y. Acad. Sci. USA, 51:660 (1949).

Lonberg and Huszar, Int. Rev. Immunol., 13:65-93 (1995).

Smaglo et al., Nat. Rev. Clin. Oncol, 11:637-48 (2014).

Padlan, Mol. Immunol., 28:489-498 (1991).

Studnicka et al., Prot. Eng. 7:805-814 (1994).

Roguska et al., Proc. Natl. Acad. Sci. 91:969-973 (1994).

Millstein et al., Nature, 305:537-539 (1983).

Vincent and Zurini, Biotechnol. J. 7(12):1444-50 (2012).

Kaneko and Niwa, Biodrugs 25(1):1-11 (2011).

Chames et al., mAbs 1:6, 539-547 (2009).

Tutt et al., J. Immunol. 147:60 (1991).

Gleason et al., Mol. Cancer. Ther. 11(12):2674-84 (2012).

Wang et al., J. Biochem. 135(4):555-65 (2004).

Caron et al., J. Exp Med. 176:1191-1195 (1992).

Wolff et al., Cancer Research 53:2560-2565 (1993).

Stevenson et al., Anti-Cancer Drug Design 3:219-230 (1989).

Kenderian et al., Cancer Res. 74(22):6383-9 (2014).

Groves et al., J. Immunol. Methods, 313:129-39, 2006.

Barbas et al., Proc Natl. Acad. Sci. USA, 91:3809-13, 1994.

Chow and Ho, Sci Transl Med 5:216rv4 (2013).

Montenegro et al., Adv. Drug Delivery Rev. 65:677-688 (2013).

Rohloff et al., Molecular Therapy Nucleic Acids, 3:e201 (2014).

Zhu et al., Theranostics 4(9):931-944 (2014).

Ellington and Szostak, Nature 346:818-822 (1990).

(56) References Cited

OTHER PUBLICATIONS

Weiner et al., Nature Rev. Immunol. 10:317-327 (2010).
Slaney et al., Cancer Res. 74:7168-7174 (2014).
Freireich et al., Cancer Chemotherapy Rep. 50(4):219-244 (1966).
Therasse et al., J. Natl. Cancer Inst. 92:205-16, 2000.
Chen et al., J. Proteome Res. 2009;8:651-61.
Ni et al., PLoS One 7:e52598, 2012.
Pommier, et al. Unresolved endoplasmic reticulum stress engenders immune-resistant, latent pancreatic cancer metastases. Science. 2018;360(6394).
James MA, Wen W, Wang Y, Byers LA, Heymach JV, Coombes KR, et al. Functional characterization of CLPTM1L as a lung cancer risk candidate gene in the 5p15.33 locus. PLoS One. 2012;7(6):e36116.
Clarke WR, Amundadottir L, James MA. CLPTM1L/CRR9 Ectodomain Interaction with GRP78 at the Cell Surface Signals for Survival and Chemoresistance upon ER Stress in Pancreatic Adenocarcinoma Cells, Int J Cancer, 144, 1367-1378 (2019).
Colombo J, Fachel AA, De Freitas Calmon M, Cury PM, Fukuyama EE, Tajara EH, et al. Gene expression profiling reveals molecular marker candidates of laryngeal squamous cell carcinoma. Oncol Rep. 2009;21(3):649-63.
Crow J, Atay S, Banskota S, Artale B, Schmitt S, Godwin AK. Exosomes as mediators of platinum resistance in ovarian cancer. Oncotarget. 2017;8(7):11917-36.

Da Cunha JP, Galante PA, de Souza JE, de Souza RF, Carvalho PM, Ohara DT, et al. Bioinformatics construction of the human cell surfaceome. Proc Natl Acad Sci U S A. 2009;106(39):16752-7.
Gifford JB, Huang W, Zeleniak AE, Hindoyan A, Wu H, Donahue TR, et al. Expression of GRP78, Master Regulator of the Unfolded Protein Response, Increases Chemoresistance in Pancreatic Ductal Adenocarcinoma. Mol Cancer Ther. 2016;15(5):1043-52.
Gundry RL, Riordon DR, Tarasova Y, Chuppa S, Bhattacharya S, Juhasz O, et al. A cell surfaceome map for immunophenotyping and sorting pluripotent stem cells. Mol Cell Proteomics. 2012;11(8):303-16.
Gyorffy B, Lanczky A, Szallasi Z. Implementing an online tool for genome-wide validation of survival-associated biomarkers in ovarian-cancer using microarray data from 1287 patients. Endocr Relat Cancer. 2012;19(2):197-208.
Izzo G, Freitas EL, Krepischi AC, Pearson PL, Vasques LR, Passos-Bueno MR, et al. A microduplication of 5p15.33 reveals CLPTM1L as a candidate gene for cleft lip and palate. Eur J Med Genet. 2013;56(4):222-5.
James MA, Vikis HG, Tate E, Rymaszewski AL, You M. CRR9/CLPTM1L regulates cell survival signaling and is required for Ras transformation and lung tumorigenesis. Cancer Res. 2014;74(4):1116-27.

* cited by examiner

FIG. 3

Sequence analysis for CLPTML

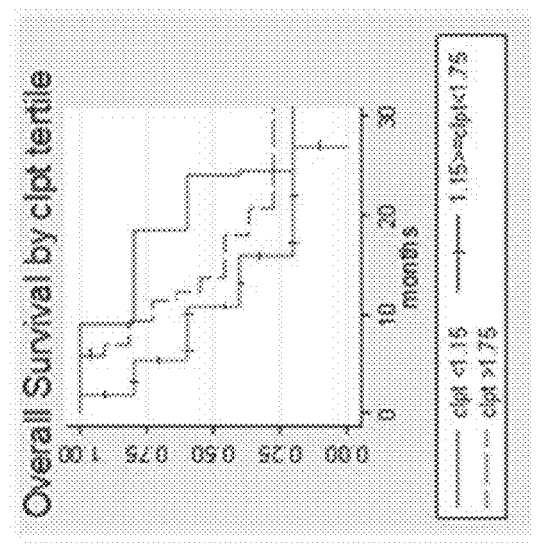
FIG. 5A
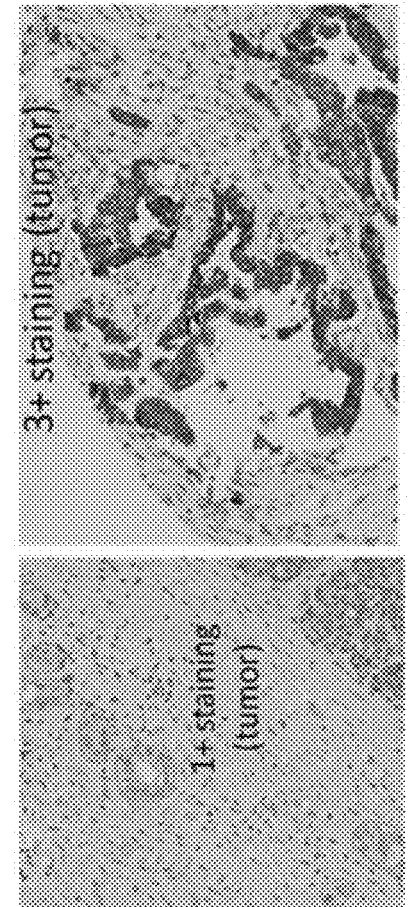
FIG. 5B
FIG. 5C

FIG. 10

Characterization of in-vitro anti-tumor effects of monoclonal anti-CLPTM1L antibodies.

| mAb | Targets Both Isoforms | IF Staining Intensity A549 | Punctate Surface Staining A549 | pAkt Inhibition | | Bcl-xL Inhibition | | CDDP Sensitization | | Tumor Spheroid Growth |
|---|---|---|---|---|---|---|---|---|---|---|
| | | | | A549 | H838 | A549 | H838 | A549 | H838 | H838 |
| 6-1 | - | +++ | - | ++ | +/- | + | - | + | + | - |
| 6-2 | - | + | - | + | +/- | + | - | - | +/- | - |
| 7-1 | - | ++ | - | +/- | - | +/- | - | - | - | - |
| 7-2 | - | + | - | - | - | +/- | - | - | +/- | - |
| 8 | + | ++ | + | +/- | - | - | - | + | + | - |
| 9-1 | + | ++ | + | + | - | + | - | +/- | + | - |
| 9-2 | + | + | + | - | +/- | +/- | +/- | +/- | - | - |
| 10-1 | + | ++ | + | + | +/- | +/- | +/- | - | +/- | +/- |
| 10-2 | + | ++ | + | ++ | + | + | + | +/- | +/- | + |
| 10-3 | + | +++ | + | ++ | + | + | + | +/- | +/- | + |

FIG. 16

Human Ovarian Tumor Cells 102-5FL internalization vs. IgG1 control +/- 5X competitor Unlabeled competitor IgG1 or 102-5FL added in 5X molar excess.
Internalization rate saturates between 50 and 100 nM ESS102-5.

FIG. 18
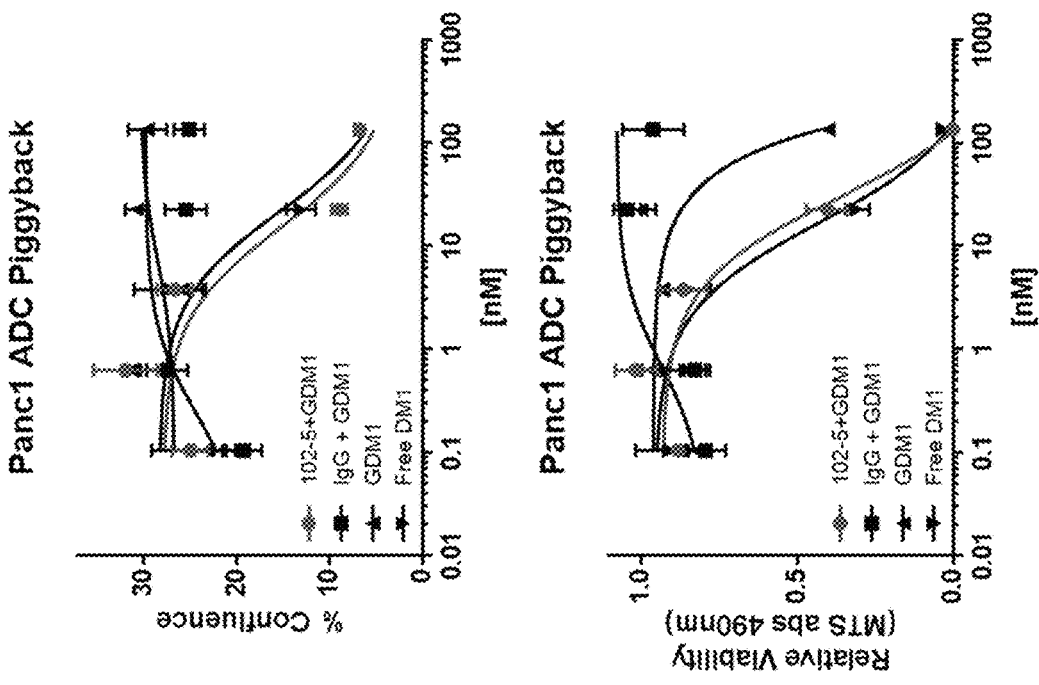
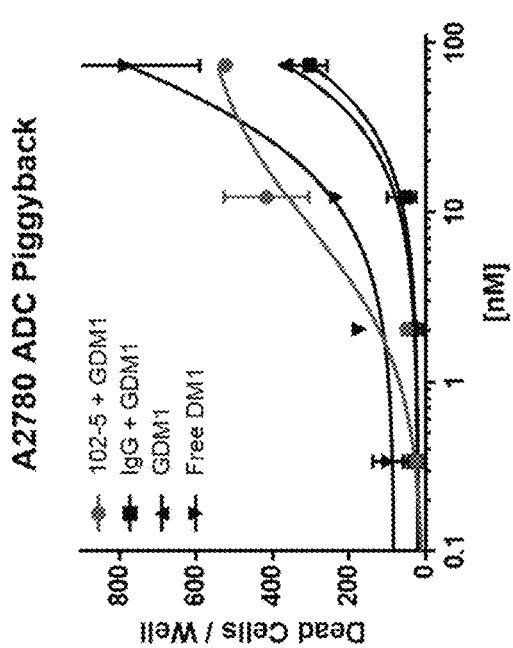

FIG. 23
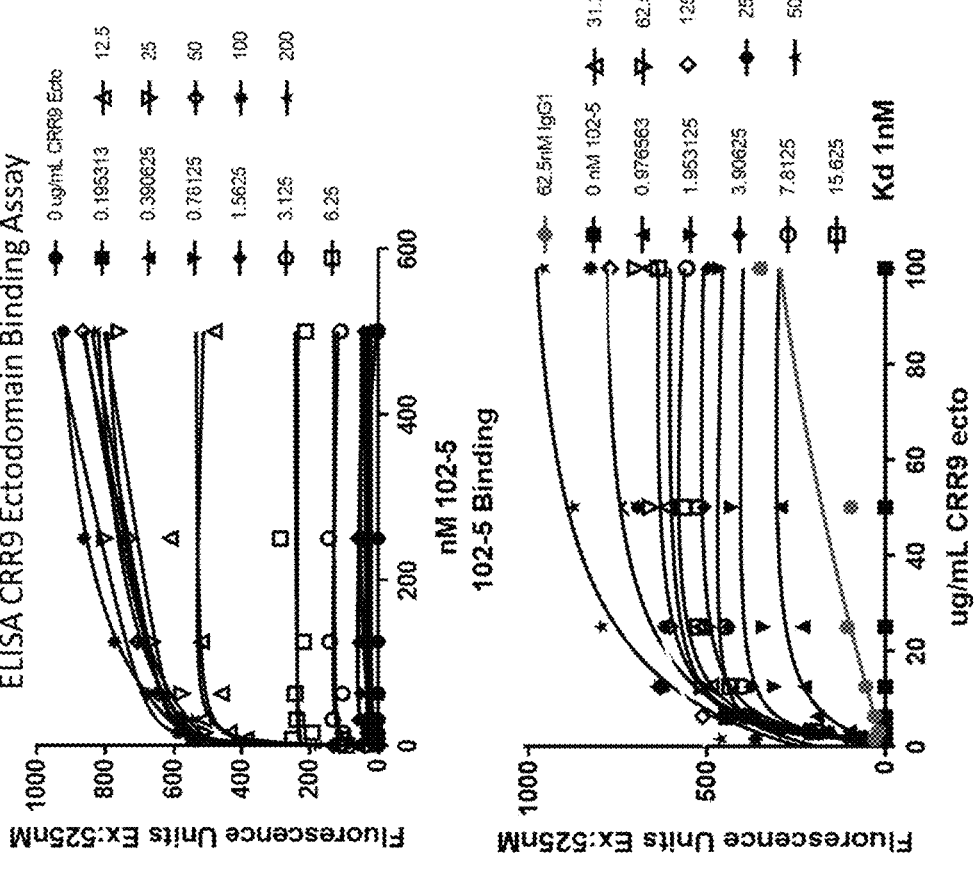
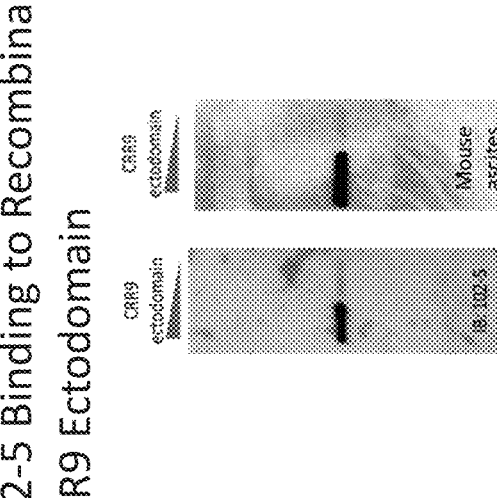
102-5 Binding to Recombinant
CRR9 Ectodomain

| Sample ID | Conc. (nM) | Response | KD (M) |
|---|---|---|---|
| ESS01025A | 1000 | 4.3217 | 1.16E-08 |
| ESS01025A | 500 | 3.561 | 1.16E-08 |
| ESS01025A | 250 | 2.5476 | 1.16E-08 |
| ESS01025A | 62.5 | 0.461 | 1.16E-08 |
| ESS01025A | 31.3 | 0.1475 | 1.16E-08 |
| ESS01025A | 15.6 | 0.0523 | 1.16E-08 |

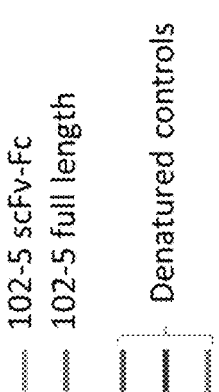
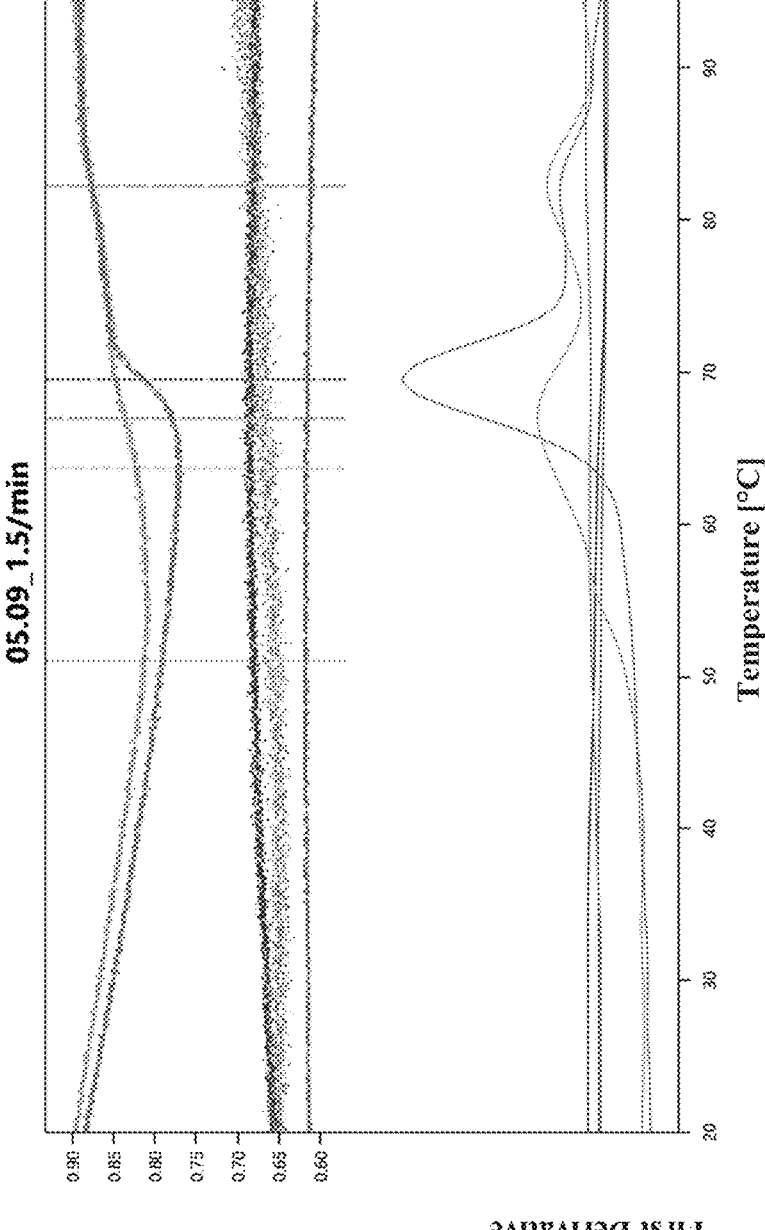
FIG. 26

Control Kidney Casp3 | Control Kidney HE | 102-5 Kidney Casp3 | 102-5 Kidney HE

Control Liver Casp3 | Control Liver HE | 102-5 Liver Casp3 | 102-5 Liver HE

Control Tumor Casp3 | Control Tumor HE | anti-CRR9 Tumor Casp3 | anti-CRR9 Tumor HE Tonsil Casp3 Pos. Cotnrol Increased apoptosis and non-viable tumor tissue with ESS102-5 treatment Tissue Toxicity Anti-Tumor Activity

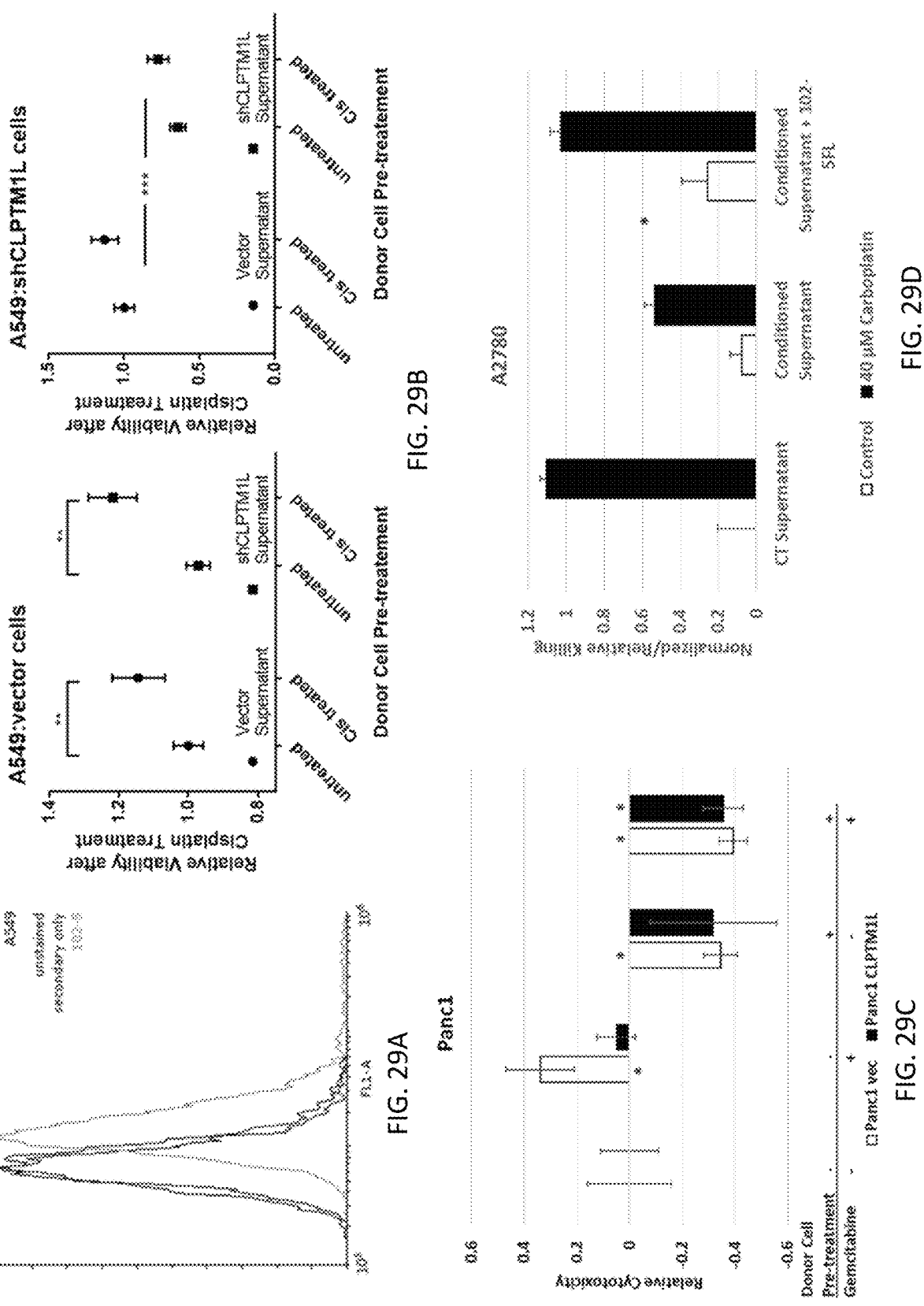

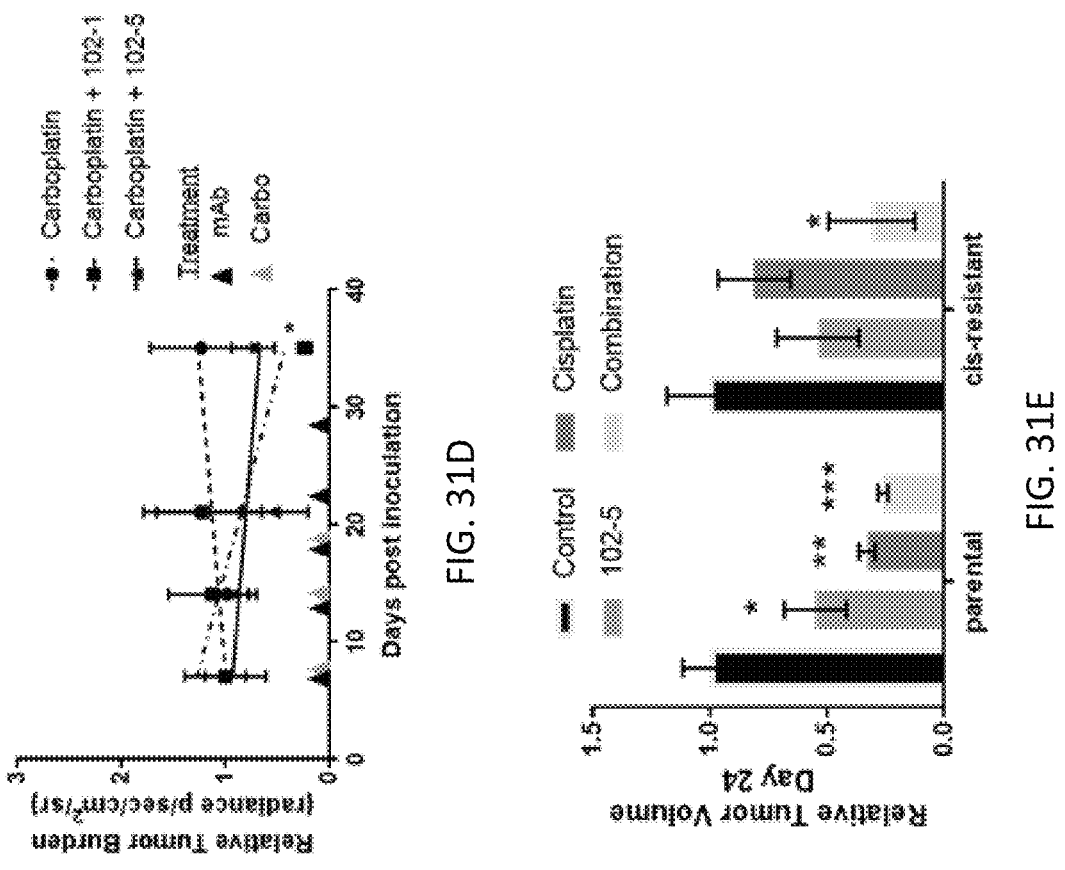
FIG. 31D
FIG. 31E
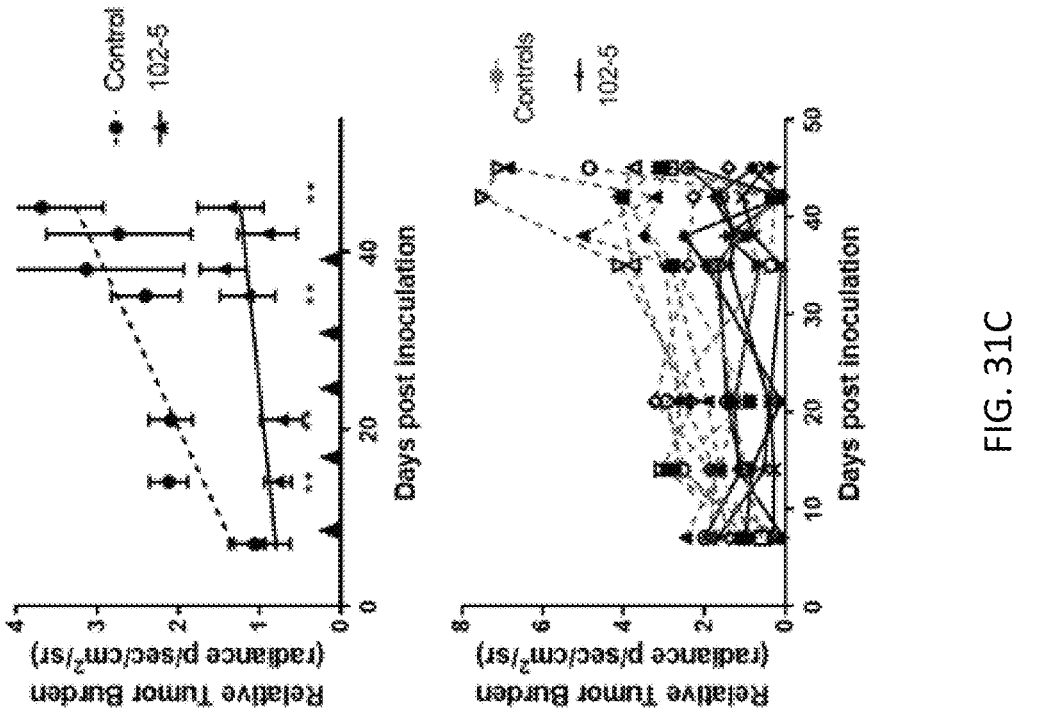
FIG. 31C

FIG. 33

TARGETING CLPTM1L FOR TREATMENT AND PREVENTION OF CANCER

CROSS-REFERENCE TO RELATED APPLICATIONS

This application is a continuation of U.S. application Ser. No. 17/286,748 filed on Apr. 19, 2021, which is the U.S. National Stage of PCT/US2019/056251 filed on Oct. 15, 2019, which claims the benefit of U.S. Provisional Application No. 62/750,450, filed Oct. 25, 2018, the disclosures of which are hereby incorporated by reference in their entireties for all purposes.

SEQUENCE LISTING

A Sequence Listing accompanies this application and is submitted as an XML file of the sequence listing named "65005301093.xml" which is 89,698 bytes in size and was created on Sep. 20, 2024. The sequence listing is electronically submitted via Patent Center with the application and is incorporated herein by reference in its entirety.

BACKGROUND

Cancer is a disease that begins with mutation of oncogenes and tumor suppressor genes. Mutation of these critical genes allows for a cancer cell to evolve and ultimately results in pathogenic replication (a loss of normal regulatory control leading to excessive cell proliferation) of various given types of cells found in the human body. Tumor formation, tumor survival, and cancer metastasis require anchorage-independent growth and protection from genotoxin-induced apoptosis and anoikis, a programmed cell death mechanism associated with detachment of tumor cells from an extracellular substrate. Tumor cells require protection from apoptosis and anoikis to invade surrounding tissue and to undergo metastasis.

There remains a need in the art for methods for treating or preventing cancer and, in particular, for methods which slow or curb tumor growth and prevent metastasis.

BRIEF SUMMARY OF THE DISCLOSURE

To address the deficiencies outlined above, this disclosure provides therapeutic agents having specificity for human CLPTM1L/CRR9 polypeptide. In particular, provided herein are fully human monoclonal antibodies against human CLPTM1L/CRR9 protein and methods of using such antibodies for treating or preventing a cancer, pre-cancerous lesion, or other disease condition associated with CLPTM1L/CRR9 protein dysfunction (e.g., pathogenic production, modification, or function.

In a first aspect, the present invention provides an isolated antibody, or an antigen binding fragment thereof capable of binding to human CLPTM1L. The antibody can comprise or consist essentially of (a) a heavy chain variable region comprising a CDRH1 of SEQ ID NO:36, a CDRH2 of SEQ ID NO:37, and a CDRH3 of SEQ ID NO:38; and a light chain variable region comprising a CDRL1 of SEQ ID NO:39, a CDRL2 of SEQ ID NO:40, and a CDRL3 of SEQ ID NO: 41; (b) a heavy chain variable region comprising a CDRH1 of SEQ ID NO:42, a CDRH2 of SEQ ID NO:43, and a CDRH3 of SEQ ID NO:44; and a light chain variable region comprising a CDRL1 of SEQ ID NO:45, a CDRL2 of SEQ ID NO:46, and a CDRL3 of SEQ ID NO:47; (c) a heavy chain variable region comprising a CDRH1 of SEQ ID NO:48, a CDRH2 of SEQ ID NO: 49, and a CDRH3 of SEQ ID NO:50; and a light chain variable region comprising a CDRL1 of SEQ ID NO:51, a CDRL2 of SEQ ID NO:52, and a CDRL3 of SEQ ID NO:53; (d) a heavy chain variable region comprising a CDRH1 of SEQ ID NO:54, a CDRH2 of SEQ ID NO:55, and a CDRH3 of SEQ ID NO:56; and a light chain variable region comprising a CDRL1 of SEQ ID NO: 57, a CDRL2 of SEQ ID NO:58, and a CDRL3 of SEQ ID NO:59; or (e) a heavy chain variable region comprising a CDRH1 of SEQ ID NO:60, a CDRH2 of SEQ ID NO:61, and a CDRH3 of SEQ ID NO:62; and a light chain variable region comprising a CDRL1 of SEQ ID NO: 63, a CDRL2 of SEQ ID NO:64, and a CDRL3 of SEQ ID NO:65. The antibody can be a human antibody comprising or consisting essentially of (i) a light chain comprising SEQ ID NO: 26 or a sequence having at least 85% sequence identity to SEQ ID NO:26, and a heavy chain comprising SEQ ID NO:27 or a sequence having at least 85% sequence identity to SEQ ID NO: 27; (ii) a light chain comprising SEQ ID NO:28 or a sequence having at least 85% sequence identity to SEQ ID NO:28, and a heavy chain comprising SEQ ID NO:29 or a sequence having at least 85% sequence identity to SEQ ID NO:29; (iii) a light chain comprising SEQ ID NO:30 or a sequence having at least 85% sequence identity to SEQ ID NO:30, and a heavy chain comprising SEQ ID NO:31 or a sequence having at least 85% sequence identity to SEQ ID NO:31; (iv) a light chain comprising SEQ ID NO:32 or a sequence having at least 85% sequence identity to SEQ ID NO:32, and a heavy chain comprising SEQ ID NO:33 or a sequence having at least 85% sequence identity to SEQ ID NO:33; or (v) a light chain comprising SEQ ID NO:34 or a sequence having at least 85% sequence identity to SEQ ID NO:34, and a heavy chain comprising SEQ ID NO:35 or a sequence having at least 85% sequence identity to SEQ ID NO:35. The antibody can comprise a variant Fc domain. The antibody can be a monoclonal antibody. The monoclonal antibody can be a chimeric antibody, human antibody, humanized antibody, recombinant antibody, engineered antibody, conjugated antibody, bispecific monoclonal antibody, or fragment thereof. The antibody can be an immunoconjugate comprising a therapeutic agent selected from a pharmacologic agent, radioisotope, and toxin; and a linker.

In another aspect, provided herein is a pharmaceutical composition comprising an antibody of according to this disclosure and a pharmaceutically acceptable carrier.

In a further aspect, provided herein is an article of manufacture comprising a pharmaceutical composition of this disclosure, and an insert providing instructions for treating a tumor in a human subject.

In another aspect, provided herein is a method for treating or preventing a tumor comprising administering to a subject in need thereof a therapeutically effective amount of an antibody of this disclosure to a subject in need thereof, whereby the tumor is treated or prevented in the subject. The subject can be a human subject at risk of, diagnosed as having, or exhibiting a symptom associated with the tumor. The antibody can be a monoclonal antibody. The monoclonal antibody can be a chimeric antibody, human antibody, humanized antibody, recombinant antibody, engineered antibody, conjugated antibody, bispecific monoclonal antibody, or fragment thereof. The antibody can be an immunoconjugate comprising a therapeutic agent selected from a pharmacologic agent, radioisotope, and toxin; and a linker. The tumor can be a solid tumor selected from the group consisting of glioblastoma, sarcoma, carcinoma, and lymphoma. The tumor can be associated with a cancer or preneoplastic lesion selected from the group consisting of lung cancer, pancreatic cancer, prostate cancer, skin cancer, bladder cancer, kidney cancer, ovarian cancer, colon cancer, colorectal cancer, breast cancer, cervical cancer, brain cancer, esophageal cancer, and stomach cancer, or a precancerous lesion thereof. The tumor can be associated with lung cancer or preneoplastic lesion thereof. The subject can be a human. The tumor can exhibit resistance to a chemotherapeutic agent. The chemotherapeutic agent can be selected from cisplatin, gemcitabine, carboplatin, carmustine (BCNU), methotrexate, fluorouracil (5-FU), goserelin, leuprolide, tamoxifen, docetaxel, paclitaxel, aldesleukin, interleukin-2, etoposide (VP-16), interferon α, tretinoin (ATRA), bleomycin, dactinomycin, daunorubicin, doxorubicin, mitomycin, vinblastine, and vincristine. The antibody can be administered with a pharmaceutically acceptable carrier.

These and other features, aspects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. The detailed description makes reference to the following drawings, wherein:

FIG. 3 depicts selection of epitopes to raise monoclonal antibodies specific for human CLPTM1L protein. The focus region for monoclonal antibody design included the ordered regions of the predicted extracellular domain. Glycosylation sites were excluded.

FIGS. 5A-5C present graphs and images demonstrating that CLPTM1L expression is increased in pancreatic tumor tissue over normal pancreatic ductal epithelia and that higher expression is correlated with poor survival. (A) Immunohistochemical scoring of staining with antibody specific to CLPTM1L in pancreatic tumor vs. normal ductal epithelial tissues in 31 patients. (B) Kaplan-Meier survival curves stratified into tertiles of CLPTM1L expression. (C) Representative staining of tumor.

FIG. 10 summarizes characterization of in vitro antitumor effects of monoclonal anti-CLPTM1L antibodies.

Figure 16:
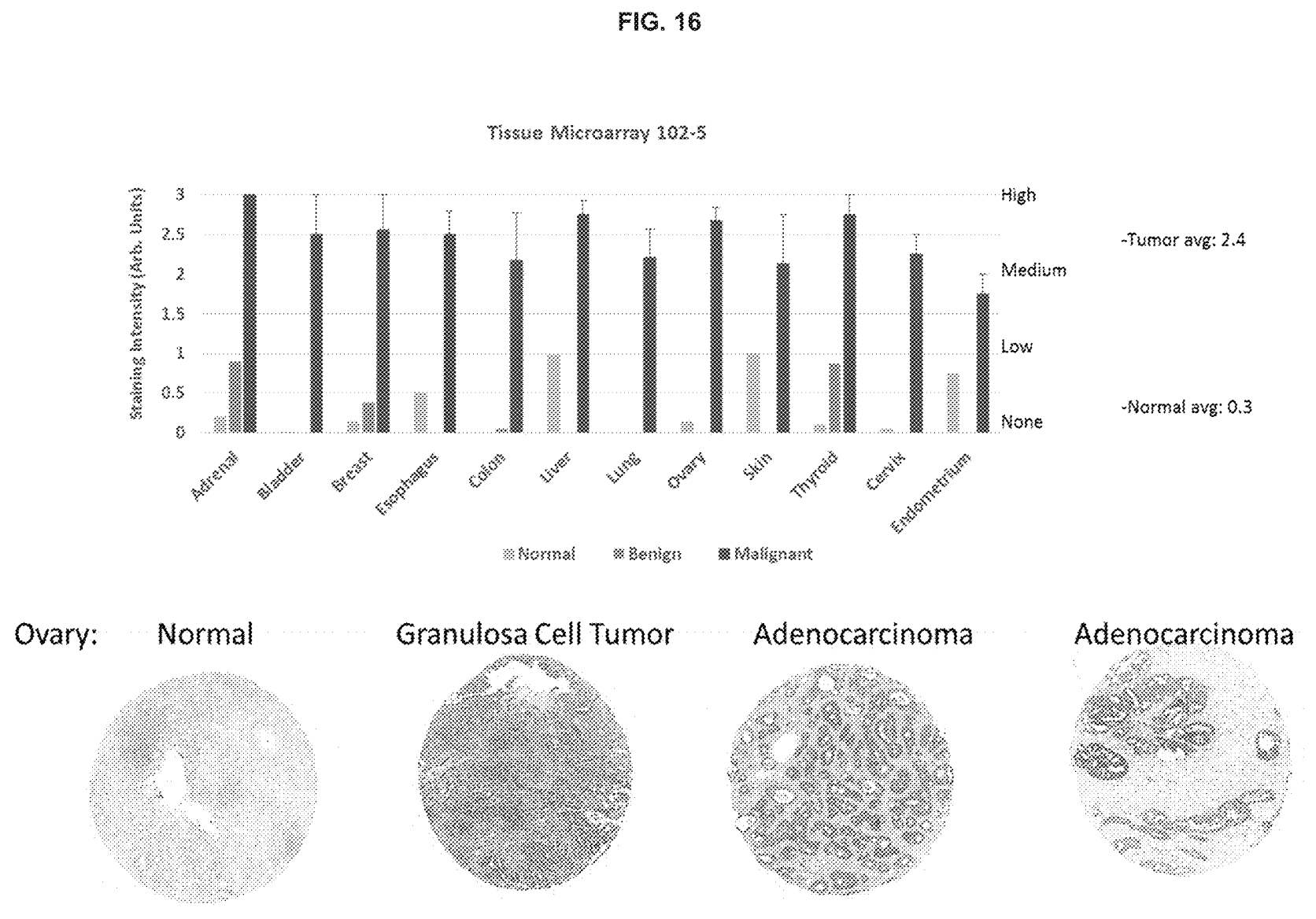

FIG. 16 presents data characterizing tissue cross-reactivity (top) and tumor specificity (bottom) of clone 102-5. Images show immunohistochemical staining of a tumor microarray with normal, benign, and tumor tissues with 102-5, demonstrating binding to tumor tissue with little to no binding to normal or benign tissues.

FIG. 18 demonstrates that 102-5 bound to Protein-G-DM1 toxin effectively kills ovarian and pancreatic tumor cells as a "piggyback" antibody-drug conjugate (ADC) with similar potency as free toxin. Control IgG1-ADC does not exhibit killing activity.

FIG. 23 demonstrates specific binding of 102-5 to the CRR9 ectodomain by western blotting of purified CRR9 ectodomain (left), and ELISA with the same, showing a Kd of 1 nM (right).

FIG. 26 demonstrates antibody stability in NanoDSF melt curves by intrinsic tryptophan and tyrosine fluorescence to observe unfolding. Antibodies stored at 4° C. in PBS pH 7.4 for 5 months. 102-5 is demonstrated to be stable under these conditions.

FIGS. 29A-29D demonstrate chemoprotection by culture supernatants and inhibition of that chemoprotection by treatment with 102-5 anti-CRR9. (A) Flow cytometry histograms of fluorescent labeling of live A549 cells with 102-5 anti-CLPTM1L primary and Alexafluor-488-conjugated secondary antibodies. (B) Relative viability (MTS) of A549 cells (vector control, or with CLPTM1L shRNA knockdown (shCLPTMIL) after exposure to cisplatin and culture supernatants from either vector control or CLPTM1L shRNA cells that were untreated or pre-treated with cisplatin (x axis). $p=0.003$, $*p=0.0001$. (C) Relative killing (live imaging cytotoxicity) of Panc1 pancreatic tumor cells after 24-hour treatment with 100 nM gemcitabine and 72-hour culture supernatants that were either untreated or pre-treated with 20 nM gemcitabine. (D) Relative killing by 40 μM carboplatin (live imaging cytotoxicity) of ovarian tumor cells treated with supernatants from control or 10 μM carboplatin-conditioned A2780 donor cells at 60 hours post-carboplatin treatment. Supernatants in the 102-5 groups were pre-treated with 100 nM 102-5 anti-CLPTM1L overnight. $*p<0.05$, $**p<0.005$.

FIGS. 31A-31F demonstrate orthotopic syngeneic ovarian isograft and xenograft models of anti-CRR9 therapy and platinum combination therapy. (A) Flow cytometry histograms of fluorescent labeling of live ID8-luc cells with 102-5 anti-CLPTM1L primary and Alexafluor-488-conjugated secondary antibodies. (B) Viability of ID8-luc cells treated with 100 nM 102-5 anti-CLPTM1L and/or 40 μM carboplatin for 5 days. (C) Relative tumor burden as measured by luciferin luminescence live animal imaging of control vs. 10 mg/kg 102-5 anti-CLPTM1L treated ID8-luc isograft groups (left) and individual animals (right). (D) Relative tumor burden as measured by luciferin luminescence live animal imaging of 10 mg/kg carboplatin plus either control or 102-5 anti-CLPTM1L (10 mg/kg) treated groups (left) and individual animals (right). (E) Final relative mean volumes of SL3 and SL3cis xenograft tumors 24 days post-inoculation. Mice were treated with 5 mg/kg 102-5 and/or 2.5 mg/kg cisplatin I.P. weekly. (F) Mean volumes of SL3 and SL3cis xenograft tumors relative to group mean volume after sorting from days 0 to 24 post-inoculation. *p<0.05, p<0.005, *p<0.0005. Error bars represent standard error of the mean.

FIG. 33 provides a table summary of chemosensitivity data from FIGS. 29 and 30. Panel 29B data expressed as relative to control columns left of dotted lines. Chemoresistance=statistically significant decrease in che-motherapeutic killing.

DETAILED DESCRIPTION OF THE INVENTION

Figures 1A, 1B:
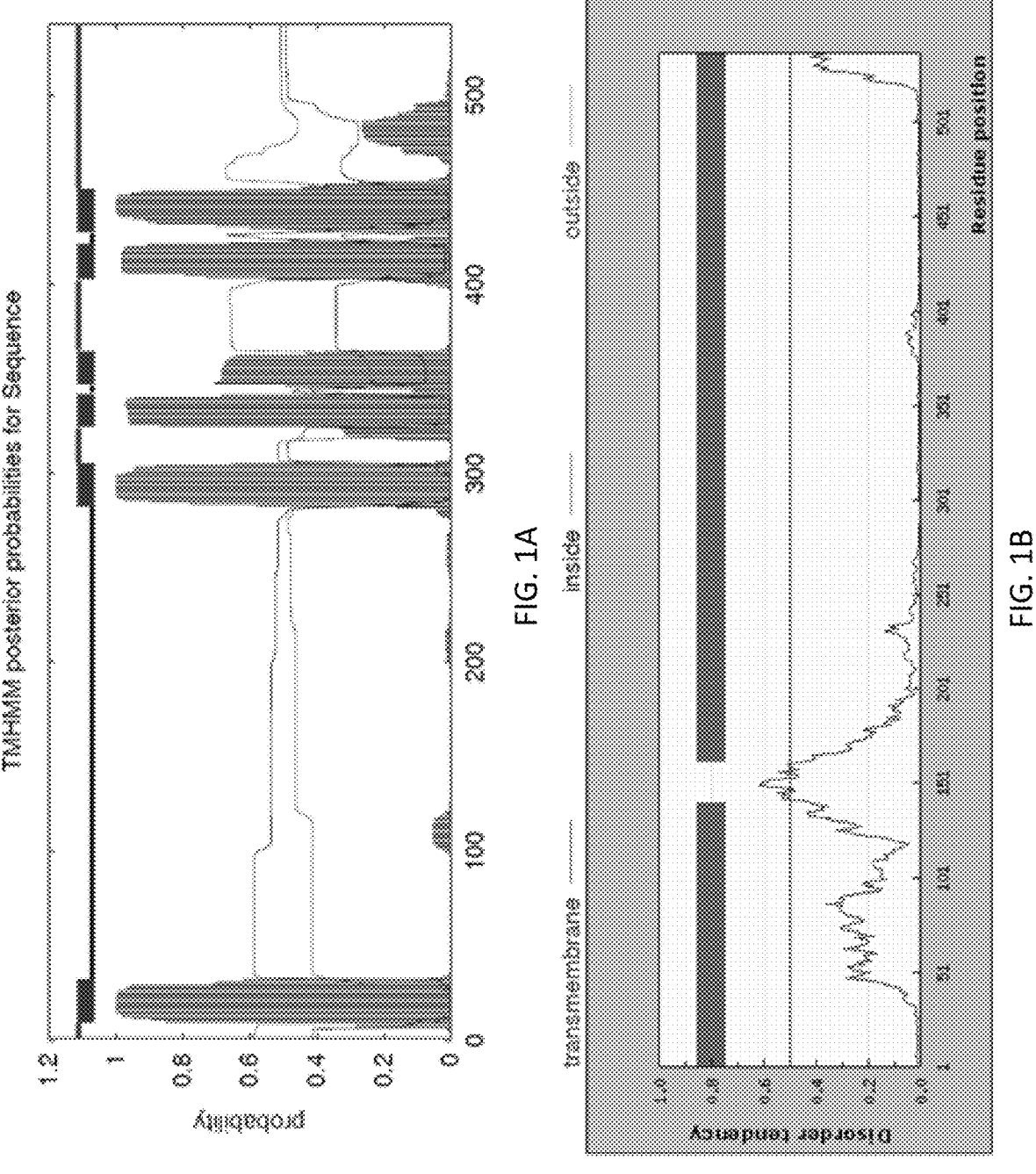
FIGS. 1A-1B present structural data demonstrating the presence of two separate globular domains separated by a small disordered region (amino acid residues 142-162) within the larger extracellular region.

All publications, patents, and patent applications mentioned in this specification are herein incorporated by reference in their entirety as if each individual publication, patent, and patent application was specifically and individually indicated to be incorporated by reference.

The present invention is based at least in part on the Inventors' discovery that CLPTM1L is commonly over-expressed in non-small cell lung cancer (NSCLC) and that it protects lung tumor cells from genotoxic apoptosis. In particular, depletion of CLPTM1L robustly and significantly inhibited tumorigenesis in vivo in multiple models. Cisplatin Resistance Related Protein-9 (CRR9), otherwise known as Cleft-Lip and Palate Transmembrane Protein-Like Protein 1 (CLPTM1L), is located at chromosome 5p15.33 as defined by multiple Genome Wide Association (GWA) studies. The CLPTM1L gene lies within a locus on chromosome 5 that is frequently gained in copy number early in lung cancer and that is associated by genotype with lung cancer susceptibility. For example, genetic variants near and within the CLPMT1L gene are associated with lung cancer, cervical cancer, ovarian cancer, pancreatic cancer, bladder cancer, glioma, prostate cancer, basal cell carcinoma, and melanoma. Although the mechanism of action remains to be fully elucidated, it is believed that CLPTM1L is involved in Bcl-xL survival protein accumulation. Indeed, the Inventors previously demonstrated that CLPTM1L protects chemo-therapeutically treated tumor cells from genotoxin-induced apoptosis and that CLPTM1L is required for anchorage independent growth and for Ras-driven lung tumorigenesis.

The Inventors further discovered that CLPTM1L localizes to the plasma membrane, and that polyclonal antibodies targeting the N-terminal region of the CLPTM1L protein, which is predicted to be extracellular, elicit comparable phenotypes to those elicited by RNA interference-mediated depletion of CLPTM1L; specifically, Bcl-xL and Akt inhibition, chemosensitization, and anchorage dependence. Accordingly, the present invention relates to immunoglobulins, compositions, and methods of using such compositions for targeting human CLPTM1L for the prevention or treatment of solid tumors and cancers and for chemosensitization of tumor cells. As used herein, the term "solid tumor" refers to an abnormal mass of tissue that usually does not contain cysts or liquid areas. Non-cancerous tumors are described as "benign," while cancerous tumors are described as "malignant." Different types of solid tumors are named for the particular cells that form them, for example, sarcomas formed from connective tissue cells (such as bone cartilage, fat), carcinomas formed from epithelial tissue cells (such as breast, colon, pancreas), and lymphomas formed from lymphatic tissue cells (such as lymph nodes, spleen, thymus). Treatment of all types of solid tumors is within the scope of this invention.

The human CLPTM1L gene (SEQ ID NO:1; Genbank ID AAH25305.1) encodes a 538 amino acid polypeptide (SEQ ID NO:2; UniProt ID: Q96KA5.1). Gene products of human CLPTM1L include a primary mRNA (Genbank ID BC016399.1; SEQ ID NO:3) and two additional predicted transcript splice variants (Ensembl transcript IDs: ENST00000320927 and ENST00000507807). These predicted splice variants encode proteins of 502 and 369 (SEQ ID NO: 71) amino acids, respectively. Splice variant prediction methods are available at useast.ensembl.org/info/docs/genebuild/genome_annotation.html on the World Wide Web.

Compositions of the Invention

In one aspect, the present invention provides compositions comprising CLPTM1L-targeting agent having specificity for at least a portion of a CLPTM1L polypeptide. As described herein, compositions of the present invention are useful as therapeutic agents and pharmaceutical compositions for a variety of clinical applications. In particular, provided herein are therapeutic compositions comprising one or more CLPTM1L-targeting agent including antibodies, antibody fragments, immunoconjugates, bispecific antibodies, trispecific antibodies, and chimeric antigen receptors having specificity for (i.e., targeted to) one or more CLPTM1L epitopes. Also provided are compositions comprising one or more CLPTM1L-targeting peptides. As used herein, a CLPTM1L-targeting agent is a molecule or complex that specifically binds to a CLPTM1L polypeptide or to one or more epitopes of a CLPTM1L polypeptide or fragment thereof and/or competes for binding at one or more epitopes of a CLPTM1L polypeptide or fragment thereof.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with, any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

As used herein, the terms "antibody" and "antibodies" are synonymous with "immunoglobulin" and "immunoglobulins," and the terms are used interchangeably herein. The terms "antibody" and "antibodies" include whole immunoglobulins including, without limitation, polyclonal antibodies or monoclonal antibodies (mAbs). The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. The term antibody encompasses various broad classes of polypeptides that can be distinguished biochemically. It is the nature of the heavy chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization.

Human light chains are classified as kappa and lambda light chains. Heavy chains are classified as mu, delta, gamma, alpha, or epsilon ($\mu$, $\delta$, $\gamma$, $\alpha$, $\epsilon$), and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. The variable regions of each light/heavy chain pair form the antibody binding site. Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

Antibodies appropriate for the present invention also include antibody fragments or modified products thereof, provided that they can be suitably used in the present invention. Appropriate antibody fragments comprise at least one variable domain of an immunoglobulin, such as single variable domains Fv (Skerra & Pluckthun, *Science* 240:1038-41 (1988)), scFv (Bird et al., *Science* 242:423-26 (1988); Huston et al., *Proc. Natl. Acad. Sci. USA* 85:5879-83 (1988)), Fab, $(Fab')_2$ or other proteolytic fragments. The terms "antibody" and "antibodies" further include chimeric antibodies; human and humanized antibodies; recombinant and engineered antibodies, conjugated antibodies, and fragments thereof. Humanized antibodies are antibodies wherein the complementarity determining regions (CDRs) of an antibody from a mammal other than human (e.g., a mouse antibody) are transferred into the CDRs of human antibodies. Chimeric and humanized antibodies can be made according to standard protocols such as those disclosed in U.S. Pat. No. 5,565,332. Other antibody formats are described in, for example, "Antibody Engineering," McCafferty et al. (Eds.) (IRL Press 1996). Also encompassed in the invention are CLPTM1L-targeting immunoglobulins that have been conjugated or bound in some manner to various molecules including, without limitation, polyethylene glycol (PEG), radioactive substances, and drugs. Such conjugated antibodies can be obtained by chemically modifying a CLPTM1L-targeting immunoglobulin. Methods for obtaining conjugated antibodies are known and available in the art.

The antibodies of the present invention may be polyclonal or monoclonal antibodies. Preferably, the CLPTM1L-targeting immunoglobulins are monoclonal. Methods of producing polyclonal and monoclonal antibodies are known in the art and described generally, e.g., in U.S. Pat. No. 6,824,780. Typically, the antibodies of the present invention are produced recombinantly, using vectors and methods available in the art, as described further below. Human antibodies may also be generated by in vitro activated B cells (see U.S. Pat. Nos. 5,567,610 and 5,229,275). Human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno.,* 7:33 (1993); U.S. Pat. Nos. 5,545,806, 5,569, 825, 5,591,669; 5,545,807; and WO 97/17852. Such animals may be genetically engineered to produce human antibodies comprising a polypeptide of the present invention.

The source of the antibodies described herein is not particularly restricted in the present invention; however, the antibodies are preferably derived from mammals, and more preferably derived from humans. This disclosure, including the Examples section, provides characterization of fully human CLPTM1L-specific monoclonal antibodies produced using CDR sequences of scFv antibody fragments binding the target epitope within CLPTM1L as panned from a naïve human phage display library, including nucleotide and amino acid sequence analyses of the heavy and light chains of such antibodies. These CDR sequences are expressed in a fully human IgG1 framework.

Alternatively, monoclonal antibodies appropriate for the present invention can be prepared using antibody engineering methods such as phage display. Methods for obtaining highly specific antibodies from antibody phage display libraries are known in the art, and several phage antibody libraries are commercially available from, for example, MorphoSys (Martinsried, Germany), Cambridge Antibody Technology (Cambridge UK) and Dyax (Cambridge Mass.). Suitable phage display methods are described, for example, in U.S. Pat. Nos. 6,300,064 and 5,969,108, and in "Antibody Engineering," McCafferty et al. (Eds.) (IRL Press 1996)). Once the antibody heavy and light chain genes are recovered from the phage antibodies, antibodies in any suitable format may be prepared for use according to the present invention, e.g., whole antibodies, Fab fragments, scFv, etc.

Antibodies disclosed herein may be from any animal origin including birds and mammals. Preferably, the antibodies are human, murine, donkey, rabbit, goat, guinea pig, camel, llama, horse, or chicken antibodies.

Polyclonal antibodies appropriate for the present invention can be prepared by may also be prepared using traditional animal-based methods. For example, an appropriate animal can be immunized using a polypeptide immunogen (e.g., peptide of CLPTM1L). Polypeptide antibody titers in the immunized animal can be monitored over time by standard techniques, such as with an enzyme linked immunosorbent assay (ELISA) using immobilized polypeptide. Antibodies specific to the antigen can be isolated from the mammal (e.g., from the blood) and further purified by techniques known to those practicing in the art including, for example, protein A chromatography to obtain the IgG fraction. In some cases, at an appropriate time after immunization (e.g., when the antibody titers are highest) antibody-producing cells can be obtained from the animal and used to prepare monoclonal antibodies.

As used herein, the terms "epitope" or "antigenic determinant" refer to a site on an antigen (e.g., on CLPTM1L) to which an immunoglobulin or antibody specifically binds. Generally, an epitope includes at least 3, 4, 5, 6, 7, 8, 9, 10, 11, 12, 13, 14, or 15 consecutive or non-consecutive amino acids in a unique spatial conformation. See, e.g., Epitope Mapping Protocols in Methods in Molecular Biology, Vol. 66, G. E. Morris, Ed. (1996). As used herein, the terms "specific binding," "selective binding," "selectively binds," and "specifically binds," refer to an antibody binding to an epitope via its antigen-binding domain, and that the binding entails some complementarity between the antigen-binding domain and the epitope. Generally, an antibody specifically or selectively binds with an affinity (generally represented by the dissociation constant $K_D$) of approximately less than $10^{-7}$ M, such as approximately less than $10^{-8}$ M, $10^{-9}$ M, or $10^{-0}$ M, or lower. As used herein, the term "affinity" denotes the strength of the sum total of non-covalent interactions between a single binding site of a molecule (e.g., a peptide, polypeptide, or antibody) and its binding partner (e.g., a target or an antigen). Unless indicated otherwise, as used herein, "binding affinity" refers to intrinsic binding affinity which reflects a 1:1 interaction between members of a binding pair (e.g., between a peptide and its target, or between an antibody and its antigen). The terms "$K_D$" and "$K_d$" are synonymous and refer to the dissociation equilibrium constant of a particular molecule X-binding partner Y interaction. Affinities of antibodies can be readily determined using methods known in the art such as surface plasmon resonance. Other conventional techniques for determining antibody affinities are known in the art, such as those described by Scatchard et al. (Ann. *N.Y. Acad. Sci. USA* 51:660 (1949)). Binding properties of an antibody to antigens, cells or tissues thereof may generally be determined and assessed using immunodetection methods including, for example, immunofluorescence-based assays, such as immuno-histochemistry (IHC), and/or fluorescence-activated cell sorting (FACS).

In exemplary embodiments, antibodies of the present invention bind to CLPTM1L with a dissociation equilibrium constant $(K_D)$ of less than approximately $10^{-7}$ M, such as approximately less than $10^{-8}$ M, $10^{-9}$ M, or $10^{-10}$ M, or lower.

Table 1 presents amino acid sequences of epitopes useful for producing CLPTM1L-targeted monoclonal antibodies. The "start" and "end" positions are numbered relative to numbered relative to the amino acid sequence of human CLPTM1L set forth as SEQ ID NO:2 (UniProt ID: Q96AK5-1).

TABLE 1

Peptides and Epitopes For Monoclonal Antibody Production

| Start position | End position | Epitope sequences | SEQ ID NO: |
|---|---|---|---|
| 49 | 60 | RRPKLQLSVYTT | 4 |
| 68 | 79 | ENNIDLVLNVED | 5 |
| 78 | 89 | EDFDVESKFERT | 6 |
| 112 | 123 | HAGVLPWHDGKQ | 7 |
| 186 | 197 | DGSSLPADVHRY | 8 |
| 195 | 206 | HRYMKIVHQLGKT | 9 |
| 233 | 244 | TELPLTVSYDKV | 10 |
| 263 | 274 | QQFGFSEKDADE | 11 |
| 33 | 42 | TRPCSGDANC | 12 |
| 49 | 60 | RRPKLQLSVYTT | 13 |
| 68 | 78 | ENNIDLVLNVE | 14 |
| 80 | 89 | FDVESKFERT | 15 |
| 112 | 123 | HAGVLPWHDGKQ | 16 |

TABLE 1-continued

Peptides and Epitopes For Monoclonal Antibody
Production

| Start position | End position | Epitope sequences | SEQ ID NO: |
|---|---|---|---|
| 131 | 140 | TTYMVPKPEE | 17 |
| 141 | 150 | INLLTGESDT | 18 |
| 147 | 156 | ESDTQQIEAE | 19 |
| 157 | 167 | KKPTSALDEPV | 20 |
| 186 | 195 | DGSSLPADVH | 21 |
| 195 | 206 | HRYMKMIQLGKT | 22 |
| 235 | 244 | LPLTVSYDKV | 23 |
| 255 | 265 | MQDAVYSLQQF | 24 |
| 266 | 274 | GFSEKDADE | 25 |

As described in greater detail in the Examples section, epitopes presented in the shaded boxes (bold text) of Table 1 were initially selected for monoclonal antibody production using the following criteria: (a) epitopes that reside within the predicted surface-exposed globular domains of CLPTM1L (e.g., residues at positions 32-284); (b) epitopes that avoid predicted glycosylation sites (e.g., residues at positions 91,101, and 229); (c) epitopes that avoid the predicted disordered region (e.g., positions 141-162); and (d) epitopes having amino acid sequences that score highly on the basis of hydrophilicity, folding potential, and antigen presentation.

Monoclonal antibodies can be obtained by hybridoma technology, which is the process of producing hybrid cell lines by fusing an antibody-producing B cell with a myeloma cell that can grow in tissue culture. The resulting hybridoma line produces a monoclonal antibody of a single specificity.

In exemplary embodiments, compositions of the invention comprise human anti-CLPTM1L antibodies. It is known in general that when an antibody derived from a non-human animal, e.g., a mouse antibody, is administered to human, it is recognized as a foreign substance and induces a human antibody against the non-human animal antibody. Accordingly, completely "human" antibodies may be desirable for therapeutic treatment of human patients. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Other methods of human antibody production include expression in transgenic animals, hybridomas, and expression of recombinant protein in cell lines (e.g., bacterial, yeast, mammalian). Affinity maturation may be done resulting in a different amino acid sequence. Human antibodies can also be produced using transgenic mice which are incapable of expressing functional endogenous immunoglobulins, but which can express human immunoglobulin genes. For an overview of this technology for producing human antibodies and human monoclonal antibodies and protocols for producing such antibodies, see, e.g., Lonberg and Huszar, *Int. Rev. Immunol.* 13:65-93 (1995); PCT publications WO 98/24893; WO 92/01047; WO 96/34096; WO 96/33735; European Patent No. 0 598 877; U.S. Pat. Nos. 5,413,923; 5,625, 126; 5,633,425; 5,569,825; 5,661,016; 5,545,806; 5,814,318; 5,885,793; 5,916,771; and 5,939,598, which are incorporated by reference herein in their entireties.

In some cases, the human CLPTM1L-specific antibody of this disclosure is an isolated antibody or an isolated antigen binding fragment thereof capable of binding to human CLPTM1L. In some cases, the human antibody comprises a heavy chain variable region comprising a CDRH1 of SEQ ID NO:36, a CDRH2 of SEQ ID NO:37, and a CDRH3 of SEQ ID NO: 38; and a light chain variable region comprising a CDRL1 of SEQ ID NO:39, a CDRL2 of SEQ ID NO:40, and a CDRL3 of SEQ ID NO:41.

In another embodiment, the human antibody comprises a heavy chain variable region comprising a CDRH1 of SEQ ID NO:42, a CDRH2 of SEQ ID NO:43, and a CDRH3 of SEQ ID NO: 44; and a light chain variable region comprising a CDRL1 of SEQ ID NO:45, a CDRL2 of SEQ ID NO:46, and a CDRL3 of SEQ ID NO:47.

In another embodiment, the human antibody comprises a heavy chain variable region comprising a CDRH1 of SEQ ID NO:48, a CDRH2 of SEQ ID NO:49, and a CDRH3 of SEQ ID NO: 50; and a light chain variable region comprising a CDRL1 of SEQ ID NO:51, a CDRL2 of SEQ ID NO:52, and a CDRL3 of SEQ ID NO:53.

In another embodiment, the human antibody comprises a heavy chain variable region comprising a CDRH1 of SEQ ID NO:54, a CDRH2 of SEQ ID NO:55, and a CDRH3 of SEQ ID NO: 56; and a light chain variable region comprising a CDRL1 of SEQ ID NO:57, a CDRL2 of SEQ ID NO:58, and a CDRL3 of SEQ ID NO:59.

In another embodiment, the human antibody comprises a heavy chain variable region comprising a CDRH1 of SEQ ID NO:60, a CDRH2 of SEQ ID NO:61, and a CDRH3 of SEQ ID NO: 62; and a light chain variable region comprising a CDRL1 of SEQ ID NO:63, a CDRL2 of SEQ ID NO:64, and a CDRL3 of SEQ ID NO:65.

In one embodiment, the isolated antibody or antigen-binding fragment thereof comprises, consists essentially of or consists of a light chain comprising SEQ ID NO:27 or a sequence with at least 85-100% sequence identity to SEQ ID NO:27, and a heavy chain comprising SEQ ID NO:26 or a sequence with at least 85% to 100% sequence identity to SEQ ID NO: 26.

In another embodiment, the isolated antibody or antigen-binding fragment thereof comprises, consists essentially of or consists of a light chain comprising SEQ ID NO:29 or a sequence with at least 85-100% sequence identity to SEQ ID NO:29, and a heavy chain comprising SEQ ID NO:28 or a sequence with at least 85% to 100% sequence identity to SEQ ID NO: 28.

In another embodiment, the isolated antibody or antigen-binding fragment thereof comprises, consists essentially of or consists of a light chain comprising SEQ ID NO:31 or a sequence with at least 85-100% sequence identity to SEQ ID NO:31, and a heavy chain comprising SEQ ID NO:30 or a sequence with at least 85% to 100% sequence identity to SEQ ID NO: 30.

In another embodiment, the isolated antibody or antigen-binding fragment thereof comprises, consists essentially of or consists of a light chain comprising SEQ ID NO:33 or a sequence with at least 85-100% sequence identity to SEQ ID NO:33, and a heavy chain comprising SEQ ID NO:32 or a sequence with at least 85% to 100% sequence identity to SEQ ID NO: 32.

In another embodiment, the isolated antibody or antigen-binding fragment thereof comprises, consists essentially of or consists of a light chain comprising SEQ ID NO:35 or a sequence with at least 85-100% sequence identity to SEQ ID NO:35, and a heavy chain comprising SEQ ID NO:34 or a sequence with at least 85% to 100% sequence identity to SEQ ID NO: 34.

In some cases, compositions of the invention include a CLPTM1L-specific antibody modified as an immunoconjugate. As used herein, the term "immunoconjugate" refers to a therapeutic agent that comprises (1) an antibody that binds to an antigen (e.g., a cancer cell antigen) with high specificity, (2) an effector molecule, and (3) a linker. The effector molecule can be selected from the group consisting of therapeutic agents, prodrugs, peptides, proteins, enzymes, viruses, lipids, biological response modifiers, pharmaceutical agents, and polyethylene glycol (PEG). Preferably, the effector molecule has anti-cancer cell activity. See, e.g., Smaglo et al., *Nat. Rev. Clin. Oncol.* 11 (11): 637-48 (2014). Appropriate linkers include, without limitation, can be a thioester bond, a disulfide bond, a hydrazone bond, or a peptide. Preferably, the linker operates to ensure that the effector does not separate from the antibody during transit and will reliably release the effector to a targeted cancer cell or tumor stroma. See, for review, Smaglo et al., *Nature Reviews Clin. Oncol.* 11:637-48 (2014). Without being bound by any particular mechanism or mode of action, it is believed that immunoconguates are particularly effective anticancer agents because they possess the potent anticancer effects of a therapeutic agent (e.g., chemotherapeutic) as well as the highly specific cancer targeting properties of a cancer cell antigen-specific monoclonal antibody. In exemplary embodiments, immunoconjugates of the present invention comprise a therapeutic agent selected from a pharmacologic agent, radioisotope, and toxin; a CLPTM1L-specific monoclonal or polyclonal antibody moiety; and a linker.

In some cases, a CLPTM1L-specific immunoglobulin of the present invention is a bispecific monoclonal antibody (BsMAb, BsAb). As used herein, the terms "bispecific monoclonal antibody," "BsMAb," and "BsAb" are used interchangeably and refer to an engineered immunoglobulin comprising two different monoclonal antibodies or fragments thereof. Accordingly, bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. For example, a BsMAb can be engineered to simultaneously bind an immune cell (e.g., a T cell, a B cell, a monocyte, a macrophage, a neutrophil, a dendritic cell, a phagocyte, a natural killer cell, an eosinophil, a basophil, a mast cell) and a cancer cell antigen (e.g., CLPTM1L) to target and kill the cancer cell. In such cases, a bispecific antibody of this disclosure is an immunotherapeutic. In other cases, bispecific antibodies are configured to otherwise engage immune cells and for other therapeutic modalities.

In some embodiments, a composition provided herein comprises a CLPTM1L-specific immunoglobulin (e.g., polyclonal or monoclonal antibody) that is chemically or structurally modified, conjugated chimerized, humanized, or otherwise engineered antibody. The term "humanized antibody" or "humanized immunoglobulin" refers to an immunoglobulin comprising a human framework, at least one and preferably all complementarity determining regions (CDRs) from a non-human antibody, and in which any constant region present is substantially identical to a human immunoglobulin constant region, i.e., at least about 85-90%, and preferably at least 95% identical. Hence, all parts of a humanized immunoglobulin, except possibly the CDRs, are substantially identical to corresponding parts of one or more native human immunoglobulin sequences. Accordingly, such humanized antibodies are chimeric antibodies (U.S. Pat. No. 4,816,567), wherein substantially less than an intact human variable domain has been substituted by the corresponding sequence from a non-human species. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. Nos. 5,530,101; 5,585,089; 5,693,761; 5,693,762; 6,180,370 (each of which is incorporated by reference in its entirety). Antibodies can be humanized using a variety of techniques known in the art including, for example, CDR-grafting (EP 239,400; PCT publication WO 91/09967; U.S. Pat. Nos. 5,225,539; 5,530, 101 and 5,585,089), veneering or resurfacing (EP 592, 106; EP 519,596; Padlan, Mol. Immunol., 28:489-498 (1991); Studnicka et al., *Prot. Eng.* 7:805-814 (1994); Roguska et al., *Proc. Natl. Acad. Sci.* 91:969-973 (1994), and chain shuffling (U.S. Pat. No. 5,565,332).

An antibody of the invention (e.g., a bispecific antibody) can further comprise a human or a humanized Fc fragment such as a human IgG Fc fragment. CLPTM1L-specific immunoglobulins can be humanized or subjected to Fc modification according to any appropriate methodology. As described herein, the term "humanized antibody" generally refers to a human antibody that has one or more amino acid residues introduced into it from a source that is non-human. These non-human amino acid residues are often referred to as "import" residues, which are typically taken from an "import" variable domain. Accordingly, humanized antibodies are chimeric antibodies (U.S. Pat. No. 4,816,567) where substantially less than an intact human variable domain has been substituted by the corresponding sequence from a non-human species. Bispecific antibodies can be prepared as full-length antibodies or antibody fragments (e.g., F(ab')$_2$ bispecific antibodies). WO 96/16673 describes a bispecific anti-ErbB2/anti-FcγRIII antibody and U.S. Pat. No. 5,837, 234 discloses a bispecific anti-ErbB2/anti-FcγRI antibody. A bispecific anti-ErbB2/Fcα antibody is shown in WO98/ 02463. U.S. Pat. No. 5,821,337 teaches a bispecific anti-ErbB2/anti-CD3 antibody. Traditional production of full-length bispecific antibodies is based on the co-expression of two immunoglobulin heavy chain-light chain pairs, where the two chains have different specificities (Millstein et al., *Nature,* 305:537-539 (1983)).

As used herein, the term "Fc" fragment refers to the carboxy-terminal portions of two heavy (H) chains held together by disulfide bonds. The effector functions of antibodies are determined by sequences in the Fc region, which region is also the part recognized by Fc receptors (FcR) found on certain types of cells. Fc regions can be modified to improve or reduce binding to effector reions. See, e.g., Vincent and Zurini, *Biotechnol. J.* 7(12):1444-50 (2012). Other examples of Fc engineering include modifying the half-life of immunoglobulin G (IgG). For example, antibody fragments having an increased in vivo half-life comprising a salvage receptor binding epitope residues are described in U.S. Pat. No. 5,869,046. Furthermore, engineered pH-dependent antigen binding can be applied to enhance the recycling of IgG via FcRn, enabling binding to additional target molecules. For review, see Kaneko and Niwa, *Biodrugs* 25(1):1-11 (2011). Other techniques for the production of antibody fragments will be apparent to the skilled practitioner.

Without being bound by any particular mechanism or mode of action, it is believed that bispecific monoclonal antibodies exhibit increased antibody-dependent cell-mediated cytotoxicity (Chames et al., *mAbs* 1:6, 539-547 (2009)). Accordingly, an effective dose of a CLPTM1L-targeted bispecific monoclonal antibody of the present invention can be lower than the effective dose of a conventional monoclonal CLPTM1L-specific antibody. In some cases, an effective dose of such a bispecific antibody is one or more orders of magnitude lower than that of a conventional monoclonal antibody. For example, an effective dose of a CLPTM1L-targeted bispecific monoclonal antibody can be around 0.01 mg m$^{-2}$·d$^{-1}$ (milligrams per square meter body surface area per day).

Bispecific antibodies may also be used to localize cytotoxic agents to cancer cells. These antibodies possess a cancer/tumor-binding arm and an arm that binds a cytotoxic agent (e.g., saporin, anti-interferon-α, vinca alkaloid, ricin A chain, methotrexate, or radioactive isotope hapten).

Bispecific antibodies also include antibodies having more than two valencies. For example, bispecific antibodies include trifunctional hybrid antibodies which, as used herein, are antibodies capable of inducing antibody-mediated cytotoxicity (via interactions with tumor-associated antigens on target cancer cells) and T-cell mediated cytotoxicity (via recognition of cytotoxic T lymphocytes) as well as anti-tumor immunologic memory (via interactions of a Fc region with markers on accessory cells such as macrophages). See Tutt et al., *J. Immunol.* 147: 60 (1991). For example, bi- and tri-specific antibodies against CD16, CD19, and CD22 have been shown to activate natural killer cell activation against B-cell leukemia (Gleason et al., *Mol. Cancer. Ther.* 11(12):2674-84 (2012)).

Tri-specific antibodies (also known as trifunctional hybrid antibodies) comprise light and heavy chains originating from parental mouse IgG2a and rat IgG2b monoclonal antibodies, each having different antigen binding properties that provide additive tumor killing capabilities through the efficient recruitment of macrophages and NK cells and efficient co-stimulation of T cells through direct contact with accessory cells such as macrophages. By forming a tri-cell complex comprising a tumor cell, T cell, and accessory cell, trifunctional hybrid antibodies induce coordinated signaling events required for efficient tumor cell destruction. Among those coordinated signaling events are immune effector mechanisms regulating destructive processes such as phagocytosis and perforin-mediated necrosis. For example, tri-specific antibodies targeting chorionic embryonic antigen (CEA) and the T-cell co-receptors CD3 and CD28 have been shown to recruit T lymphocytes to kill CEA positive tumors (Wang et al., *J Biochem.* 135(4):555-65 (2004)).

In some embodiments, antibodies of the invention are modified with respect to effector function, e.g., so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and ADCC. See Caron et al., *J. Exp Med.* 176:1191-1195 (1992). Homodimeric antibodies with enhanced anti-infection activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989).

In other cases, a CLPTM1L-specific antibody of the present invention is embodied in a chimeric antigen receptor T cell. As used herein, the term "chimeric antigen receptor T cell" refers to a genetically engineered antibody-T cell chimera that comprises a chimeric antigen receptor (CAR). As described herein, chimeric antigen receptor T cells of the present invention are therapeutic agents having the antigen specificity of a CLPTM1L-specific antibody and the polyfunctionality and potency of cellular immunity. Techniques for chimeric antigen receptor T cell therapies are known and available in the art. See, e.g., Kenderian et al., *Cancer Res.* 74(22):6383-9 (2014).

In exemplary embodiments, CLPTM1L-specific immunoglobulins provided herein are modified to possess altered binding properties or increased affinity to the target antigen by, for example, affinity improvement or affinity maturation. As used herein, the term "affinity-matured antibody" refers to an antibody or a fragment thereof with one or more amino acid substitutions in a variable region, which results in improved affinity of the antibody for an antigen, as compared to a parent (starting) antibody which does not possess those substitutions. Antibody affinity enhancement techniques are known and available in the art. For example, random mutagenesis (Groves et al., *J. Immunol. Methods,* 313:129-39, 2006) and site-directed mutagenesis methods (Barbas et al., *Proc. Natl. Acad. Sci. USA,* 91:3809-13, 1994) are known. In some cases, these mutagenesis methods are combined with, for example, in vitro display-based technologies such as phage or ribosome display to generate libraries of variants for subsequent screens (Almagro and Strohl, Antibody Engineering: Humanization, Affinity Maturation and Selection Methods. 307-327. In: Therapeutic Monoclonal Antibodies: From Bench to Clinic. Ed. Zhiqiang An. John Wiley & Sons, Inc. 2009). Preferably, a modified antibody obtained by affinity improvement or affinity maturation as described herein will exhibit 2-fold, 5-fold, 10-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 10000-fold or more improved activity for the target antigen compared to a starting antibody. For example, Kaneko and Zurini review optimizing therapeutic antibodies.

In some cases, an immunoglobulin of the invention specifically targets a CLPTM1L polypeptide having one or more mutations. Frameshift and missense mutations of CLPTM1L polypeptides that may be targeted may include, but are not limited to, those set forth in Table 2. The amino acid residue positions are numbered relative to the amino acid sequence of human CLPTM1L set forth as SEQ ID NO:2. Nucleotide positions for coding sequence mutations are numbered relative to the nucleotide sequence of human CLPTM1L set forth as SEQ ID NO:1. Somatic CLPTM1L mutations have been found in tumors of the autonomic ganglia, breast, central nervous system, endometrium, kidney, large intestine, liver, lung, ovary, prostate, skin, stomach, and upper respiratory tract. Each of the known CLPTM1L mutations is rare (<3% of tumors tested), and the functional effects of these mutations are unknown.

TABLE 2

Known Frameshift and Missense Mutations in Human Tumors.

| Position | CDS Mutation | AA Mutation | Type |
|---|---|---|---|
| 206 | c.616delA | p.T206fs*17 | Deletion-Frameshift |
| 61 | c.181A > G | p.T61A | Substitution-Missense |
| 72 | c.214G > A | p.D72N | Substitution-Missense |
| 74 | c.221T > C | p.V74A | Substitution-Missense |
| 105 | c.313T > C | p.Y105H | Substitution-Missense |
| 108 | c.323T > A | p.I108N | Substitution-Missense |
| 110 | c.329T > C | p.L110P | Substitution-Missense |
| 113 | c.338C > A | p.A113D | Substitution-Missense |
| 132 | c.394A > G | p.T132A | Substitution-Missense |
| 151 | c.452A > C | p.Q151P | Substitution-Missense |
| 159 | c.476C > T | p.P159L | Substitution-Missense |
| 175 | c.524C > T | p.A175V | Substitution-Missense |
| 196 | c.586C > T | p.R196W | Substitution-Missense |
| 196 | c.587G > A | p.R196Q | Substitution-Missense |
| 216 | c.646G > A | p.D216N | Substitution-Missense |
| 221 | c.661C > T | p.R221C | Substitution-Missense |
| 250 | c.749G > A | p.R250H | Substitution-Missense |
| 266 | c.796G > A | p.G266R | Substitution-Missense |
| 313 | c.939G > T | p.K313N | Substitution-Missense |
| 319 | c.957C > G | p.I319M | Substitution-Missense |
| 320 | c.959G > A | p.G320D | Substitution-Missense |
| 322 | c.965C > T | p.S322F | Substitution-Missense |
| 353 | c.1058C > T | p.A353V | Substitution-Missense |
| 377 | c.1128_1129CC > AA | p.L377M | Substitution-Missense |
| 390 | c.1168G > A | p.E390K | Substitution-Missense |
| 396 | c.1187A > G | p.Y396C | Substitution-Missense |
| 400 | c.1198G > T | p.A400S | Substitution-Missense |
| 405 | c.1214C > T | p.S405L | Substitution-Missense |
| 430 | c.1289C > A | p.S430Y | Substitution-Missense |
| 431 | c.1291T > C | p.W431R | Substitution-Missense |
| 465 | c.1394C > T | p.P465L | Substitution-Missense |
| 490 | c.1469C > T | p.T490M | Substitution-Missense |
| 493 | c.1477C > T | p.R493W | Substitution-Missense |
| 498 | c.1493G > A | p.R498Q | Substitution-Missense |
| 500 | c.1498G > A | p.D500N | Substitution-Missense |
| 517 | c.1550A > G | p.K517R | Substitution-Missense |
| 529 | c.1587G > C | p.E529D | Substitution-Missense |
| 532 | c.1595C > T | p.T532M | Substitution-Missense |
| 533 | c.1597C > T | p.R533W | Substitution-Missense |
| 538 | c.1612G > A | p.D538N | Substitution-Missense |

* CDS = coding sequence

In another aspect, the present invention provides a nanoparticle conjugated to one or more CLPTM1L-specific immunoglobulins. Generally, antibody-conjugated nanoparticles are able bind to targets with high affinity and cross biological barriers (e.g., blood-brain barrier (BBB)) and, therefore, are advantageous for molecular and cellular targeting. Accordingly, an antibody-conjugated nanoparticle provided herein is useful for a variety of biomedical applications such as in vivo diagnosis, in vivo imaging (e.g., theranostic imaging or diagnostic imaging with dye- and Ab-conjugated nanoparticles), clinical therapies, targeted drug delivery, targeted delivery of other cargo, gene therapy, cell labeling/tracking, and molecular imaging. In some cases, antibody-conjugated nanoparticles are particularly advantageous for diagnostic, theranostic imaging, and other imaging applications. In some cases, nanoparticles of the present invention are semiconductor nanocrystals (e.g., nanodots), lipid-based vehicles (e.g., liposomes, solid lipid nanoparticles, micelles); polymer carriers, such as hydrogels, polymersomes, dendrimers, and nanofibers; metallic nanoparticles (e.g., gold, silver, titanium); carbon structures (e.g., nanotubes, nanohorns, nanodiamonds (NDs), grapheme); or inorganic particles (e.g., silica). See, e.g., Chow and Ho, *Sci Transl Med* 5:216rv4 (2013); Montenegro et al., *Adv.*

*Drug Delivery Rev.* 65:677-688 (2013). A number of various semiconductor nanocrystals (i.e., nanodots) can be selected.

In a further aspect, the present invention provides compositions comprising an immunoglobulin that targets a CLPTM1L polypeptide and at least one pharmaceutically acceptable carrier, diluent, or excipient. As used herein, the phrase "pharmaceutically acceptable" refers to those agents, compounds, materials, compositions, and/or dosage forms which are, within the scope of sound medical judgment, suitable for use in contact with the tissues of humans and animals without excessive toxicity, irritation, allergic response, or other problems or complications, commensurate with a reasonable benefit/risk ratio.

In another aspect, compositions of the present invention include peptides comprising part of the CLPTM1L amino acid sequence. For example, the present invention provides a peptide having the amino acid sequence of SEQ ID NO:4, 5, 6, 7, 8, 9, 10, 11, 12, 13, 14, 15, 16, 17, 18, 19, 20, 21, 22, 23, 24, or 25 (see Table 1). Additional CLPTM1L peptides of the present invention include peptides selected according to the above-defined epitope properties. Peptides may represent 8-22 amino acid length portions of SEQ ID NO:2. In some cases, a CLPTM1L peptide may be embodied as a therapeutic agent. For example, a CLPTM1L peptide can be embodied in a peptide vaccine, a ligand blocking peptide, or a competitive inhibitory peptide. Such agents are expected to be useful therapeutic agents for treating or preventing lung cancer. Peptide vaccines are particularly amenable to prophylactic approaches. It is further expected that a CLPTM1L epitope, a CLPTM1L immunoglobulin, or any other CLPTM1L-targeting therapeutic agent will be useful in the treatment or prevention of many cancer types including, without limitation, lung, cervical, myeloblastic leukemia, pancreatic, bladder, glioma, prostate, basal cell carcinoma, and melanoma.

In some cases, a composition of the present invention is an aptamer having specificity for a CLPTM1L target molecule. As used herein, the term "aptamer" refers to a structured oligonucleotide-based or peptide-based molecule having high affinity and specificity for a specific target molecule (e.g., proteins, phospholipids, iron channels, nucleic acids, whole cells) due to unique structural features that restrict the aptamer to particular conformations. Oligonucleotide aptamers such as ribonucleic acid (RNA) and single-strand deoxyribonucleic acid (ssDNA) aptamers. Peptide aptamers are combinatorial protein molecules that comprise a short peptide region attached at both ends to a protein scaffold. Methods for designing and identifying therapeutic aptamers having high affinity and specificity for a CLPTM1L target molecule are known in the art. See, e.g., Rohloff et al., *Molecular Therapy Nucleic Acids* 3:e201 (2014); Zhu et al., *Theranostics* 4(9):931-944 (2014); Ellington and Szostak, *Nature* 346:818-822 (1990).

Compositions provided herein can comprise at least one pharmaceutically acceptable diluent, excipient, or carrier. As used herein, "pharmaceutically acceptable carrier" refers to any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

Regardless of the route of administration selected, therapeutic agents of the present invention, which may be used in a suitable hydrated form, and/or the pharmaceutical compositions of the present invention, can be formulated into pharmaceutically acceptable dosage forms by conventional methods known to those of skill in the art.

In certain embodiments, a pharmaceutical composition provided herein comprises one or more CLPTM1L-targeting agents, a chemotherapeutic agent, and a pharmaceutically acceptable carrier. Chemotherapeutic agents include, without limitation, platinum-based agents, such as cisplatin, gemcitabine, and carboplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon.alpha., and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

In other embodiments, compositions of the invention provided herein can additionally comprise one or more other biologically active substances including, without limitation, therapeutic drugs or pro-drugs such as chemotherapeutic agents other than those identified above, scavenger compounds, antibiotics, antiviral agents, antifungal agents, anti-inflammatory agents, vasoconstrictors and anticoagulants, antigens useful for cancer vaccine applications or corresponding pro-drugs.

Methods of Using Compositions of the Invention

In one aspect, the present invention is directed to methods of treating or preventing a disease or condition in a subject by inhibiting CLPTM1L. For example, the present invention provides methods comprising administering to a subject in need thereof an immunoglobulin or a composition comprising an immunoglobulin that targets and specifically binds to CLPTM1L. As used herein, the term "subject" refers to an individual having, suspected of having, or susceptible to having a disease or condition associated with CLPTM1L protein dysfunction (e.g., pathogenic production, modification, or function) or for which there is a genetic association with CLPTM1L (e.g., a disease or condition associated with a gain in CLPTM1L locus copy number or a genotype for susceptibility to the disease or disorder). By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, the terms "treating," "treat," and "treatment" refer to the management and care of a patient for the purpose of combating the disease, condition, or disorder. The terms embrace both preventative, i.e., prophylactic, and palliative treatments. In some cases, the term "treated" refers to any beneficial effect on progression of a disease or condition. Beneficial effects can include reversing, alleviating, inhibiting the progress of, preventing, or reducing the likelihood of the disease or condition to which the term applies or one or more symptoms or manifestations of such a disease or condition. Where the disease or condition is a tumor, cancer, or cancer-associated condition, treating can refer to the management and care of a patient for the purpose of combating cancer, and can include reversing, alleviating, inhibiting the progress of, preventing, reducing the size of, or reducing the likelihood of, or lessening the severity of any aspect of the cancer or cancer-associated condition (e.g., metastasis, tumor growth). A therapeutic beneficial effect on the health and well-being of a patient includes, but it not limited to: (1) curing the cancer; (2) slowing the progress of the cancer; (3) causing the tumor to regress; or (4) alleviating one or more symptoms of the cancer. As used herein, the terms "preventing" and "prevent" refer not only to a complete prevention of a certain disease or condition, but also to partially or substantially attenuating, reducing the risk of, or delaying the development or recurrence of the disease or condition to which the term applies.

In some cases the methods provided herein are directed to treating or preventing a tumor cancer in a subject by administering a composition provided herein. In an exemplary embodiment, the method treats or prevent a solid tumor in the subject receiving administration of a composition comprising a CLPTM1L-targeting agent to a subject in need thereof. As used herein, the term "cancer" includes, without limitation, solid tumors and blood-borne tumors (e.g., leukemias). The term cancer includes, without limitation, diseases of the skin, tissues, organs, bone, cartilage, blood, and vessels. The term further encompasses both primary and metastatic cancers. In some cases, therefore, methods of treating or preventing cancer as provided by the present invention include methods of inhibiting, retarding, or preventing growth of a tumor or tumor cells. A subject in need thereof may include, for example, a subject who has been diagnosed with a tumor, including a pre-cancerous tumor, a cancer (e.g., a non-small cell lung cancer), or a subject who has been treated, including subjects that have been refractory to previous treatment.

In some cases, solid tumors appropriate for the present invention are considered to be a "refractory" or "resistant" solid tumor, meaning that the solid tumor does not respond to treatment. The tumor may be resistant at the outset of treatment or it may develop resistance during treatment. While any and all tumors that are susceptible to treatment and/or prophylactic administration of a CLPTM1L-targeting agent described herein are of course within the scope of this invention, it is anticipated that the compositions and methods provided herein will be particularly useful in the treatment of refractory tumors.

The methods provided herein are appropriate for treating or preventing any type of disease or condition associated with CLPTM1L protein dysfunction (e.g., pathogenic production, modification, or function) or any disease or condition for which there is a genetic association with CLPTM1L (e.g., a disease or condition associated with a gain in CLPTM1L locus copy number or a genotype for susceptibility to the disease or disorder). In an exemplary embodiment, a method provided herein is for the treatment or prevention of a cancer, a tumor (e.g., a solid tumor), or a pre-neoplastic lesion (e.g., pre-cancerous lesion). Examples of cancers appropriate for methods of treating or preventing as provided herein include, without limitation, lung cancer, pancreatic cancer, prostate cancer, skin cancer, bladder cancer, kidney cancer, ovarian cancer, colon cancer, colorectal cancer, breast cancer, cervical cancer, brain cancer, esophageal cancer, and stomach cancer. Solid tumors can be associated with cancers and pre-neoplastic lesions of the lung, pancreas, prostate, breast, kidney, and other sarcomas, carcinomas, and glioblastomas. Other diseases or conditions appropriate for methods of treating or preventing as provided herein include, without limitation, lymphomas, chronic leukemia, and acute leukemia.

In some cases, a method provided herein can be practiced to treat or prevent a disease or condition in a subject, where the disease or condition exhibits chemotherapeutic drug resistance. For example, a subject can be diagnosed or identified as having a disease or condition such as cancer that exhibits resistance to a chemotherapeutic agent such as cisplatin or gemcitabine. CLPTM1L has been found to be highly expressed in cisplatin resistant ovarian tumor cell lines. Moreover, CLPTM1L appears to be anti-apoptotic under genotoxic conditions. Examples of cancers for which treatment involves administering cisplatin include lung cancer, colorectal cancer, non-small cell lung cancer (NSCLC), bronchioloalviolar cell lung cancer, bone cancer, pancreatic cancer, skin cancer, cancer of the head or neck, cutaneous melanoma, intraocular melanoma, uterine cancer, ovarian cancer, rectal cancer, anal region cancer, stomach cancer, gastric cancer, colon cancer, breast cancer, uterine cancer, fallopian tube carcinoma, endometrial carcinoma, cervical carcinoma, Hodgkin's Disease, esophagus cancer, small intestine cancer, endocrine system cancer, thyroid gland cancer, parathyroid gland cancer, adrenal gland cancer, soft tissue sarcoma, prostate cancer, bladder cancer, kidney cancer, renal cell carcinoma, renal pelvis carcinoma, mesothelioma, hepatocellular cancer, biliary cancer, chronic leukemia, acute leukemia, lymphocytic lymphoma, CNS neoplasm, spinal axis cancer, brain stem glioma, glioblastoma multiforme, astrocytoma, schwannoma, ependymoma, medulloblastoma, meningioma, squamous cell carcinoma and pituitary adenoma tumors or tumor metastases.

In some cases, a method provided herein can be practiced to treat or prevent a cancer associated with a mutation, translocation, amplification, or deletion of at least a portion of at least one of the following: K-Ras, H-Ras, N-Ras, RASSFI, PI3KCA, PTEN, EGFR, FGFR1, PDGFRA, BRAF, AKL, ROS1, BCL-x, BIM, BAD, BAX, AKT, and mTOR. In an exemplary embodiment, a method provided herein can be practiced to treat or prevent a cancer for which at least one of these genes suspected of being or demonstrated to be regulated by CLPTM1L.

In some cases, a method provided herein can be practiced to treat or prevent a cancer previously or currently being subjected to radiation therapy. As used herein, the term "radiation therapy" refers to any manner of treatment of solid tumors and cancers with ionizing radiation and includes, without limitation, external beam radiotherapy, stereotatic radiotherapy, virtual simulation, 3-dimensional conformal radiotherapy, intensity-modulated radiotherapy, ionizing particle therapy, and radioisotope therapy.

In other cases, a method provided herein can be practiced to treat or prevent a cancer previously or currently being subjected to chemotherapy using a chemotherapeutic agent such as, for example, an alkylating agent, a cross-linking agent, an anti-metabolite, an antibiotic, a topoisomerase inhibitor, or a mitotic inhibitor. As used herein, the term "chemotherapeutic agent" refers to any substance that, when administered in a therapeutically effective amount to a patient suffering from a tumor or cancer, has a therapeutic beneficial effect on the health and well-being of the patient. A therapeutic beneficial effect on the health and well-being of a patient includes, but it not limited to: (1) curing the cancer; (2) slowing the progress of the cancer; (3) causing the tumor to regress; or (4) alleviating one or more symptoms of the cancer. As used herein, a chemotherapeutic agent also includes any substance that, when administered in a prophylactic amount to a patient afflicted with a solid tumor or who has been rendered substantially free of cancer as the result of one or more therapeutic treatment regimes, has a beneficial effect on the health and well-being of the patient.

The method also can be practiced to treat or prevent a cancer if use of such a therapeutic agent is anticipated. For example, methods provided herein are useful to treat or prevent a cancer for which targeting CLPTM1L sensitizes the cancer cells to DNA damage-induced apoptosis. As used herein, the terms "sensitize" and "sensitized" refers to cells made more responsive to an agent, a treatment, an environment, a stimulus, or a condition. For example, a "sensitized" cell can exhibit an increase in the magnitude of said response or an increase in any type of response. In an exemplary embodiment, cancer cells exhibit increased apoptosis when sensitized to DNA damage by targeting CLPTM1L according to a method provided herein. As described in the Examples that follow, the inventor has demonstrated that monoclonal antibodies (mAbs) targeting CLPTM1L chemosensitize pancreatic tumor cells to treatment with chemotherapeutic agents such as gemcitabine. As used herein, the term "chemosensitize" refers to cells made more responsive to a chemotherapeutic agent.

In another aspect, provided herein are methods for treating or preventing cancer by administering a CLPTM1L-targeting agent that acts synergistically to kill tumor cells. As described in the Examples that follow, CLPTM1L-targeting agents synergize with chemotherapeutic agents such as cisplatin and carboplatin, thus potentiating the therapeutic activity of such chemotherapeutics. The method can comprise administering a CLPTM1L-targeting agent in a chemosensitizing effective amount to a subject in need thereof. As used herein the phrase "chemosensitizing effective amount" means that dose and dosing schedule which results in an enhanced toxicity by a chemotherapeutic agent, without adverse side effects. The specific dose will vary depending on the particular CLPTM1L-targeting agent used, the dosing regimen to be followed, and the particular chemotherapeutic agent with which it is administered. Such a daily dose can be determined without undue experimentation by methods known in the art or as described herein. Preferably, CLPTM1L-targeting agents act as chemosensitizers to reverse or modulate resistance of a tumor cell to a chemotherapeutic agent. It is therefore advantageous that the chemosensitizing agent and the chemotherapeutic agent would be administered substantially at the same time, in order to allow their combined action by their dual presence in the treated tumor cell.

In addition to synergistic tumor killing effects in monolayer culture, CLPTM1L-target agents can be used to resensitize cisplatin resistant tumor cells to cisplatin killing under anchorage independent conditions (see FIG. 32B). 102-5 anti-CLPTM1L acts in synergy with cisplatin to kill tumor cells as measured by two-way ANOVA (p<0.05) and isobole and combination index (0.65) (FIGS. 13F-13G, 32C-32D). Isobologram analysis evaluates the nature of interaction of two drugs, i.e., drug A and drug B, at a given effect level. Operationally, the concentrations required to produce the given effect (e.g., $IC_{50}$) are determined for drug A (ICx, A) and drug B (ICx, B) and indicated on the x and y axes of a two-coordinate plot, forming the two points (ICx, A, 0) and (0, ICx, B). The line connecting these two points is the line of additivity. Then, the concentrations of A and B contained in combination that provide the same effect, denoted as (CA, x, CB, x), are placed in the same plot. A combination index (CI) is calculated by Eq. 1:

$$CI = CA, x/Cx, A + CB, x/Cx, B \qquad \text{(Eq. 1.)}$$

Synergy, additivity, or antagonism is indicated when (CA, x, CB, x) is located below, on, or above the line, respectively. A leftward shift of combination concentration-effect curves relative to the curves for both of the single agents indicates Loewe synergy and a rightward shift indicates Loewe antagonism. The data presented and described herein demonstrate that CLPTM1L-targeting agents such as CLPTM1L immmunoglobulins (i) sensitize tumor cells to chemotherapeutic killing (as tested with carboplatin, cisplatin, camptothecin, and gemcitabine), (ii) increase sensitivity regardless of acquired resistance in tumor cells, and (iii) inhibit anchorage independent growth regardless of combination treatment.

In some cases, a method provided herein can be practiced to treat or prevent a cancer suspected of being or demonstrated to be refractory to one or more chemotherapeutics such as, for example, an alkylating agent, a cross-linking agent, an anti-metabolite, an antibiotic, a topoisomerase inhibitor, or a mitotic inhibitor. For example, a method provided herein can be appropriate to treat or prevent a cancer for which targeting CLPTM1L using an immunoglobulin sensitizes the cancer cells to cytotoxic treatment with a cross-linking agent and a topoisomerase inhibitor.

In exemplary embodiments, a method of treating or preventing cancer as provided herein comprises administering to a subject in need thereof two or more CLPTM1L-specific immunoglobulins. The two or more CLPTM1L-specific immunoglobulins can be administered simultaneously or sequentially. For example, the method can comprise administering two or more CLPTM1L-specific immunoglobulins, where the immunoglobulins are selected for capacity to increase sensitivity of CLPTM1L-expressing tumor cells to a chemotherapeutic agent (e.g., cisplatin, gemcitabine) and/or for an enhanced capacity for cytotoxicity toward CLPTM1L-expressing tumor cells. The combination can comprise antibodies having specificity to different polypeptides or to different epitopes on the same polypeptide. Such combination therapies have been shown to improve tumor responses and reverse resistance of tumor cells to a single agent. See, e.g., Weiner et al., *Nature Rev. Immunol.* 10:317-327 (2010).

In another aspect, provided herein is a method of treating or preventing cancer in a subject, where the method comprises administering an immunoconjugate. As described herein, immunoconjugates are effective cytotoxic and anti-cancer therapeutic agents.

In a further aspect, provided herein is a method of treating or preventing cancer in a subject, where the method comprises administering activated T cells to a subject in need thereof. Such activated T cell therapy methods generally comprise ex-vivo activation and expansion of T cells. See, for review, Slaney et al., *Cancer Res.* 74:7168-7174 (2014). In some cases, T cells are obtained from a subject, then purified, expanded, and activated ex vivo. Activation comprises culturing purified and expanded T cells in the presence of a cancer cell-specific or tumor specific antigen (e.g., a monoclonal antibody provided herein). The resulting activated T cells are provided back to the subject. T cells activated in this manner have enhanced immunostimulatory capabilities. In exemplary embodiments, T cells obtained from a subject in need of treatment according to a method provided herein are cultured in the presence of one or more CLPTM1L-specific monoclonal antibodies (e.g., mAbs 6-1, 10-2, and 10-3).

Methods of treating or preventing cancer as provided herein can be practiced at any appropriate time. In some cases, a composition comprising a CLPTM1L-targeting agent as provided herein is administered to a subject following diagnosis of a cancer or a pre-neoplastic lesion (e.g., pre-cancerous lesion) in, for example, a biological sample from the subject. In other cases, a composition comprising a CLPTM1L-targeting agent as provided herein is administered to a subject following identification of copy number gain or expression of CLPTM1L in a biological sample from the subject, where the level of expression is above a threshold that is empirically determined to constitute cancer risk.

Determination of such a threshold includes analysis of current and future data correlating CLPTM1L expression in normal tissue with incidence of a cancer. With respect to lung tissue, a threshold that is empirically determined to constitute cancer risk can be at least 2-fold greater average expression for one or more test lung tissue samples relative to the average expression in a healthy sample taken from surrounding tissue. In some cases, treatment may be indicated if it is determined that expression of CLPTM1L is higher in a test sample (e.g., tissue suspected of comprising cancer cells) compared to tissue surrounding the sampled tissue. In other cases, treatment may be indicated if it is determined that an increased amount of CLPTM1L is present on a tumor cell surface. Such an increased level of CLPTM1L can be detected by, for example, flow cytometry in circulating tumor cells or in solid tumors. A composition comprising a CLPTM1L-targeting agent as provided herein can be administered to a subject upon identification of one or more indicators or risk factors for the development of cancer or following identification of a genotype associated with a cancer in a biological sample from the subject. To prevent or slow tumor formation, a composition comprising a CLPTM1L-targeting agent as provided herein is administered to a subject prior to or in the absence of a cancer or pre-neoplastic lesion. In such cases, the composition is administered as a preventative agent.

Treatment or prevention according to a method provided herein can occur before, during, or after the subject is treated by surgery, radiation, and/or chemotherapy. In some cases, treatment according to a method provided herein prior to chemo- or radiotherapy may improve the outcome of the conventional therapy. In an exemplary embodiment, a composition comprising a CLPTM1L-targeting agent as provided herein is administered to a subject concurrently with one or more other treatments or preventative measures such as radiotherapy, chemotherapy, or surgery.

A composition comprising a CLPTM1L-targeting agent as provided herein is administered to a subject by any method that achieves the intended purpose or is deemed appropriate by those of skill in the art. For example, a composition of the present invention can be administered as a pharmaceutical, and may be administered systemically or locally via oral or parenteral administration. As used herein, the term "administration" includes oral and parenteral administration. Oral administration includes, for example, administration of oral agents. Such oral agents include, for example, granules, powders, tablets, capsules, solutions, emulsions, and suspensions. Parenteral administration includes, for example, administration of injections. Such injections include, for example, subcutaneous injections, intramuscular injections, and intraperitoneal injection. In some cases, intravenous injections such as drip infusions, intramuscular injections, intraperitoneal injections, subcutaneous injections, suppositories, enemas, oral enteric tablets, or the like can be selected.

Appropriate modes of administration can be determined based on the physical location of a tumor or tumors in the subject's body. In exemplary embodiments, a composition comprising a CLPTM1L-targeting agent as provided herein is administered to a subject having a diagnosis of lung cancer or a pre-cancerous lesion, where the composition is administered orally or intravenously. Alternatively, a composition comprising a CLPTM1L-targeting agent can be administered locally to an intended area of treatment. For example, a composition comprising a CLPTM1L-targeting agent can be administered by local injection during surgery.

Compositions can be administered to a subject in need thereof in dosage unit form where each discrete dosage unit contains a predetermined quantity of an active ingredient or compound that was calculated to elicit a desirable therapeutic effect when administered with, in some cases, a pharmaceutically acceptable carrier.

A therapeutically effective dose relates to the amount of a compound which is sufficient to improve the symptoms, for example a treatment, healing, prevention or improvement of such conditions. In exemplary embodiments, a therapeutically effective amount or dose is an amount such that free antibody is present in the blood. For dosage determinations, it can be advantageous to assess toxicity and therapeutic efficacy of a compound in cell cultures or in experimental animals. For example, the $LD_{50}$ (i.e., the dose lethal to 50% of the population) and $ED_{50}$ (i.e., the dose therapeutically effective in 50% of the population) can be determined. From these calculations, dosage ranges for use in humans can be formulated. Dosage ranges can vary depending on factors such as mode of administration. A therapeutically effective amount of a pharmaceutical composition provided herein can range from about 0.001 to 100 mg of antibody per kg body weight of the subject (e.g., about 0.01 to 100 mg/kg body weight; about 0.1 to 40 mg/kg body weight; about 1 to 20 mg/kg body weight).

In some cases, an appropriate dose for a monoclonal antibody can be from 0.005 mg/kg up to a maximum tolerated dose. In some cases, an appropriate dose of a pharmaceutical composition as provided herein can be determined according to body surface area of a subject, calculated using the subject's height and weight, to whom the composition will be administered. In such cases, a dose can be provided as a particular amount of the composition per $m^2$ (e.g., mg/$m^2$). In some cases, an appropriate dose can be between approximately 10 mg/$m^2$ and approximately 40 mg/$m^2$ of a monoclonal antibody. When converted to milligrams (mg) per kilogram (kg) of a subject's body weight, a dose of 15 mg/$m^2$ is the same as about 0.4 mg/kg. See Freireich et al., *Cancer Chemotherapy Rep.* 50(4):219-244 (1966). Additional information about dosage calculation can be found in Center for Drug Evaluation and Research, Center for Biologics Evaluation and Research (2002), *Estimating the safe starting dose in clinical trials for therapeutics in adult healthy volunteers*, U.S. Food and Drug Administration, Rockville, Maryland, USA.

It will be understood that mass of pharmaceutical composition comprising a monoclonal antibody as provided herein can refer to mass of the antibody plus a delivery agent or pharmaceutically acceptable carrier, if applicable. In some cases, dosages and dosage ranges appropriate for a composition provided herein can be determined using pharmacokinetic data (i.e., drug metabolism and clearance). As used herein, "pharmacokinetics" refers to the process by which a drug or pharmaceutical composition is absorbed, distributed, metabolized, and excreted from the body.

Clinicians, physicians, and other health care professionals can administer a composition to a subject in need thereof according to a method provided herein by a physician or other health professional. In some cases, a single administration of the composition may be sufficient. In other cases, more than one administration of the composition is performed at various intervals (e.g., once per week, twice per week, daily, monthly) or according to any other appropriate treatment regimen. The duration of treatment can be a single dose or periodic multiple doses for as long as administration of a composition provided herein is tolerated by the subject.

Any appropriate method can be practiced to determine, detect, or monitor a subject's response to treatment according to a method provided herein. As used herein, "determining a subject's response to treatment" refers to the assessment of the results of a therapy in a subject in response to administration of a composition provided herein or to treatment according to a method provided herein. For example, a subject's condition can be monitored continuously or evaluated at appropriate time intervals (e.g., at regular or irregular time points) to detect and/or monitor any changes in disease progression (e.g., change in tumor size) as an indicator of the subject's response to a composition comprising an RNAi-inducing construct targeted to CLPTM1L. In some cases, tumors can be measured to detect or monitor any change in, for example, tumor size or tumor growth rate (e.g., tumor expansion or shrinkage, inhibited or accelerated tumor growth rate). For example, detection methods such as computed tomography (CT), magnetic resonance imaging (MRI) scanning, and x-ray (e.g., chest x-ray) can be used. In some cases, ultrasound examinations can be used to detect and measure tumor regression or to detect progression of lesions. In other cases, evaluation of a tumor or pre-neoplastic lesion can involve cytology or histology of, for example, biopsy samples. For solid tumors, evaluation of a subject's response to treatment as provided herein can include assessing RECIST ("Response Evaluation Criteria in Solid Tumors"). RECIST criteria can be used to evaluate a subject's response to the therapy used to treat their disease or condition. See, for review, Therasse et al., *J. Natl. Cancer Inst.* 92:205-16, 2000.

In some cases, biomarkers (e.g., mRNA, protein) can be used to detect or monitor the efficacy of a treatment or prevention method described herein. In an exemplary embodiment, use of a biomarker can comprises a) administering a composition provided herein; b) determining the levels of a biomarker according to the present invention in one or more biological samples taken from the subject at different time points (before, during and/or after administration); and c) comparing the determinations made for the biological samples obtained during a particular phase of treatment and comparing them to controls or to levels determined for the subject's samples obtained at different phases of treatment. For bone and blood tumors, evaluation using biomarkers can include detecting or monitoring expression levels for one or more tumor markers and assessing hematologic indicators including, for example, mean platelet volume, platelet counts, leukocyte counts, and hemoglobin level. Other indicators or "efficacy markers" of a positive outcome following administration of a composition comprising a CLPTM1L-specific agent according to a method provided herein can include (1) reduced CLPTM1L transcript and/or protein levels in tumors or target tissues and (2) reduced phosphorylated Akt or Bcl-xL protein levels in tumors or target tissues. These efficacy markers can be determined by biopsy, aspirate, or lavage followed by, in an exemplary embodiment, an appropriate diagnostic test such as PCR, Western blotting, immunohistochemistry using specific antibodies. A positive result for any of the outcome criteria or evaluation methods described herein is indicative of the method's efficacy for treating or preventing the subject's disease or condition.

Indicators of a positive response to administration of a composition comprising a CLPTM1L-targeting agent according to a method provided herein can include, for example, a significant decrease in CLPTM1L transcript and/or CLPTM1L protein levels in tumors or target tissues relative to pre-treatment levels or to untreated samples (e.g., expression reduced to approximately 60%-80% of expression in a control sample). In some cases, an indicator of a positive response to administration of a composition comprising a CLPTM1L-targeting agent can be significantly reduced levels of phosphorylated Akt and/or Bcl-xL proteins in tumors or target tissues relative to pre-treatment levels or to untreated samples or a significant increase in apoptosis in tumors or target tissues relative to pre-treatment levels or to untreated samples. According to RECIST criteria, a partial response to treatment can be indicated by at least a 30% decrease in the sum of the longest diameter of a target lesions, taking as reference the baseline sum longest diameter, and a complete or substantially complete response to treatment can be indicated by the complete or nearly complete disappearance of all target lesions relative to measurements obtained for the subject prior to treatment (i.e., baseline measurement) or relative to a control or a comparative decrease in disease progression. In some cases, response to treatment is evaluated relative to one or more subjects who were not administered a composition described herein. Other parameters for evaluating a subject's response to treatment according to a method provided herein include detecting a comparative decrease in metastatic growth; detecting any improvement in RECIST criteria for solid tumors; documenting short-term or long-term survival; documenting disease-free survival; detecting increased or decreased expression of tumor markers; detecting hematologic changes for blood and bone cancers; detecting or monitoring positive or negative responses to radiotherapy and/or chemotherapy; and detecting an increase or decrease in recurrence of the treated disease or condition. In some cases, a subject treated according to a method provided herein may exhibit signs of stable disease, where there is neither sufficient shrinkage to qualify for partial response nor sufficient increase to qualify for progressive disease, taking as reference the smallest sum longest diameter since the treatment started (Therasse et al., supra).

The determination of the response of a subject to a specific therapy can be determined using any assessment criterion used in oncology and known by persons skilled in the art. Assessment parameters useful for describing progression of a disease include: disease-free progression which, as used herein, describes the ratio of subjects in complete remission who have not had disease relapse during the time period under study; objective response, which, as used in the present invention, describes the ratio of subjects treated in whom a complete or partial response is observed; tumor control, which, as used in the present invention, relates to the ratio of people treated in whom a complete response, partial response, minor response or stable disease ≥6 months is observed; progression-free survival which, as used herein, is defined as the time from the beginning of the treatment until the first measurement of cancer growth. In a preferred embodiment, the response of a subject is determined by means of a parameter selected from time to progression and survival. In an exemplary embodiment, a subject's response to a treatment or preventative method provided herein should be statistically significant. The determination of whether a response is statistically significant can be carried out using statistical evaluation tools such as confidence intervals, determination of the p value, Student's t-test, Mann-Whitney test, etc. Preferred confidence intervals are at least 50%, at least 60%, at least 70%, at least 80%, at least 90%, at least 95%. Preferably, p values are 0.2, 0.1, or 0.05.

While the subject is being treated, the health of the subject may be monitored by measuring one or more of the relevant indices at predetermined times during a 24-hour period. All aspects of the treatment, including supplements, amounts, times of administration and formulation, can be optimized based on the results of such monitoring. A patient can be periodically reevaluated to determine the extent of improvement by measuring the same parameters. For example, a first such reevaluation can occur at the end of an appropriate length of time (e.g., about 2 weeks, about 4 weeks, about 8 weeks, or more) following the onset of therapy, and subsequent reevaluations can occur at appropriate intervals (e.g., every four to eight weeks during therapy and then every 3, 6, 9, or more months) thereafter.

The articles "a" and "an" are used herein to refer to one or to more than one (i.e., to at least one) of the grammatical object of the article. By way of example, "an antibody" means one antibody or more than one antibody. As such, the terms "a" (or "an"), "one or more," and "at least one" are used interchangeably herein.

While the present invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents and alternatives falling within the spirit and scope of the invention as defined by the appended claims.

The invention will be more fully understood upon consideration of the following non-limiting Examples.

EXAMPLES

Example 1—Structural Analysis of CLPTM1L

Figures 2A, 2B:
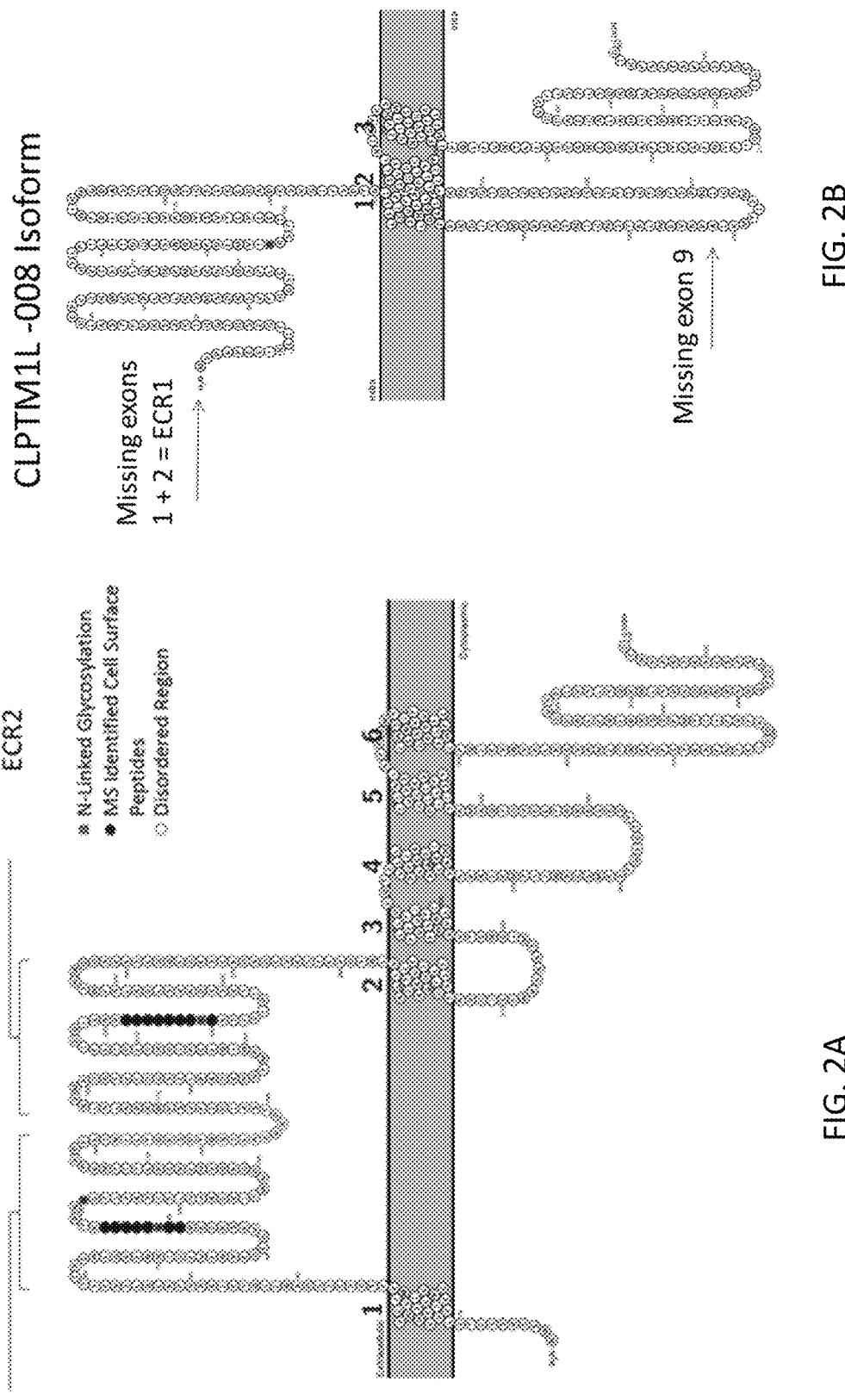
FIGS. 2A-2B present (A) a summary of CLPTM1L predicted structure including orientation of the human sequence (SEQ ID NO:2) of CLPTM1L within the plasma membrane, two extracellular globular domains (ECR1 and ECR2), the interstitial disordered region, transmembrane regions, and identified glycosylated cell surface peptides (in blue) and predicted sites N-glycosylation sites (green). Monoclonal antibodies generated against CLPTM1L peptides targeting each ECR are indicated in parentheses. Image was generated using the Protter application (Omasits et al., *Bioinformatics* 30(6):884-6 (2014)). (B) A splicing variant of CLPTM1L (SEQ ID NO:71), lacking extracellular region 1 and some transmembrane domains changing the predicted structure. The expression pattern of this isoform is not known.

We generated a basic structural model of CLPTM1L that includes six transmembrane domains, extracellular globular domains (ECR1 and ECR2), the disordered region, and N-glycosylated cell-surface peptides identified by mass spectrometry (FIG. 2A). There is a putative alternatively spliced isoform of CLPTM1L lacking ECR1 and exons 1, 2, and 9 (FIG. 2B). Glycosylated (N-linked) amino acid residues are predicted at positions 91, 101, and 229 of the human CLPTM1L protein sequence (SEQ ID NO:2). Mass spectrometry evidence of glycosylation has been reported for amino acid residue 91 of human CLPTM1L (data not shown) and for residue 229 (Chen et al., *J Proteome Res.* 2009; 8:651-61). For a plasma membrane protein, this is highly indicative of extracellular orientation of the glycosylated region. It is predicted that this extracellular region comprises two separate globular domains separated by a small disordered region (amino acid residues 142-162) within the larger extracellular region (FIGS. 1A-1B).

Although our analysis of CLPTM1L suggested the possibility of plasma membrane localization and cell surface exposure, subcellular localization of CLPTM1L had not been well studied and plasma membrane localization was not previously reported. One study suggested that CLPTM1L may be localized to mitochondria. See Ni et al., *PLOS One* 7:e52598, 2012. The potential for CLPTM1L exposure at the surface of tumor cells has significant relevance to the ability to target this protein with exogenous agents.

Figure 3:
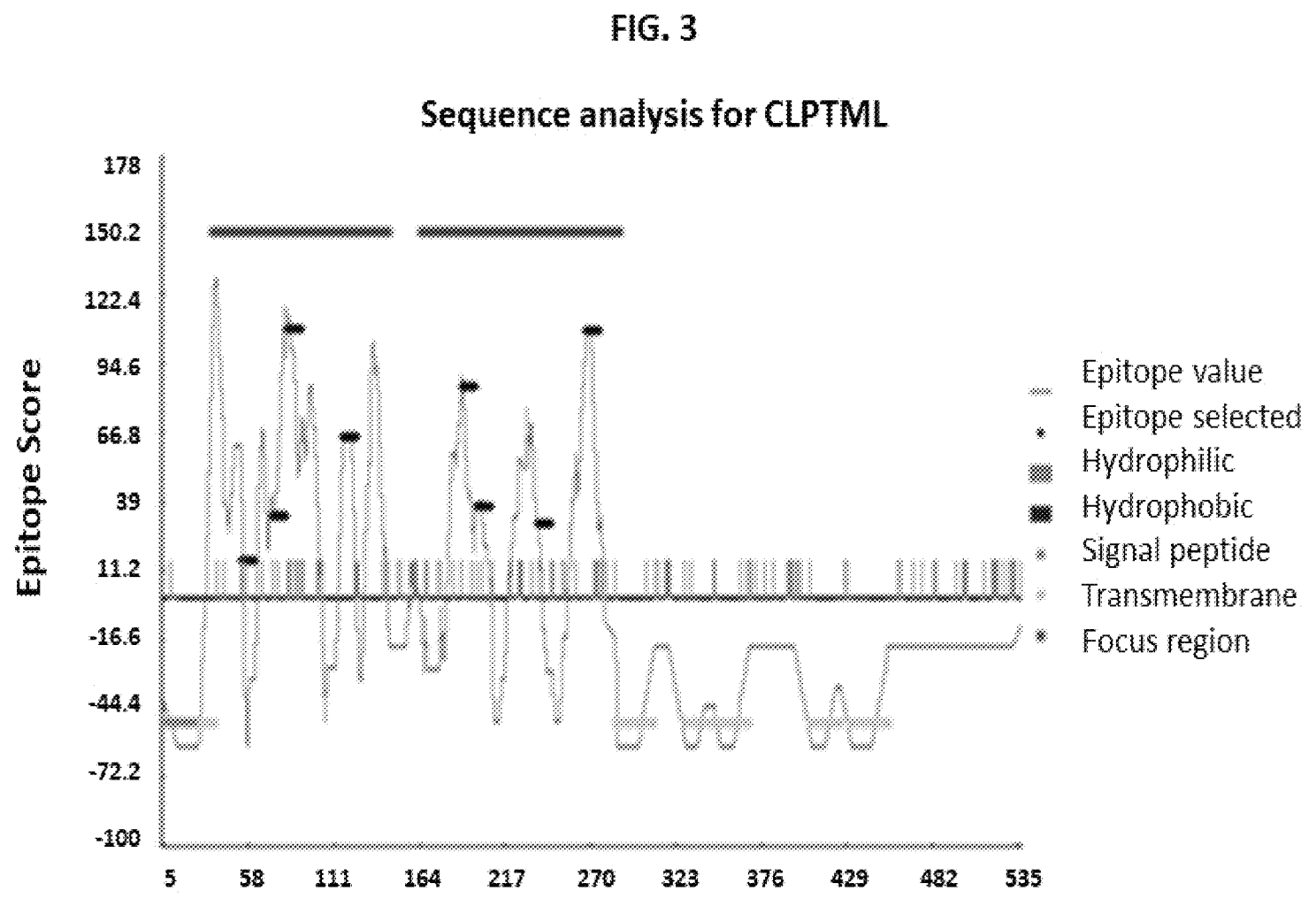

Since monoclonal antibodies are definable, consistent, reproducible, and capable of being manipulated, we contracted the production of a panel of monoclonal antibodies targeting the human CLPTM1L protein. Design of peptide epitopes against which to raise monoclonal antibodies took several factors into consideration. We designed the epitopes to reside within the cell surface exposed globular domains of CLPTM1L (residues 32-284, avoiding glycosylation sites (91, 101, 229), avoiding the disordered region (141-162), and prioritizing amino acid residues scoring highly on the basis of hydrophilicity, folding potential, and antigen presentation. Eight epitopes, each 11 amino acids in length, were selected for monoclonal antibody production (FIG. 3; see also Table 1). While polyclonal antibodies may be generated against peptides of 8-22 amino acids, epitopes of 9-11 amino acids are typically chosen for specific monoclonal antibody production. Other potential epitopes selected bases on similar parameters are presented in the unshaded boxes of Table 1.

Figures 4A, 4B, 4C, 4D:
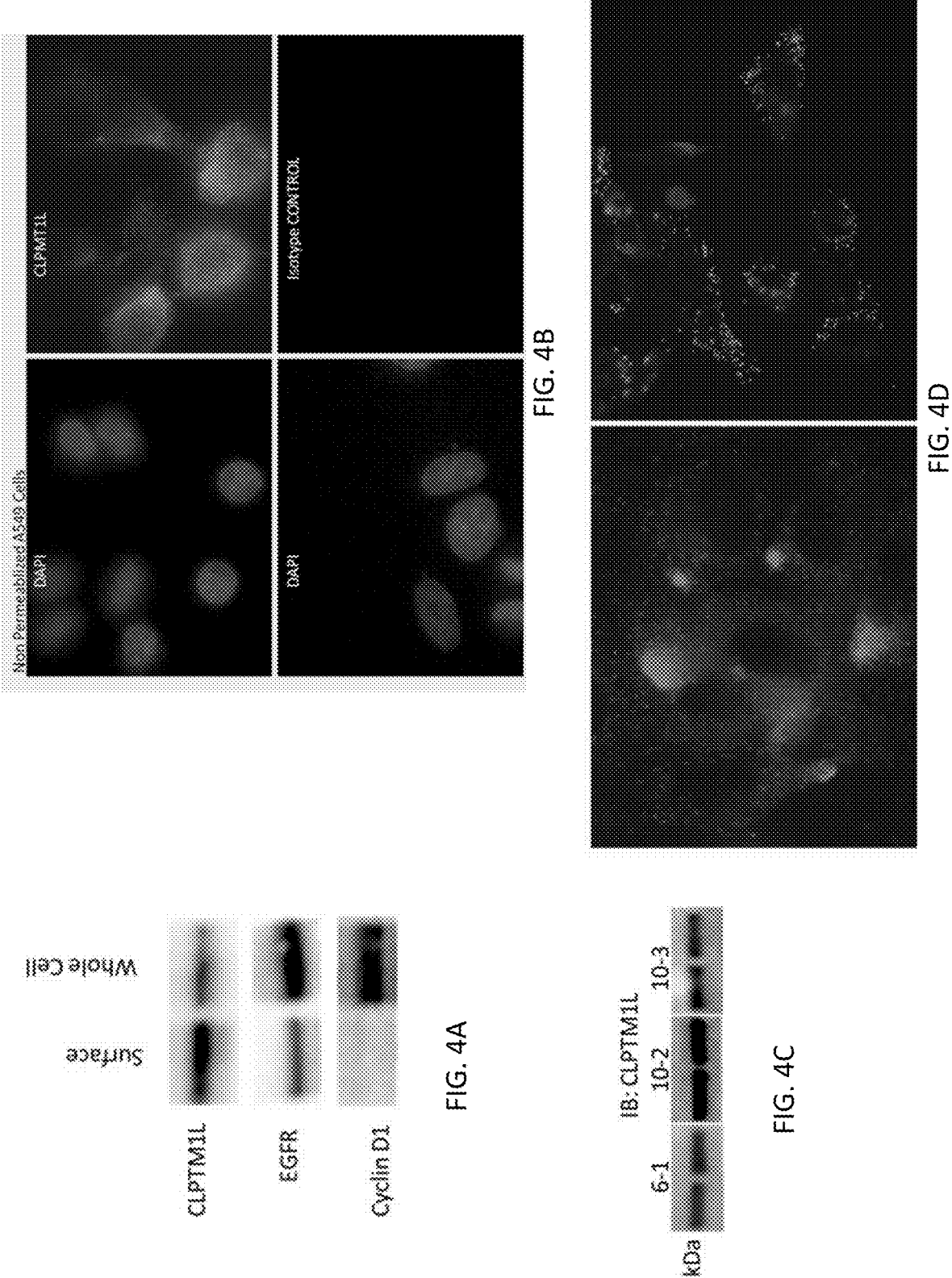
FIGS. 4A-4D demonstrate CLPTM1L localization. (A) Western blotting of cell surface and whole cell protein lysates for CLPTM1L, transmembrane receptor EGFR and nuclear protein Cyclin D1. Monoclonal antibodies 6-1, 10-2, and 10-3 were used for western blotting. (B) Immunofluorescent staining of non-permeabilized A549 lung tumor cells using DAPI dye to stain cell nuclei and polyclonal antibody to the predicted extracellular N-terminus of human CLPTM1L followed by a secondary FITC conjugated antibody to detect CLPTM1L. A non-specific antibody was used as a control. Staining indicates punctuate plasma membrane localization of the protein. (C) Western blotting for CLPTM1L in H838 cells with monoclonal antibodies. (D) Immunofluorescent staining of non-permeabilized A549 cells with monoclonal CLPTM1L antibodies 6-1 (1000×) and 10-2 (400×). Monoclonal antibodies 6-1 and 10-2 were used for immunofluorescence.

To confirm the localization of CLPTM1L at the surface of tumor cells, we isolated cell-surface proteins from A549 human lung tumor cells by biotinylation and extraction with a streptavidin resin. Western analysis of whole cell and cell-surface lysates demonstrated a prevalence of CLPTM1L at the cell-surface (FIG. 4A). EGFR, used as a cell-surface localized control, was detected at the cell-surface at a lesser intensity than CLPTM1L relative to whole cell lysate signal. Cyclin D1, used as a nuclear protein control, was not detected at the cell surface. Immunofluorescence staining of non-permeabilized A549 cells for CLPTM1L revealed a punctate cell-surface staining pattern (FIG. 4B).

The panel of monoclonal antibodies targeting the extracellular globular domains of CLPTM1L was tested for detection of CLPTM1L and immunofluorescent labeling of surface CLPTM1L. All antibodies strongly detected the 62-kilodalton CLPTM1L protein by western blot (FIG. 4C; some data not shown). All antibodies resulted in a cell-surface staining pattern when used for immunofluorescence on non-permeabilized A549 cells, with antibodies targeting ECR2 exhibiting a more distinct punctate staining (FIG. 4D; some data not shown).

Example 2—In Vitro Analysis of CLPTM1L Monoclonal Antibodies

To determine if CLPTM1L expression was associated with K-Ras driven pancreatic cancer treated with adjuvant therapy, we utilized available pancreatic tissue microarrays on 31 patients using matched survival data. Staining intensity of tumors that were subjected CLPTM1L immunohistochemistry (IHC) were scored by three pathologists and the scores averaged. Staining was uniformly negative in normal ductal epithelia, while positive in 94% (29/31) of tumor cells (r=0.78, p<5×10–0) (FIG. 5A). Tumors were scored as negative (0), weak (+1), moderate (+2) or strong (+3). Independent scores were averaged. Tumors had an average score of 1.46 while that of normal ductal epithelial was 0 (p<0.05). Tumors expressing low levels of CLPTM1L as defined by an average score of 1.15 or less were associated with increased survival, while patients with higher expression had shorter survival times. Patients exhibiting low CLPTM1L expression in tumor tissues had a median survival of 24 months, while patients with medium and high CLPTM1L expression in tumor tissues had a median survival of 11 and 14 months respectively (FIG. 5B). Representative tissues stained with CLPTM1L antibody are shown in FIG. 5C.

Figure 6B:
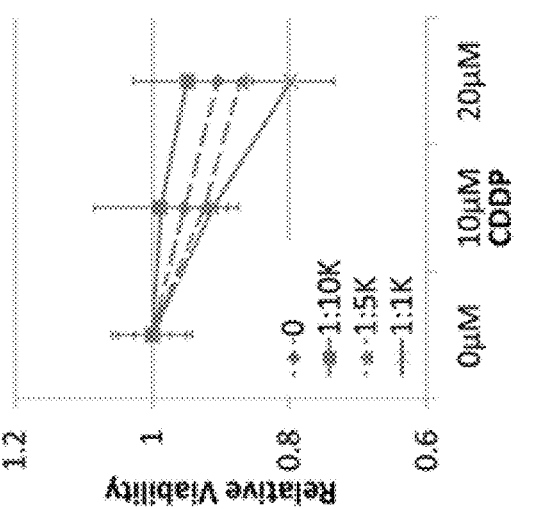
FIGS. 6A-6D demonstrate that targeting CLPTM1L in tumor cells modulates Bcl-xL and Akt survival signaling and sensitizes cells to killing with cisplatin. (A) Treating A549 cells with polyclonal anti-CLP antibody (1:1000=1 μg/mL) reduced accumulation of anti-apoptotic molecules Bcl-xL and total Akt. (B) Anti-CLPTM1L significantly increased sensitivity to killing upon cisplatin treatment for 24 hours (p<0.05). (C) Treatment with monoclonal anti-CLP (10-2) increased sensitivity of pancreatic adenocarcinoma cells to killing by gemcitabine (500 μM for 72 hours). (D) Treatment of pancreatic adenocarcinoma cells with monoclonal anti-CLP (10-2) reduced accumulation of phosphorylated Akt.

We previously demonstrated that targeting CLPTM1L in tumor cells modulates Bcl-xL and Akt survival signaling and sensitizes cells to killing with cisplatin. Polyclonal antibody raised against amino acid residues 18-307 of human CLPTM1L was applied to A549 human lung tumor cells at concentrations of 0, 1, and 5 μg/mL. After culture for 48 hours with polyclonal antibody treatment, Western blotting was conducted for Bcl-xL, total Akt1, and phospho-Akt1. Dose dependent decreases in the accumulation of both Bcl-xL and Akt1 with anti-CLPTM1L treatment were observed (FIG. 6A). To determine the effect of treatment with polyclonal antibody on sensitivity to cisplatin, cells were treated with dilutions of anti-CLPTM1L from 0.01 to 1 μg/mL for 24 hours. Cells were then exposed to cisplatin at 0, 10, and 20 μM concentrations for 48 hours. Treatment with anti-CLPTM1L resulted in a decrease in cell viability following cisplatin treatment that was dependent on the dose of antibody (FIG. 6B). These results demonstrate sensitization to cisplatin killing using the antibody.

Figure 6D:
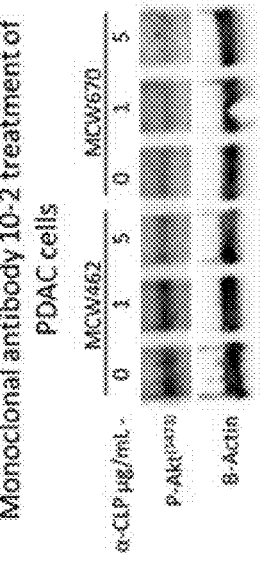
Figure 6A:
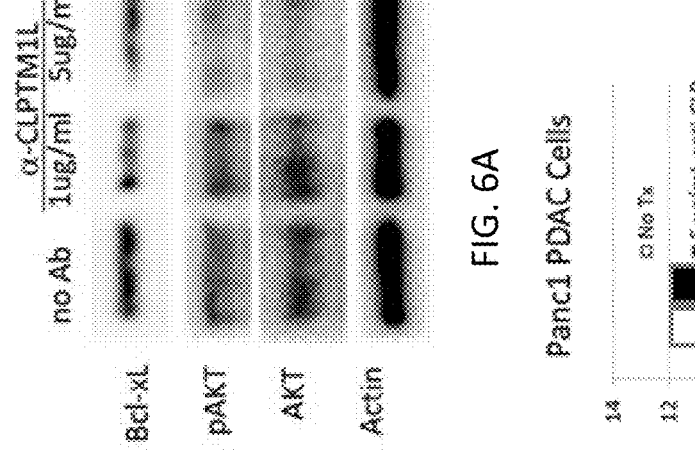
Figure 6C:
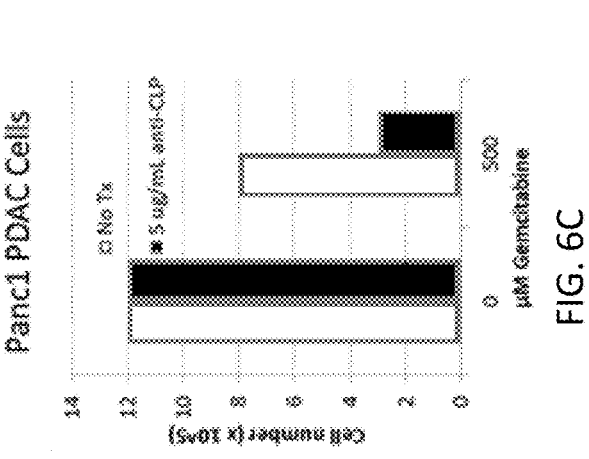
Figure 7:
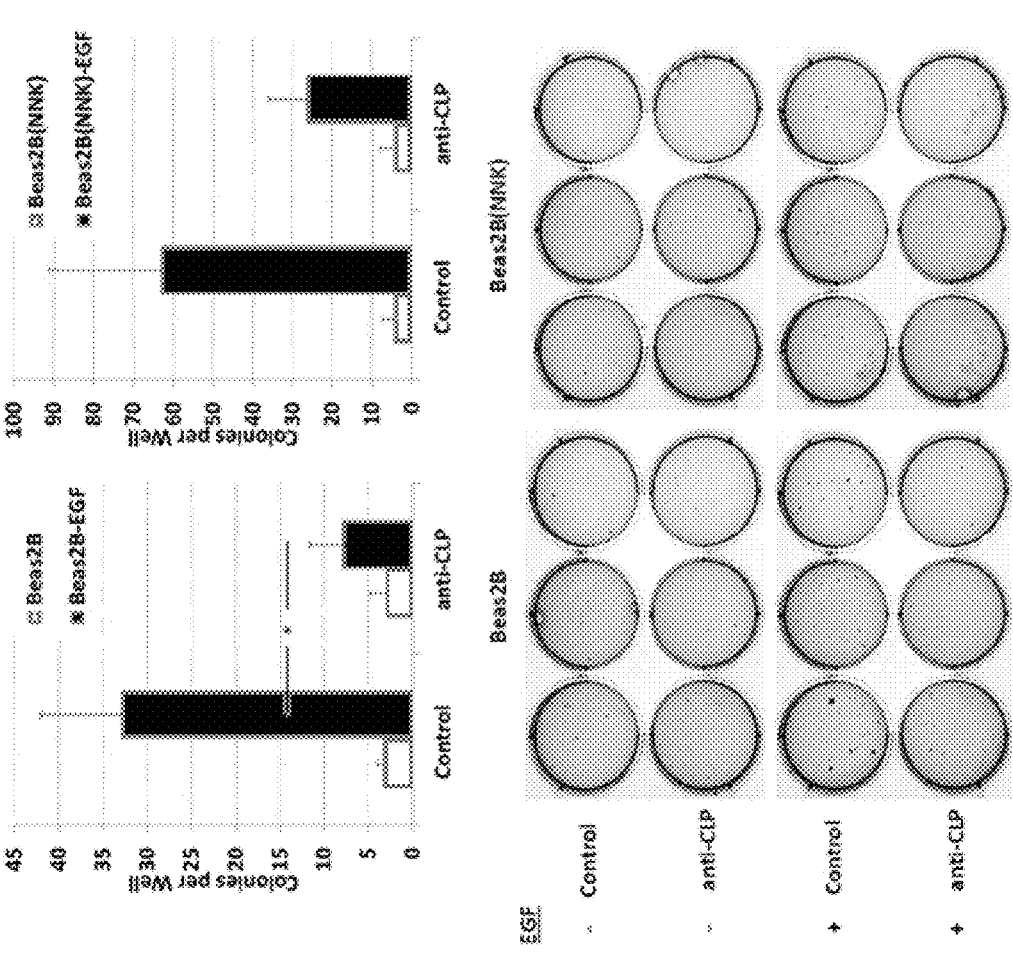
FIG. 7 presents images and graphs demonstrating that treatment with anti-CLP antibody (Ab) inhibits anchorage-independent growth of human lung tumor and bronchial epithelial cells in vitro. Anchorage-independent growth of human lung tumor cells, as measured by colony formation in 0.4% top agar over a 0.8% bottom agar layer, was inhibited by 55%-65% by anti-CLPTM1L treatment compared to solvent control treated cells (p<0.05). Treatments were administered one day after plating and again one week later. EGF treatment induced anchorage independent growth in Beas2B human bronchial epithelial cells, which was inhibited by 76% upon treatment with anti-CLP Ab.

Treatment with monoclonal anti-CLP (10-2) increased sensitivity of pancreatic adenocarcinoma cells to killing by gemcitabine (500 μM for 72 hours) (FIG. 6C) and also reduced accumulation of phosphorylated Akt (FIG. 6D).

In addition, treatment of A549 and H838 human lung tumor cells with our panel of monoclonal antibodies resulted in depletion of Bcl-xL and Akt phosphorylation with a range of efficacies. Western analysis revealed that treatment with antibodies targeting epitopes 6 and 10 resulted in dose dependent decreases in Bcl-xL and phospho-Akt1 accumulation. Likewise, sensitization to cisplatin killing was accomplished by treatment of tumor cells with anti-CLPTM1L monoclonal antibodies. Monoclonal antibody raised against epitope 10 effectively inhibited anchorage independent growth of A549 cells. Among all monoclonal antibodies raised against the extracellular domains of CLPTM1L, only those raised against epitope 10 were effective in inhibiting anchorage independent tumor spheroid growth of H838 cells. A summary of these results for each antibody clone is given in FIG. 10.

Figure 8B:
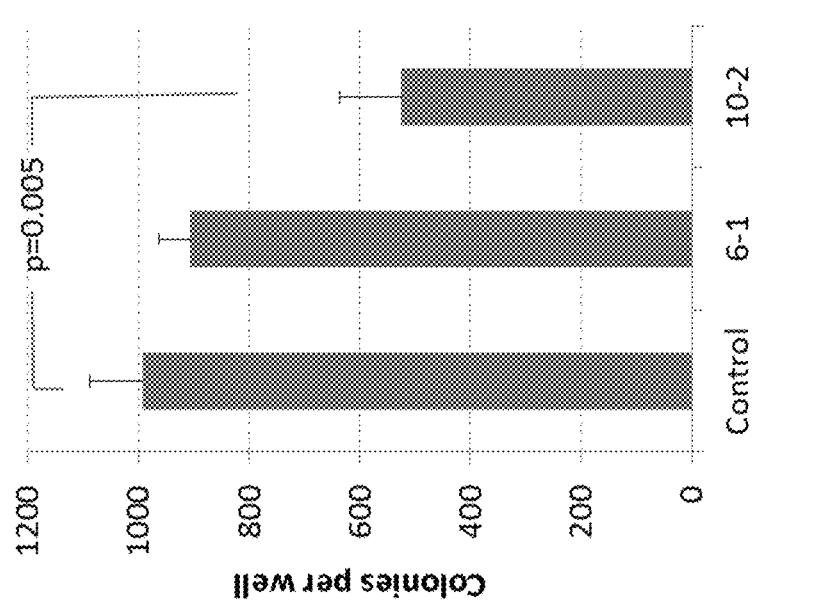
FIGS. 8A-8B demonstrate colony growth inhibition of pancreatic tumor cells by anti-CLPTM1L antibodies. (A) Panc-1 pancreatic tumor cells were plated on 6-well plates in triplicate at 1000 cells per well in DMEM/F12 w/10% FBS. After plating, the indicated antibodies were added to the culture media at 5 μg/mL. (B) Colonies per well were counted after 5 days in culture following fixation in methanol and staining with 0.5% crystal violet. **p=0.005.
Figure 8A:
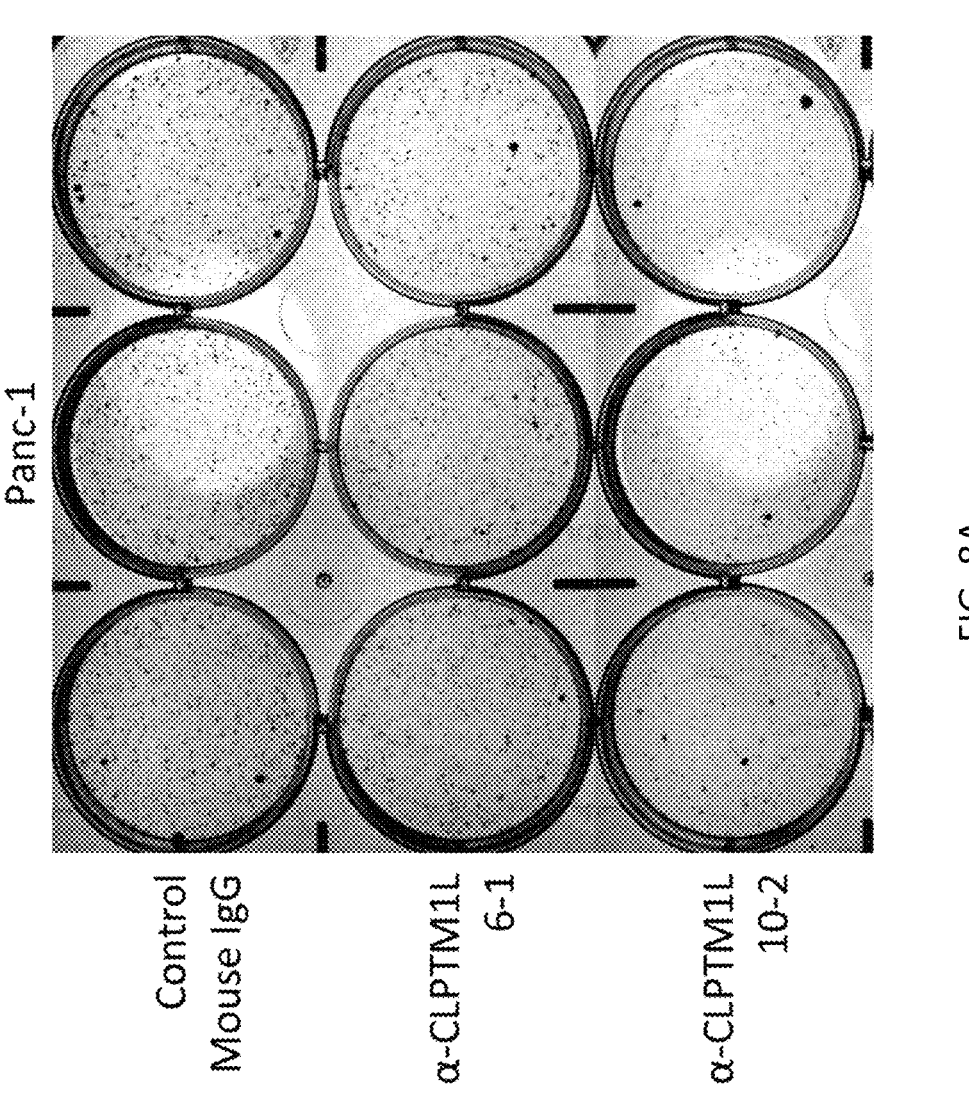

As shown in FIG. 8, we also discovered that treatment with monoclonal anti-CLPTM1L antibodies inhibited colony growth of pancreatic tumor cells. Panc1 pancreatic adenocarcinoma cells were plated at low density and treated with anti-CLPTM1L 6-1, 10-2, or control mouse IgG (FIGS. 8A-B). The number of resulting colonies after 5 days of growth was inhibited by up to 47% by anti-CLPTM1L treatment.

Figure 9B:
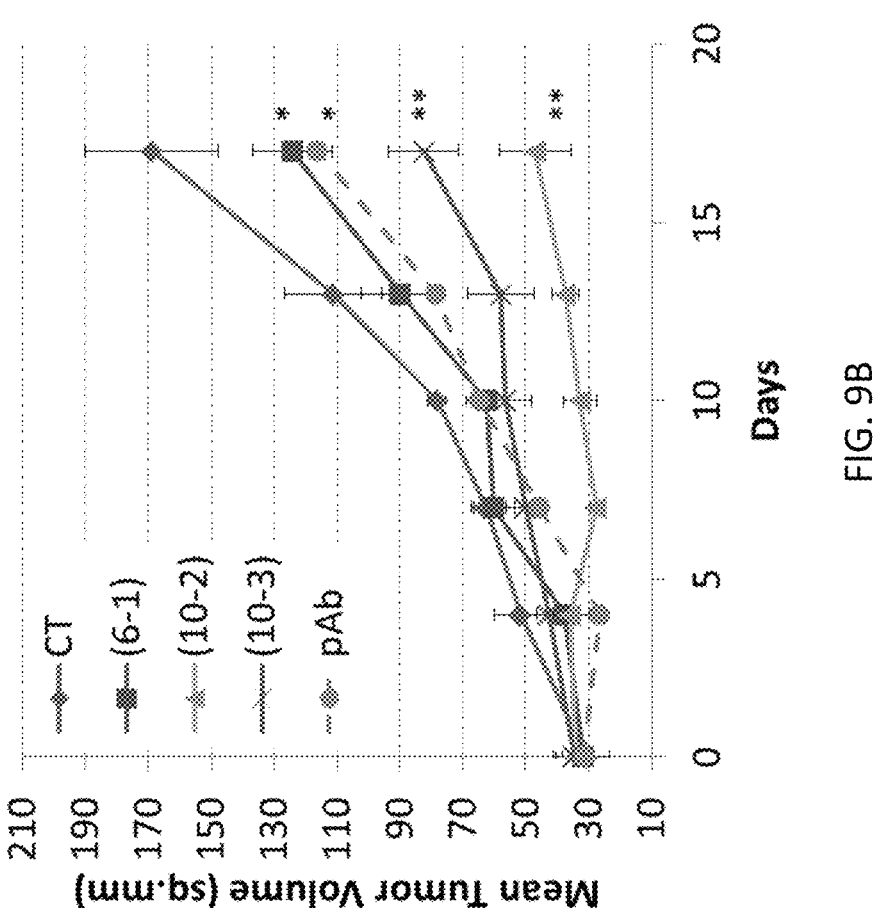
FIGS. 9A-9B present xenograft models for inhibition of the growth of established human lung tumors. (A) Mean tumor volume in athymic nude mice injected subcutaneously with A549 tumor cells and treated with control ascites, polyclonal anti-CLPTM1L, or monoclonal anti-CLPTM1L clones after tumor establishment on days 0, 5, and 12. Error bars represent standard error of the mean. (B) Tumor volumes of individual tumors at day 17. Error bars represent standard deviations. *p<0.05, **p<0.005.
Figure 9A:
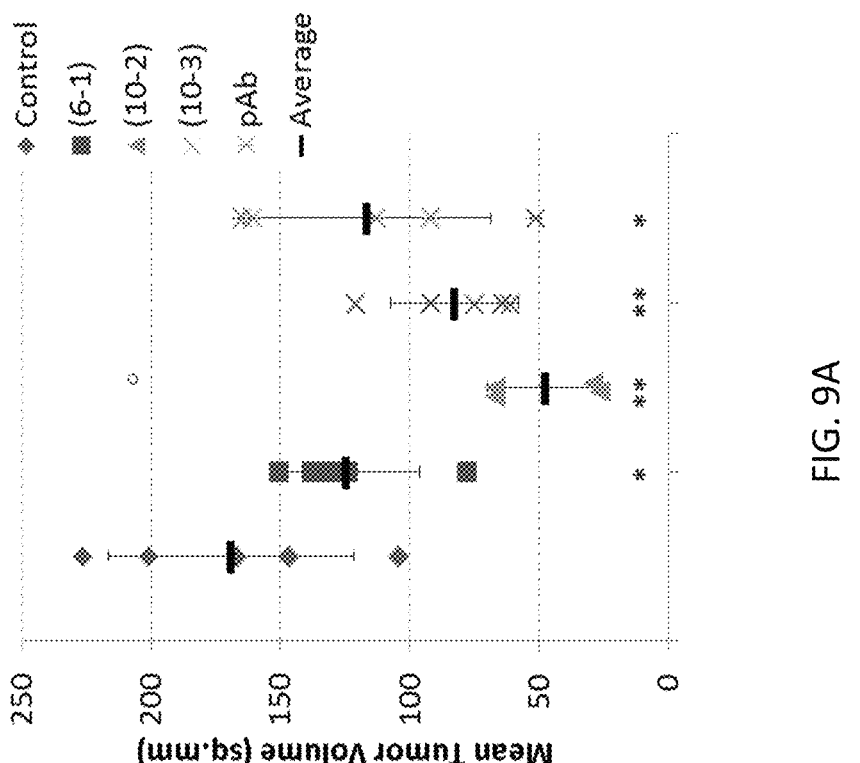

Example 3—Effect of CLPTM1L Monoclonal Antibodies on Human Lung Tumor Xenograft Model Monoclonal antibodies raised against epitope 6 in ECR1 (SEQ ID NO:6) and epitope 10 in ECR2 (SEQ ID NO:10)

were evaluated in xenograft models for inhibition of the growth of established human lung tumor xenografts. A549 cell xenografts were established and mice were separated into groups of equal average tumor size and variance. Mice were treated intraperitoneally with 1 µL/g (estimated to be equivalent to 2-3 mg/kg of antibody) of the indicated monoclonal antibody clone or control ascites on days 0, 5, and 12 post-separation. One group was similarly treated with 1 mg/kg polyclonal antibody. Polyclonal antibody and monoclonal clone 6-1 modestly but significantly inhibited tumor growth over 17 days post-treatment (FIG. 9). Antibodies raised against epitope 10 (10-2 and 10-3) had a more robust and more significant inhibitory effect on tumor growth. Monoclonal clone 10-2 inhibited tumor growth by 88% (p<0.005).

The examples and data set forth above demonstrate that anti-CLPTM1L immunoglobulins are anti-tumor agents in vivo and in vitro. Furthermore, they describe specific epitopes expected to be efficacious in targeting the extracellular domains of CLPTM1L.

Example 4—Characterization of Human Anti-CRR9/CLPTM1L Clones

Human anti-CRR9/CLPTM1L antibodies were obtained that comprise the IgG1 variable region sequences that are set forth in Table 3. Underlined residues indicate CDRs for each chain (set forth individually in Table 4).

TABLE 3

| Human Anti-CRR9/CLPTM1L IgG1 variable region sequences | | |
|---|---|---|
| Anti-CRR9/CLPTM1L clone | IgG1 variable region sequences | SEQ ID NO: |
| 102-1 | Heavy chain V EVQLLESGAEVKKPGSSVKVSCKASGGTFSSYAISWVRQAPGQ GLEWMGIINPSGGSTSYAQKFQGRVTMTRDTSTSTVYMELSSL RSEDTAVYYCARGGLSRLEILLDNWGQGTLVTVSS | 26 |
| | Light chain V VHVILTQPPSLSAAPGQRVTISCSGSDSNIGNNYVSWYRQFPGT APKLLIYDNNKRPSGVPDRFSGSKSGTSAILDITGLQAGDEADY YCGSWDTSLDAWVFGGGTKLTVL | 27 |
| 102-4 | Heavy chain V EVQLLESGGGVVQPGGSLSLSCAASGFTFKNYGMHWVRQAPG KGLEWVSGISWNSGSIGYADSVKGRFTISRDNAKNSLYLQMNS LRAEDTAVYYCARSRYSDYWGQGTLVTVSS | 28 |
| | Light chain V DIQMTQSPSSLSASVGDRVTIACRASQGIRNDLGWYQQKPGKA PKLLIYAASSLQSGVPSRFSGSGSGTDFTLTIIILQPEDYATYYCL QDYNYPWTFGQRTKLDIK | 29 |
| 102-5 | Heavy chain V EVQLLESGGGLVQPGGSLRLSCAASGFSFSSYEMNWVRQAPGK GPEWISYISSGGGTIYYADSVRGRFTISRDNSNNTLYLQMNSLRP DDTAIYYCARDRGRKWLQLLFDSWGQGTLVTVSS | 30 |
| | Light chain V QAVLTQPPSASGTPGQKVTISCSGSSSNIGSNTVNWYQQLPGTA PKLLIYTNNQRPSGVPDRFSGSKSGASASLAISGLQSKDEADYY CAAWDDSLNGWVFGGGTKLTVLG | 31 |
| 102-22 | Heavy Chain V EVQLVESGGGVVRPGGSLRLSCAASGFTFDDYGMSWVRQAPG KGLEWVSGINWNGGSTGYADSVKGRFTISRDNAKNSLYLQMN SLRAEDTAVYYCASLTGGYHGMDVWGQGTL | 32 |
| | Light chain V QSVLTQPPSASGTPGQRVTISCSGSSSNIGSNYVYWYQQLPGTA PKLLIYRNNQRPSGVPDRFSGSKSGTSASLAISGLRSEDEADYYC AAWDDSLSGPWVFGGGTKVTVL | 33 |
| 102-27 | Heavy chain V EVQLVESGAEVKKPGSSVKVSCKASGGTFSIYATNWVRQAPGQ GPEWMGGIIPMIDTTNYAQKFRGRLTVTADKSTRTAYMELINL TSDDTAVYYCAGDPRRYGDYEYFEFWGQGTLVTVSS | 34 |
| | Light chain V QTVVTQEPSLTVSPGGTVTLTCASSTGAVTSGYFPNWFQQKPG QAPRALIYSTSNRHPWTPARFSGSLLGGKAALTLSGVQPEDEAD YYCLIYSGGVYVFGTGTKLTVL | 35 |

TABLE 4

| V_H CDRs and V_L CDRs for Anti-CRR9/CLPTM1L clones | | |
|---|---|---|
| Anti-CRR9/CLPTM1L clone | V_H CDRs | V_L CDRs |
| 102-1 | CDR1: GGTFSSY (SEQ ID NO: 36) CDR2: NPSGGS (SEQ ID NO: 37) CDR3: GGLSRLEILLD (SEQ ID NO: 38) | CDR1: SGSDSNIGNNYVS (SEQ ID NO: 39) CDR2: DNNKRPS (SEQ ID NO: 40) CDR3: GSWDTSLDAWV (SEQ ID NO: 41) |
| 102-4 | CDR1: GFTFKNY (SEQ ID NO: 42) CDR2: SWNSGS (SEQ ID NO: 43) CDR3: SRYSDY (SEQ ID NO: 44) | CDR1: RASQGIRNDLG (SEQ ID NO: 45) CDR2: AASSLQS (SEQ ID NO: 46) CDR3: LQDYNYPWT (SEQ ID NO: 47) |
| 102-5 | CDR1: GFSFSSY (SEQ ID NO: 48) CDR2: SSGGGT (SEQ ID NO: 49) CDR3: DRGRKWLQLLFDS (SEQ ID NO: 50) | CDR1: SGSSSNIGSNTVN (SEQ ID NO: 51) CDR2: TNNQRPS (SEQ ID NO: 52) CDR3: AAWDDSLNGWV (SEQ ID NO: 53) |
| 102-22 | CDR1: GFTFDDY (SEQ ID NO: 54) CDR2: NWNGGS (SEQ ID NO: 55) CDR3: LTGGYHGMDV (SEQ ID NO: 56) | CDR1: SGSSSNIGSNYVY (SEQ ID NO: 57) CDR2: RNNQRPS (SEQ ID NO: 58) CDR3: AAWDDSLSGPWV (SEQ ID NO: 59) |
| 102-27 | CDR1: GGTFSIY (SEQ ID NO: 60) CDR2: IPMIDT (SEQ ID NO: 61) CDR3: DPRRYGDYEYFEF (SEQ ID NO: 62) | CDR1: ASSTGAVTSGYFPN (SEQ ID NO: 63) CDR2: STSNRHP (SEQ ID NO: 64) CDR3: LIYSGGVYV (SEQ ID NO: 65) |

Human anti-CRR9/CLPTM1L antibodies were obtained using the codon-optimized DNA sequences for human anti-CRR9/CLPTM1L expression (variable regions with linker for scFv) that are set forth in Table 5.

TABLE 5

| Codon-Optimized DNA Sequences for Human Anti-CRR9/CLPTM1L Expression | | |
|---|---|---|
| Anti-CRR9 clone | Codon-Optimized DNA Sequences | SEQ ID NO: |
| 102-21 | CACGTGATCCTGACACAGCCTCCTAGCCTGTCTGCTGCCCCT GGACAGAGAGTGACCATCAGCTGTAGCGGCAGCGACAGCAA CATCGGCAACAACTACGTGTCCTGGTACAGACAGTTCCCCGG CACAGCCCCTAAGCTGCTGATCTACGACAACAACAAGCGGC CTAGCGGCGTGCCCGATAGATTTTCTGGCAGCAAGAGCGGC ACCAGCGCCATCCTGGATATTACAGGACTGCAGGCCGGCGA CGAGGCCGATTACTATTGTGGCAGCTGGGACACCAGCCTGG ACGCTTGGGTTTTCGGCGGAGGCACAAAGCTGACAGTGCTTG GAGGCGGAGGATCTGGCGGCGGAGGAAGCGGAGGCGGTTCT GGCGGTGGTGGATCTGAAGTTCAGCTGCTGGAATCTGGCGCC GAAGTGAAGAAACCTGGCAGCAGCGTGAAGGTGTCCTGCAA AGCTTCTGGCGGCACCTTCAGCAGCTACGCCATCTCTTGGGT TCGACAGGCCCCAGGACAAGGCCTGGAATGGATGGGCATCA TCAATCCAAGCGGCGGCAGCACAAGCTACGCCCAGAAATTC CAGGGCAGAGTGACAATGACCAGAGACACCAGCACCTCCAC CGTGTACATGGAACTGAGCAGCCTGAGAAGCGAGGACACCG CCGTGTACTACTGTGCTAGAGGCGGCCTGAGCCGGCTGGAA ATCCTGCTGGATAATTGGGGCCAGGGCACCCTGGTCACAGTG TCATCT | 66 |
| 102-4 | GAAGTGCAGCTGCTGGAATCTGGTGGCGGAGTTGTTCAGCCT GGCGGCTCTCTGTCTCTGTCTTGTGCCGCCAGCGGCTTCACCT TCAAGAACTACGGCATGCACTGGGTCCGACAGGCCCCTGGA AAAGGCCTTGAATGGGTGTCCGGCATCAGCTGGAATAGCGG CTCTATCGGCTACGCCGACAGCGTGAAGGGCAGATTCACCAT CAGCCGGGACAACGCCAAGAACAGCCTGTACCTGCAGATGA ACTCCCTGAGAGCCGAGGACACCGCCGTGTACTACTGTGCCA GAAGCCGGTACAGCGACTATTGGGGCCAGGGCACACTGGTC ACAGTTTCTAGCGGAGGCGGAGGAAGTGGCGGCGGAGGATC TGGCGGTGGTAGTGGCGGTGGCGGTTCTGACATTCAGATGAC ACAGAGCCCCAGCAGCCTGTCTGCCTCTGTGGGAGACAGAG TGACAATCGCCTGCAGAGCCAGCCAGGGCATCAGAAATGAC | 67 |

TABLE 5-continued

Codon-Optimized DNA Sequences for Human Anti-CRR9/
CLPTM1L Expression

| Anti-CRR9 clone | Codon-Optimized DNA Sequences | SEQ ID NO: |
|---|---|---|
| | CTCGGCTGGTATCAGCAGAAGCCCGGCAAAGCCCCTAAGCT GCTGATCTATGCCGCCTCCTCTCTGCAATCTGGCGTGCCCTCT AGATTTTCCGGCTCTGGCAGCGGCACCGACTTCACCCTGACC ATCATCATCCTGCAGCCTGAGGACTACGCCACCTACTACTGC CTGCAAGACTACAACTACCCCTGGACCTTCGGCCAGAGGAC CAAGCTGGATATCAAG | |
| 102-5 | CAGGCTGTGCTGACTCAGCCGCCCTCAGCGTCTGGGACCCCC GGGCAGAAGGTCACCATCTCTTGTTCTGGAAGCAGCTCCAAC ATCGGAAGTAATACTGTAAACTGGTACCAACAGCTCCCAGG AACGGCCCCCAAACTCCTCATCTATACTAATAATCAGCGGCC CTCAGGGGTCCCTGACCGATTCTCTGGCTCCAAGTCTGGCGC CTCAGCCTCCCTGGCCATCAGTGGGCTCCAGTCTAAGGATGA GGCTGATTATTACTGTGCAGCATGGGATGACAGCCTGAATGG TTGGGTGTTCGGCGGAGGGACCAAGCTCACCGTCCTAGGTG AGGGTAAATCTTCCGGATCTGGTTCCGAATCCAAAGCTAGCG AGGTGCAGCTGTTGGAGTCTGGGGGAGGCTTGGTTCAGCCG GGAGGGTCCCTGAGACTCTCCTGTGCAGCCTCTGGATTCAGC TTCAGTAGTTATGAAATGAACTGGGTCCGCCAGGCTCCAGGC AAGGGGCCGGAGTGGATTTCATACATCAGCAGTGGTGGTGG TACCATATACTACGCAGACTCCGTGAGGGGCCGATTCACCAT CTCCAGAGACAACTCCAACAACACTCTGTATCTGCAAATGAA CAGCCTGAGACCTGACGACACGGCTATTTATTACTGTGCGAG AGACCGGGGACGGAAATGGCTACAACTATTGTTTGACTCCTG GGGCCAGGGCACCCTGGTCACCGTCTCCTCA | 68 |
| 102-22 | CAGTCTGTGCTGACACAGCCTCCATCTGCCTCTGGCACACCT GGCCAGAGAGTGACCATCAGCTGTAGCGGCAGCAGCAGCAA CATCGGCAGCAACTACGTGTACTGGTATCAGCAGCTGCCCGG CACAGCCCCTAAACTGCTGATCTACCGGAACAACCAGCGGC CTAGCGGCGTGCCAGATAGATTTTCTGGCAGCAAGAGCGGC ACCTCTGCCAGCCTGGCTATCTCTGGACTGAGAAGCGAGGAC GAGGCCGACTACTATTGTGCCGCCTGGGATGATAGCCTGAGC GGCCCTTGGGTTTTCGGCGGAGGCACAAAAGTGACAGTGCT CGGAGGCGGAGGATCTGGTGGCGGAGGTAGTGGCGGTGGTT CTGGCGGAGGCGGTTCTGAAGTTCAGCTGGTGGAAAGTGGC GGCGGAGTCGTTAGACCTGGCGGATCTCTGAGACTGTCTTGC GCCGCCAGCGGCTTCACCTTCGATGATTACGGCATGAGCTGG GTCCGACAGGCCCCTGGAAAAGGCCTTGAATGGGTGTCCGG CATCAACTGGAATGGCGGCTCTACAGGCTACGCCGACTCTGT GAAGGGCAGATTCACCATCAGCCGGGACAACGCCAAGAACA GCCTGTACCTGCAGATGAACTCCCTGAGAGCCGAGGACACC GCCGTGTACTACTGTGCATCTCTGACAGGCGGCTACCACGGC ATGGATGTTTGGGGACAGGGCACCCTGGTCACCGTTTCTTCT | 69 |
| 102-27 | CAGACCGTGGTCACACAAGAGCCTAGCCTGACAGTGTCTCCT GGCGGCACAGTGACACTGACATGTGCCTCTTCTACTGGCGCC GTGACCAGCGGCTACTTCCCCAATTGGTTCCAGCAGAAGCCT GGACAGGCCCCTAGGGCTCTGATCTACAGCACCAGCAACAG ACACCCCTGGACACCCGCCAGATTTTCTGGCTCTCTGCTCGG AGGAAAGGCCGCTCTGACACTGTCTGGTGTCCAGCCTGAGG ACGAGGCCGATTACTACTGCCTGATCTACTCTGGCGGCGTGT ACGTGTTCGGCACCGGCACAAAACTGACAGTGCTTGGCGGC GGAGGATCTGGCGGAGGTGGAAGCGGAGGCGGTAGTGGTGG TGGCGGATCTGAAGTGCAGCTGGTGGAATCTGGCGCCGAAG TGAAGAAACCTGGCAGCAGCGTGAAGGTGTCCTGCAAAGCT AGCGGCGGCACCTTCAGCATCTACGCCACAAACTGGGTCCG ACAGGCTCCAGGACAAGGCCCTGAATGGATGGGCGGCATCA TCCCCATGATCGACACCACCAACTACGCCCAGAAGTTCCGG GGCAGACTGACCGTGACAGCCGACAAGTCTACCCGGACCGC CTACATGGAACTGATCAACCTGACCAGCGACGACACCGCCG TGTACTATTGTGCTGGCGACCCCAGAAGATACGGCGACTACG AGTACTTCGAGTTCTGGGGCCAGGGCACCCTGGTCACAGTTT CTTCT | 70 |

Example 5—Targeted Biologic Inhibition of Both
Tumor Cell-Intrinsic and Intercellular
CLPTM1L/CRR9-Mediated Multi-Drug Resistance
in Ovarian Cancer This example demonstrates re-sensitization of chemo-therapy resistant human ovarian tumor cells to carboplatin and pancreatic tumor cells to gemcitabine by human anti-CLPTM1L mAbs as first-in-class biologic drug candidates. It was previously shown by the inventor and others that inhibition of CLPTM1L can chemosensitize pancreatic ductal adenocarcinoma to gemcitabine treatment (refs. 10-12). As demonstrated herein, CLPTM1L protein was found to be more abundant in platinum pre-treated ovarian tumor cells, and anti-CLPTM1L treatment was synergistic with carbo-platin killing. Treatment of C57bl/6 mice in a syngeneic model of disseminated peritoneal ovarian cancer with human anti-CLPTM1L inhibited progression of the disease and potentiated the therapeutic activity of carboplatin. Like-wise, anti-CLPTM1L restored platinum sensitivity to novel patient-derived parental and cisplatin-conditioned ovarian tumor cell and spheroid lines, and in xenografts made from these lines. Presented herein is the new finding that, in addition to cell-autonomous effects of CLPTM1L on chemoresistance, CLPTM1L in cell culture supernatants and extracellular vesicle fractions can confer intercellular chemoresistance to bystander ovarian and pancreatic tumor cells. Extracellular vesicle CLPTM1L abundance was increased upon pre-treatment with chemotherapy.

With relatively long remissions and favorable co-morbid-ity profiles after first line therapy, ovarian carcinoma is particularly amenable to early clinical trials and mainte-nance therapy with targeted biologics. Tumoricidal activity and improvement of therapeutic index by inhibition of a novel mechanism of both cell-autonomous and nonautono-mous (extracellular vesicle) cytoprotection encourages fur-ther investigation of anti-CLPTM1L mAbs as oncology drug candidates.

Materials and Methods

Cell Culture and Reagents
ID8 mouse epithelial ovarian cancer cells, A2780, Ovcar4, Panc1, and A549 human tumor cells were obtained from ATCC and authenticated within 6 months of experi-ments (RRIDs: CVCL_UI14, CVCL_0134, CVCL_0480, CVCL_1627, and CVCL_0023, respectively). Panc1, A2780, Ovcar4 and A549 were cultured in RPMI1640 plus 10% fetal bovine serum (FBS) (ThermoFisher, Waltham, MA). ID8 cells expressing luciferase were obtained from the Katherine Roby Laboratory at the University of Kansas and were authenticated within 6 months of experiments (RRID: CVCL_IU15). ID8 were cultured in DMEM with 4% FBS and 5 mg/ml Insulin transferrin selenium. Gemcitabine and carboplatin were purchased from Sigma-Aldrich (St. Louis, MO) and prepared immediately before use in a 100 mM aqueous stock solution. Polyclonal anti-CLPTM1L (HPA014791, Sigma Aldrich, St. Louis, MO) or monoclonal anti-CLPTM1L antagonist (12) was used in anti-CLPTM1L inhibition studies. Human ovarian epithelial carcinoma tis-sue obtained as per MCW-IRB-Human Research guidelines and verified as endometrioid subtype of ovarian cancer was used to develop MCW-OV-SL-3 cell line, which cultured in DMEM 10% fetal bovine serum, 50 U/mL of penicillin/ streptomycin, 2 mmol/L of L-glutamine, 1 mmol/L of sodium pyruvate and were grown at 37° C. in an atmosphere of 5% carbon dioxide. These cells were validated by STR sequencing (IDEXX BioAnalytics, using CellCheck 16 Plus profile) and found to be unique and distinct from any known cell line. Cisplatin resistant line was established by exposure to increasing concentration of cisplatin over a period of 12 months to develop cisplatin resistant cell line (MCW-OV-SL3-CP).

Antibody diluent as described by Abcam was used as a vehicle control for polyclonal antibody treatment where indicated to account for any effect of diluent constituents. Normal mouse IgG (Thermo Fisher, 02-7102) was used as a non-specific antibody control for monoclonal antibody treat-ment where indicated. Rabbit α-HA (Santa Cruz Biotech-nology, Santa Cruz, CA. Y-11) was used as a non-specific antibody control for polyclonal antibody treatment where indicated. Mouse α-HA (Cell Signaling, Boston, MA, 6E2) was used as a non-specific antibody control for experiments with purified monoclonal antibodies, and mouse α-human Von Willebrand Factor (hVWF) ascites was used for experi-ments with monoclonal ascites. Monoclonal antibody design, production, and evaluation was done in collaboration with Essential Biotechnology, LLC. (Big Bend, WI). Mouse hybridoma work was contracted to Biomatik Corporation, Cambridge, Ontario, Canada. Expression constructs for FLAG-tagged wild-type and ALoop CLPTM1L were gen-erated and transfected as described in (15). Human mono-clonal antibody inhibitors of CLPTM1L were derived from panning results of a naïve human phage display library (Neoclone, Madison WI) against CLPTM1L peptide antigen representing an ectodomain epitope as defined in (12). Resulting flag tagged scFv clones used in this study are 102-1b, 102-4a, and 102-5a. Heavy and light chain variable regions from clones 1b and 5a were cloned into expression vectors in a full-length human IgG1 framework and expressed transiently in Chinese hamster ovary cells 102-1 and 102-5 (Catalent, Madison WI).
Immunohistochemistry
A full FDA panel of normal human tissues on tissue microarray (TMA) (H1.0x144) was obtained from Proteo-genex (Inglewood, CA). Human patient-derived xenograft tissue slides (FFPE) were obtained from Jackson Labs. IHC staining for CLPTM1L (Human: Polyclonal anti-CLPTM1L (HPA014791, Sigma Aldrich, St. Louis, MO, Mouse: Novus anti-CLPTM1L, NBP1-62477) was performed on the Dako Autostainer Plus using the Dako EnVision™ FLEX High pH Detection Kit (K8010) (Dako, Carpinteria, CA). Slides were deparaffinized to DI water. Antigen Retrieval was performed on Dako PT Link water bath. The antigen retrieval was done at 97° C. for 20 minutes. The slides were cooled until they reached 65° C. All slides for all antibodies were placed in Tris/EDTA pH 9 (Dako TRS High pH). Slides were washed in Dako wash buffer for 5 minutes. Slides were subjected to a peroxidase Block for 5 minutes. Slides were rinsed twice with wash buffer. Slides were incubated with primary anti-body CLPTM1L (rabbit polyclonal, Sigma Aldrich cat #HPA014791, lot A57952) diluted to 1:400 for 30 minutes. Slides were rinsed with wash buffer. Slides were incubated with secondary antibody for 20 minutes and rinsed twice with wash buffer. Slides were incubated with DAB substrate for 10 minutes and rinsed with wash buffer. Slides were stained with hematoxylin for 7 minutes and rinsed with DI water. Slides were dehydrated and cover-slipped for view-ing. Omission of the primary antibody served as negative control. Upon pathologic review, staining intensity in each tumor tissue was scored in triplicate and averaged. Tumors were scored as negative–0, weak–1, intermediate–2, or strong–3. Independent scores were averaged. A staining index was calculated by multiplication of staining score and percentage of tumor cells with that score.

Western Blotting

Cells were lysed with 100 μL of 1× X NP40 lysis buffer containing proteinase inhibitors, sheared 10 times with a 28-gauge needle, spun at 16,000×g for 30 minutes, normalized by protein concentration as determined by the Bradford method, and the supernatant boiled for 5 minutes. Twenty microliters of normalized lysate were resolved by SDS-PAGE on 10% acrylamide gels at 150 volts for 1 hour, transferred by iBlot dry transfer (Life Technologies), blocked for 2 hours with TBST 10% milk, incubated with primary antibodies at 1:1000 in TBST 5% milk at 4° C. overnight with rocking, washed 3×5 minutes with TBST, incubated with secondary anti-rabbit-HRP (Santa Cruz Biotechnology) or goat anti-human-HRP (Invitrogen MH1715) at 1:10,000 in TBST 5% milk for 2 hours with rocking, washed 5×10 minutes with TBST, and signal analyzed using a Biorad Chemidoc XRS. The following antibodies were used: rabbit anti-CLPTM1L (HPA014791, Sigma-Aldrich, St. Louis, MO) (human) or (NBP1-62477, Novus Biologicals, Littleton, CO) (Mouse), anti-Actin (Santa Cruz Biotechnology, 58673), anti-AKT (9272), anti-pAKT (Thr308) (9275). Quantitation of Western analyses of three independent cultures was done using Image J software (24).

Live Cell Imaging

Cells were plated on 24-well tissue culture plates at equal density (~80) confluence and allowed to attach overnight before treatment as indicated in at least triplicate. Culture media contained yoyo-1 fluorescent DNA intercalating dye (ThermoFisher) at a 1:10,000 dilution. Confluence and fluorescent dead cell counts per well were monitored at 3 hour intervals using an Incucyte FLR live cell imager and software (Essen Biosciences, Ann Arbor, MI). Student's T-test determined significance of differences between groups, and ANOVA determined significance of interaction between treatments.

Cytotoxicity Assays

Cells were plate at equal density on 24 well tissue culture plates and treated as indicated. Cells were treated with monoclonal anti-CLPTM1L for 24 hours followed by 72 hours of treatment with gemcitabine at the indicated concentrations. Dead cells were fluorescently stained with Yoyo-1 (Life Technologies) and enumerated on an Incucyte FLR live cell imager (Essen Bioscience). Total cell numbers were then enumerated on the imager by staining with Vybrant Dye Cycle Green (Life Technologies) or by permeabilization to Yoyo-1 with 0.01% Triton X-100. A killing index was calculated for each well by dividing the number of dead cells by the number of total cells. The killing indices of triplicate groups were averaged.

Treatment of Cells with Conditioned Media

Fresh media was placed on 10 cm tissue culture dishes of sub-confluent tumor cells (donor cells), which were then treated as described, carboplatin pre-treatment supernatants after 48 hours of treatment and gemcitabine pre-treatment supernatants after 72 hours of treatment. After 48 hours supernatants were collected, spun at 400×g for 5 minutes to pellet cells, and the supernatant mixed with fresh media at a 1:1 ratio. Anti-CLPTM1L pre-treatment of conditioned supernatants was performed at 4° C. overnight. The supernatant media mixture was pretreated with antibody as indicated and/or added to cells in multi-well plates. Cells were treated with chemotherapeutic agents (Gemcitabine or Carboplatin, Sigma Aldrich) as indicated, 2.5 to 4 hours after treatment with supernatants. Live cell imaging as described above was used to longitudinally monitor cytotoxicity after treatment. Endpoint data was taken from 12-60 hours post treatment as indicated.

Isolation of Extracellular Vesicles, Microvesicles, and Apoptotic Bodies From Culture Media Ultracentrifugation Protocol: One milliliter of serum was centrifuged at 2000×g, 4° C., 15 minutes on a table top centrifuge to remove debris. Supernatant was centrifuged at 10,000×g, 4° C., 30 minutes on a table top centrifuge to remove microvesicles. Supernatant was ultracentrifuged with a SW-55Ti rotor; 140,000×g (34000 rpm); 4° C.; overnight (18 hours) with a 25% sucrose cushion. The pellet was washed 3 times with PBS and ultracentrifuged at 140,000×g, 4° C., 30 minutes and resuspended in 100 μL PBS, stored at −20° C. Vesicle size was measured using AMT Image Capture Engine Software Version 602.571. Protein concentration of samples was measured on a Qubit (Life Technologies). Twenty microliters were added to 10 mL of culture media for treatment of cells.

ExoQuick Protocol: Cell culture supernatants (~10 mL) were collected from donor cells, centrifuged at 300×g for 10 minutes at 4° C. to eliminate cells and cellular debris. Supernatants were then centrifuged at 2000×g for 20 minutes at 4° C. Pellets containing apoptotic bodies were suspended in 30 μL of RIPA buffer with Halt protease inhibitor cocktail and stored at −20° C. Supernatants were then centrifuged at 16500×g for 20 minutes at 4° C. Pellets containing extracellular vesicles (exosomal fraction) were suspended in 30 μL RIPA with Halt protease cocktail and stored at −20° C. One mL of Exoquick TC (System Bioscience, Palo Alto, CA) was added to the remaining supernatant and incubated overnight at 4° C. The mixture was centrifuged at 1500×g for 30 minutes at 4° C. The pellet containing extracellular vesicles was suspended in 50 to 500 μL of RIPA with Halt protease cocktail and stored at −20° C.

Flow Cytometry

Flow cytometry was conducted per AbCam protocol for indirect flow cytometry. Tumor cells were harvested by trypsinization and suspended in cold PBS, 10% FBS, 0.05% $NaN_3$. 100 μL of cell suspension was added to 12×75 mm polystyrene tubes. 10 μg/mL of primary antibody diluted in PBS 3% BSA was added and tubes were incubated at 4° C. in the dark for 45 minutes. After washing 3 times in cold PBS, cells were resuspended in rabbit anti-Human Fc (H&L)-Alexafluor 488 (Abcam) in PBS 3% BSA and incubated at 4° C. in the dark for 30 minutes. After washing 3 times in cold PBS, cells were suspended in 500 μL cold PBS, 3% BSA, 0.05% $NaN_3$ and analyzed on an Accuri C6 flow cytometer. Cells were gated for live cells based on scatter and fluorescence was plotted on a histogram using Flowing Software 2 (Turku Bioimaging).

Phage Display Screening, Codon Optimization and Expression of scFv, scFv-Fc, and Fully Human Anti-CLPTM1L Phage display library screening against CLPTM1L peptide antigen was conducted by Neoclone, LLC, Madison WI. All positive binders in selection and enrichment that were also negative to appropriate counter-screens were analyzed by sequence analysis for identification of unique clones. Individual unique clones were tested for specificity by phage ELISA against the target antigen and carried forward if confirmed. Codon optimization and expression as scFv-Fc fusions by transient transfection of cloned vectors into 293T cells was conducted by Lytic Solutions, LLC in Madison WI. Cloning and expression of full-length human IgG1 in Chinese hamster ovary cells was conducted by Catalent Pharma Solutions in Madison WI.

Ovarian Tumor Models

ID8-luc model: Five-week-old C57bl/6 mice (Jackson labs strain 664) were acclimated for one week and injected intraperitoneally with $5 \times 10^5$ luciferase expressing ID8syngeneic ovarian tumor cells suspended in 200 μL of PBS under Medical College of Wisconsin animal protocol AUA6339. One week after injection, antibodies and/or chemotherapeutic agents were administered intraperitoneally at the indicated doses. Chemotherapeutic doses or vehicle were administered one day before control or therapeutic antibody doses. Imaging and analysis of luciferin radiance was done up to twice weekly on an IVIS Spectrum-CT Imaging System equipped with thermoelectrically-cooled CCD camera. Mice were monitored twice weekly for weight and signs of morbidity. Mice were euthanized after 45 days or upon signs of morbidity. Animal studies were conducted using the standards for humane treatment of animals as described in the U.S. Public Health Service Policy on Humane Care and Use of Laboratory Animals.

SL3 Xenograft Model

Four-week old female NU/J mice (2019, Jackson Laboratories) were acclimated for 1 week before injection of $0.5 \times 10^6$ parental SL3 or $1 \times 10^6$ cisplatin-resistant SL3-cis cells subcutaneously into the flank in 200 μL PBS. Tumors were measured with calipers and volumes were calculated by $\frac{1}{2}(W \times W \times L)$. After tumors had grown to an average of 100 mm$^3$, mice were separated into groups of 5 mice, each group with 100 mm$^3$ average tumor sizes. Mice were treated weekly with intraperitoneal doses of PBS control, cisplatin 2.5 mg/kg, and/or 102-5 5 mg/kg in 200 μL of PBS at room temperature beginning on day 6 post-inoculation. Cisplatin treatments were administered 24 hours following antibody treatment. Tumor volume was measured at least weekly. Animal health was monitored daily and animal weights measured at least weekly. All procedures were reviewed and approved by MCW IACUC committee #2 under AUA6339.

Spheroid Growth and Viability Assays

Combination indices were calculated by:

$$CI = \frac{(C)1}{(C_X)1} + \frac{(C)2}{(C_X)2}$$

where (C)1 and (C)2 are the doses of drugs 1 and 2 with effect x when used together and (CX)1 and (CX)2 are the doses of drugs 1 and 2 that accomplish effect x when used alone.

Results

Figures 11A, 11B, 11C, 11D:
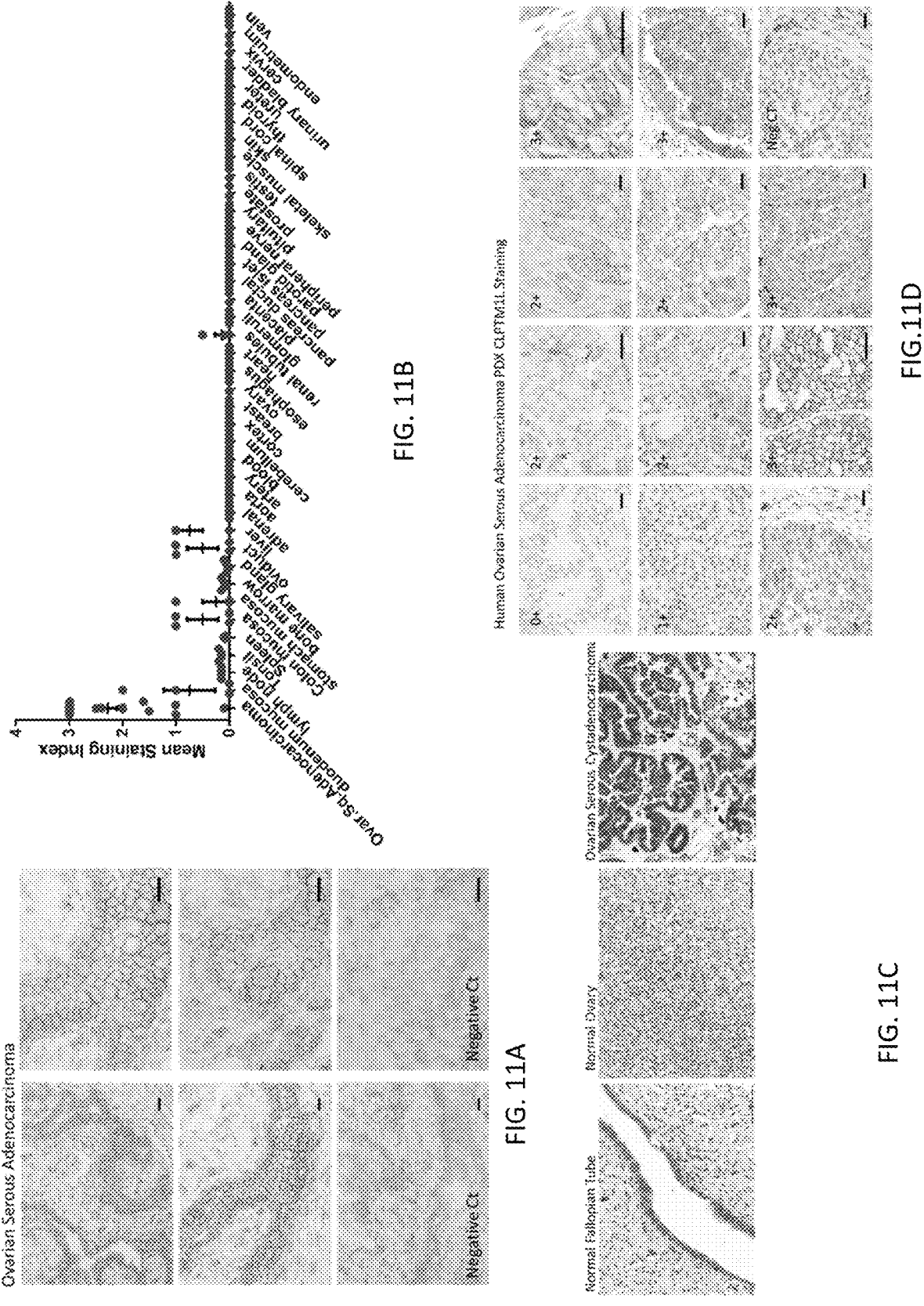
FIGS. 11A-11G demonstrate CLPTM1L expression in tumor and normal tissue and the association of that effect with clinical outcome. (A) CLPTM1L IHC on human ovarian serous adenocarcinomas. Bars=50 μM. (B) IHC staining indices for ovarian serous adenocarcinoma (n=24) and FNA normal human tissues n=144 (n=4 per tissue). (C) Human Protein Atlas staining for CLPTM1L in normal ovarian and fallopian, and ovarian serous adenocarcinoma. (D) CLPTM1L staining on patient-derived xenograft tissues. (E) Progression free survival. (F) Overall survival. (G) Overall survival in patients with CA125<lower quartile as analyzed using KMPlot.
Figures 11E, 11F, 11G:
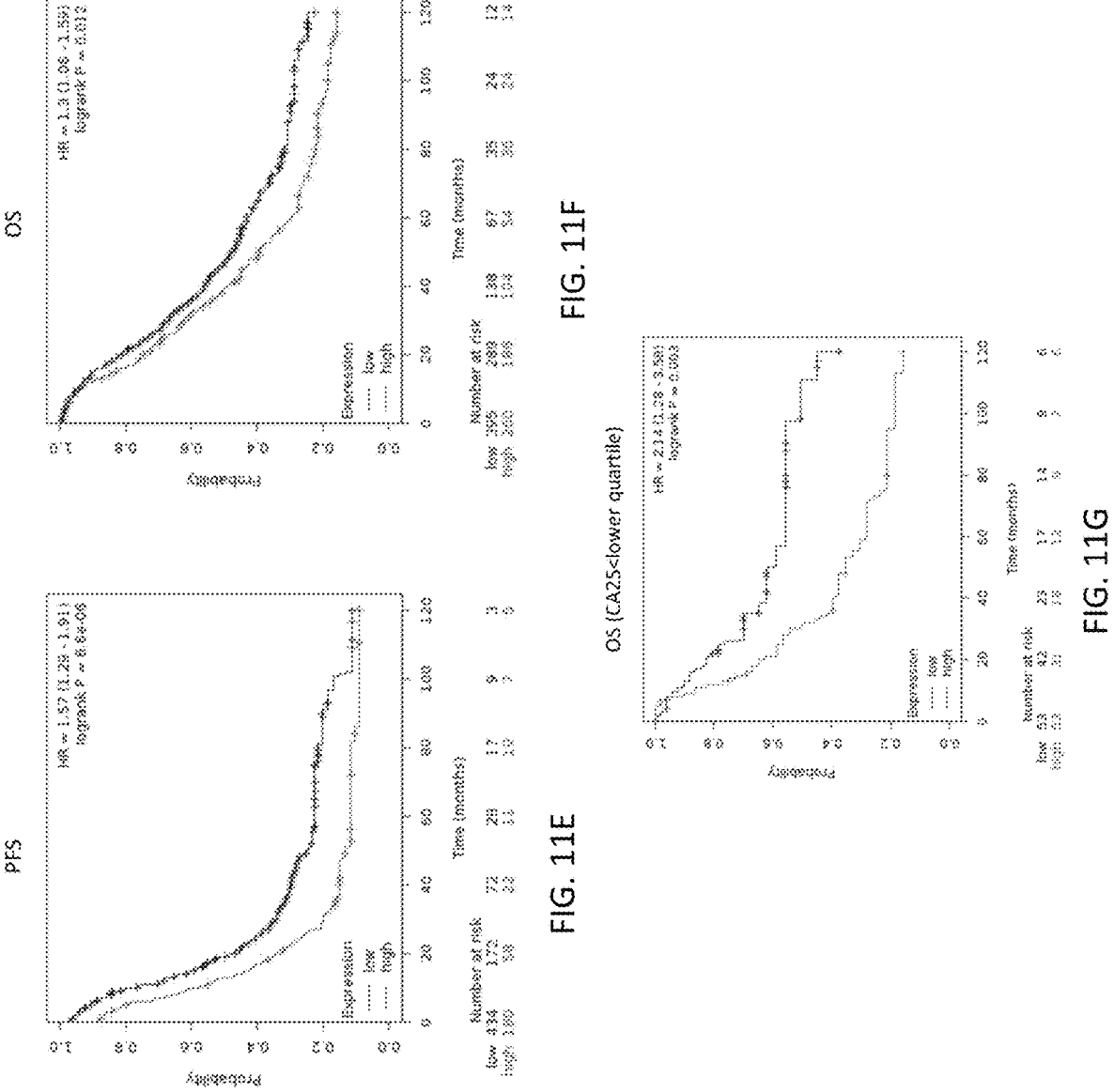

Over-Expression of CLPTM1L in Ovarian Serous Adenocarcinoma and Association With Poor Outcome To determine the level of CLPTM1L protein expression in ovarian serous adenocarcinoma, we conduced immunohistochemistry on frozen histology sections of treatment-naïve tumors from 24 patients. The majority (87.5% of tumors exhibited a moderate to strong staining intensity index (1.5-3 on a 0-3 scale) with an apparent staining of the plasma membrane of tumor cells (FIG. 11A). The overall average staining index was 2.28. In contrast, 144 normal tissues on an FDA tissue microarray (n=4 per tissue) demonstrated weak to no staining, with an average index of 0.089 (T-test p<2×10$^{-5}$) (FIG. 11B). Data collected and annotated by the Human Protein Atlas also demonstrates high CLPTM1L expression in ovarian serous adenocarcinoma with no expression in normal ovary tissue or normal fallopian epithelium (FIG. 11C). Ten of eleven (91%) naïve and platinum-treated human ovarian serous adenocarcinoma patient-derived xenograft tissues stained positively for CLPTM1L with an average staining index of 1.82 (FIG. 11D). There was no statistical difference in expression between naïve and treated tumors, with resolution of differences requiring larger samples sizes. Kaplan-Meier analysis of the CLPTM1L expression on progression free survival in ovarian cancer patients with data on EGA and TCGA as described in (18) showed an association of high CLPTM1L expression with poor outcome with a hazard ratio of 1.57 (log rank p=6.6×10$^{-6}$) (FIG. 11E). High CLPTM1L expression was also associated with poor overall survival with a hazard ratio of 1.3 (p=0.012) (FIG. 11F), particularly for those patients with a CA125 tumor marker level below the lowest quartile (HR=2.14, p=0.003) (FIG. 11G).

Development of Human IgG1 Anti-CLPTM1L for Re-Sensitization of Ovarian Tumor Cells to Carboplatin and Anti-Tumorigenesis Given our previous demonstration of chemosensitization of pancreatic tumor cells to chemotherapeutic killing and inhibition of anchorage independent growth and tumorigenesis using murine monoclonal antibodies (mAbs) targeting CLPTM1L (12), we developed fully human antibodies with antagonism for CLPTM1L.

Given superior chemosensitization and cytotoxic efficacy of mAbs raised against the "lead" epitope, we used peptide antigen representing this epitope to screen a naïve human scFv (single chain variable fragment) phage library for human CLPTM1L-inhibitory antibodies. Five scFv clones specifically binding our epitope resulted from the screen, designated as 102-1b, 102-4a, 102-5a, 102-22, and 102-27. These antibodies were expressed transiently in 293T cells as both scFv fragments and as codon-optimized scFv-Fc (IgG1) fusions and purified. Codon optimized variable sequences of clones 102-1 and 102-5 were expressed transiently in Chinese hamster ovary cells as full-length human IgG1.

Figures 12A, 12B, 12C:
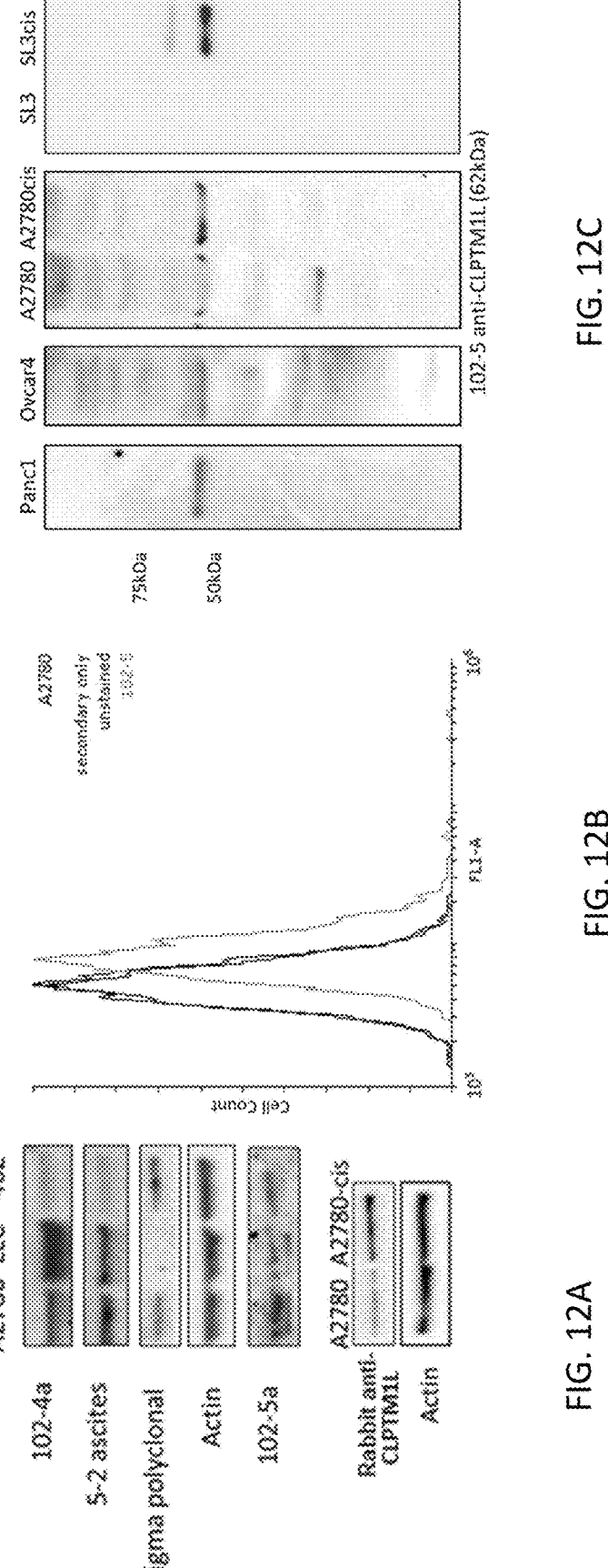
FIGS. 12A-12C demonstrate detection of CLPTM1L on tumor cells and in lysates using novel human anti-CLPTM1L antibodies. (A) Western blotting of tumor cell lysates (A2780 ovarian, LLC mouse lung, 462 primary PDAC) with mouse and human anti-CLPTM1L antibodies and relative accumulation of CLPTM1L in A2780 versus A2780-cis (cisplatin resistant) human ovarian tumor cells using commercial anti-CLPTM1L. (B) Flow cytometry on A2780 detecting cell surface CLPTM1L with 102-5 human anti-CLPTM1L. (C) Full-length western blots of Panc1 pancreatic, Ovcar4 ovarian, A2780 ovarian, and A2780-cis tumor cells with 102-5 human anti-CLPTM1L.
Figure 24:
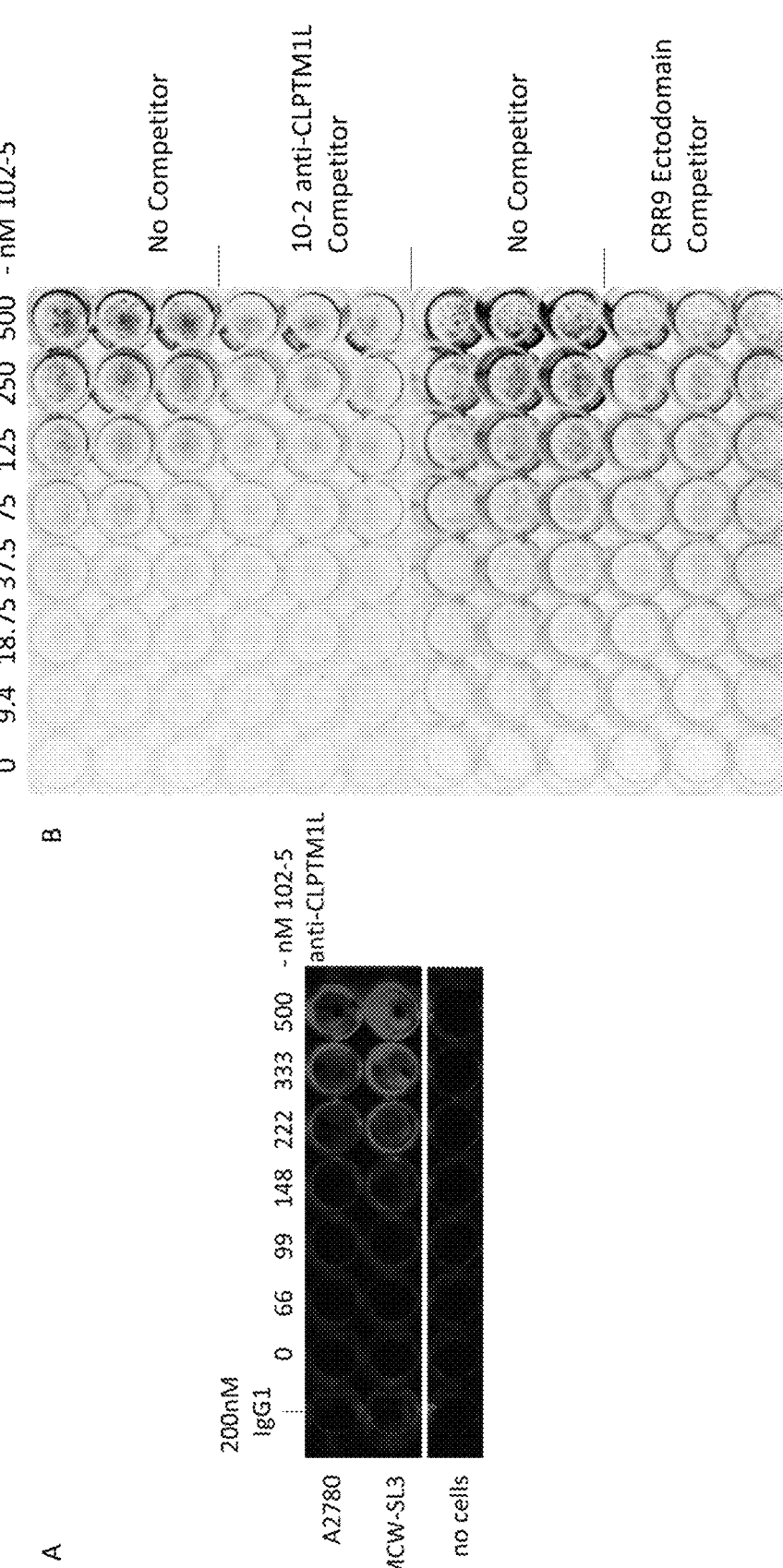
FIG. 24 demonstrates CRR9-specific binding of 102-5 to live cells using on-cell detection of fluorescently labeled 102-5 antibody binding to live Panc1 tumor cells, with or without competitors as indicated (excess 10-2 mouse ascites raised against the same epitope of CRR9 or excess purified CRR9 ectodomain).
Figure 25:
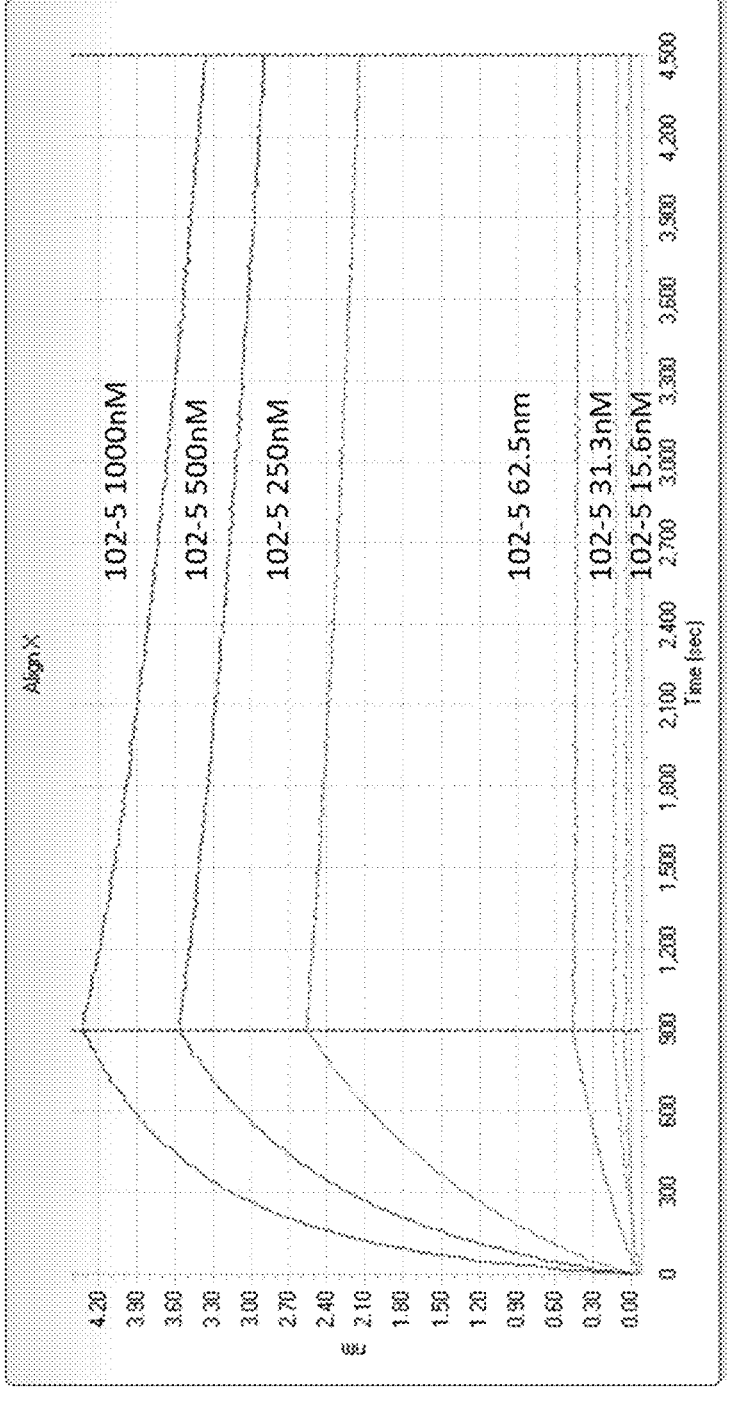
FIG. 25 presents affinity (Kd) data for antigen target binding obtained using biolayer interferometry.
Figure 27:
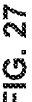
FIG. 27 demonstrates kidney and liver histology and cleaved Caspase 3 IHC (apoptosis) in C57bl/6 mice treated with 10 mg/kg ESS102-5 weekly I.P. for 35 days. No tissue toxicity was evident.
Figure 28:
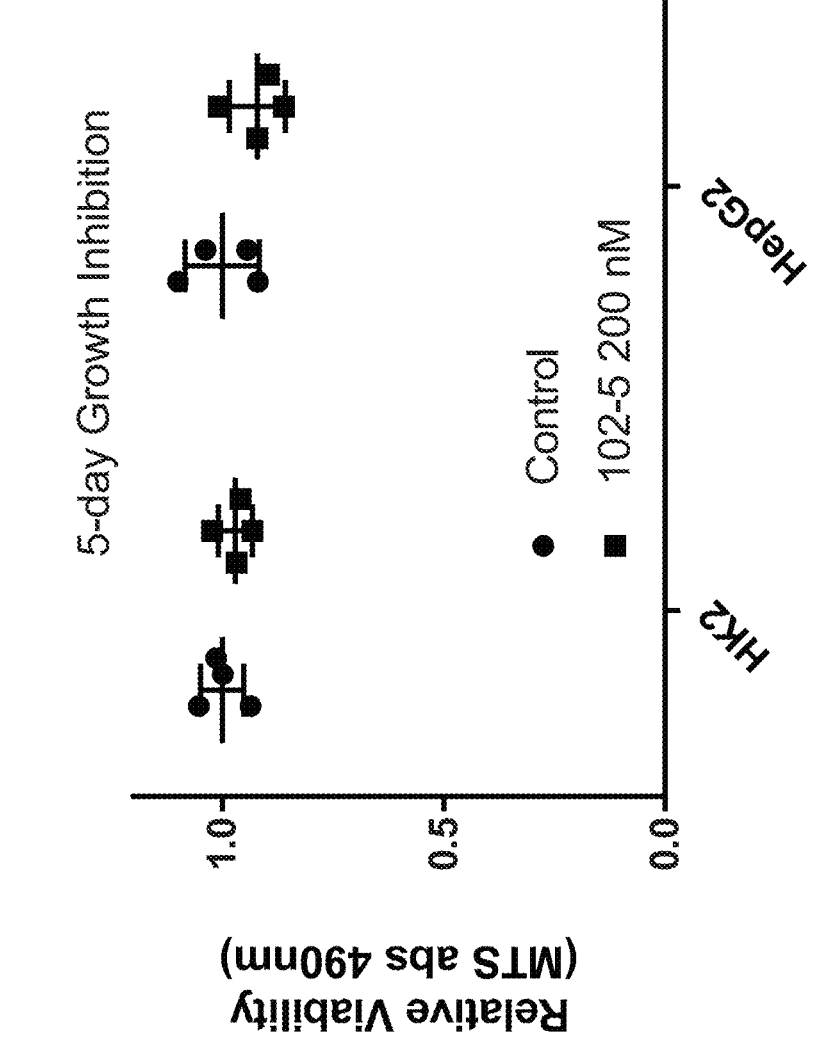
FIG. 28 demonstrates viability of HK (normal kidney) and HepG2 cells treated with vehicle control or 200 nM 102-5 for 5 days, as measured by MTT metabolic activity assay.

Immunoblotting analysis using mouse (5-2) and human anti-CLPTM1L (scFv-Fc and full-length IgG1 (4a)) as well as commercial anti-CLPTM1L polyclonal antibody demonstrate detection of CLPTM1L in human ovarian and pancreatic tumor lysates and mouse lung (LLC) tumor lysates (FIG. 12A). In contrast, commercial antibodies do not detect the mouse protein. Commercial rabbit anti-CLPTM1L detected upregulation of CLPTM1L accumulation in A2780-cis (cisplatin resistant) ovarian tumor cells compared to that in parental A2780 cells. Using flow cytometry, binding of full-length human anti-CLPTM1L (102-5) to the surface of live human ovarian tumor cells was demonstrated (FIG. 12B). Full-length western blots using 102-5 and lysates from Panc1 pancreatic, Ovcar4 human ovarian serous adenocarcinoma, and resulted in a single major band consistent with 62 kDa CLPTM1L and concurred with results using commercial anti-CLPTM1L demonstrating upregulation of CLPTM1L accumulation in A2780-cis compared to that in parental A2780 cells (FIG. 12C). Similarly, CLPTM1L expression is induced in SL3 patient-derived ovarian epithelial tumor cells that are adapted for cisplatin resistance by chronic exposure to cisplatin (FIG. 12C). On-cell western analysis also demonstrated detection of cell-surface CLPTM1L on live A2780 and MCW-SL3 cells (FIG. 24).

Figures 13A, 13B, 13C, 13D:
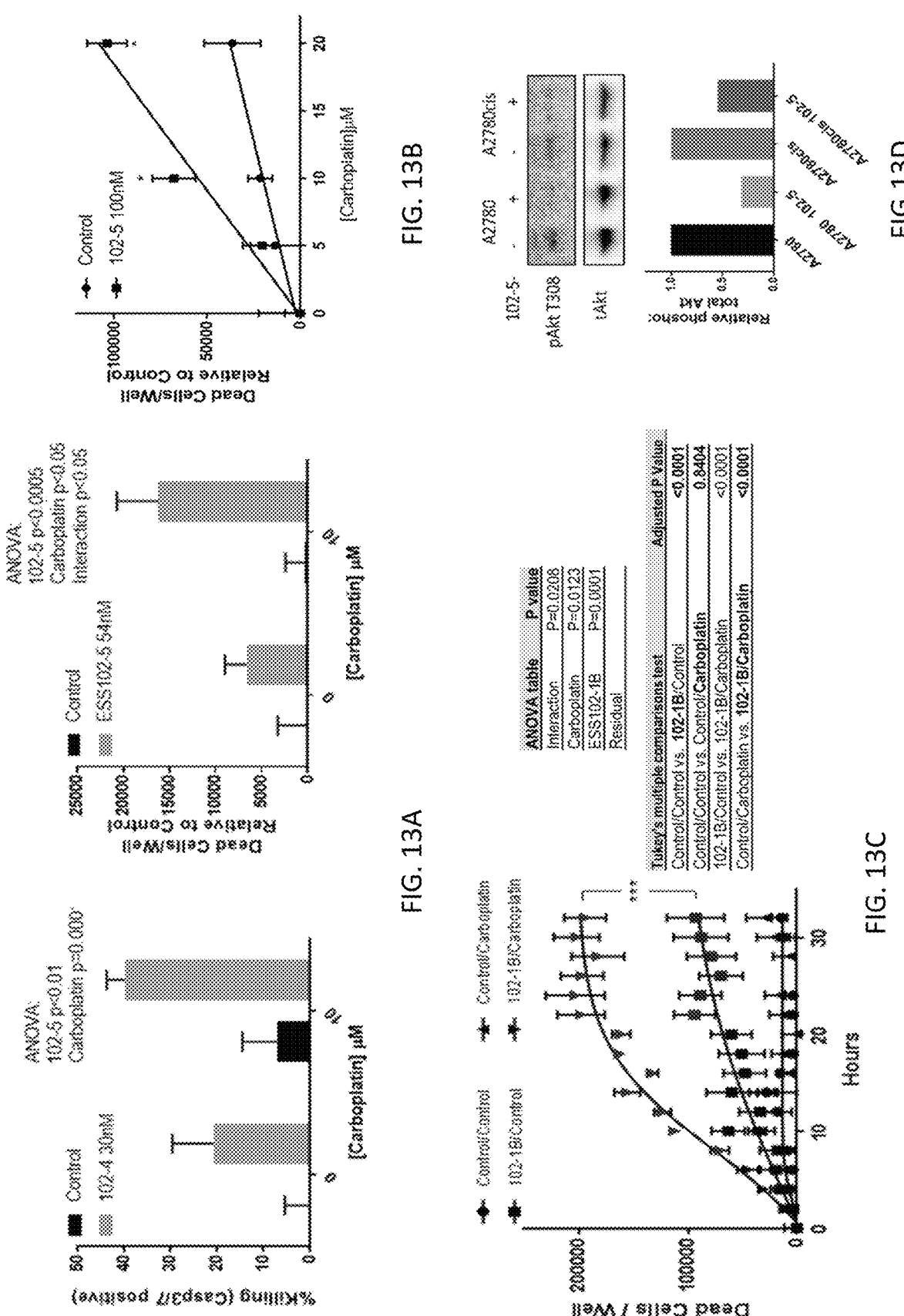
FIGS. 13A-13I demonstrate resensitization of drug resistant tumor cells to chemotherapeutic killing. (A) A2780 apoptotic killing (casp 3/7 live imaging) after 36 hour mAb treatment (scFv clones 102-4a left, 102-5a right) and 24-hour carboplatin treatment. (B) Dose-response to up to 20 μM carboplatin in resistant A2780 cells treated with either control IgG1 or 102-5, relative to 0 carboplatin controls. (C) Kinetic killing assay (live imaging) in A2780 with human anti-CLPTM1L scFv and/or 10 μM carboplatin treatment. $*p<0.05$, $p<0.005$, $*p<0.0005$. (D) Western blotting and densitometry for Akt and phospho-Akt (T308) in A2780 and A2780cis. (E) Cisplatin viability (MTT) inhibition curves for SL3 sensitive (parental) and resistant (SL3cis) tumor spheroids, pAkt (T308) and total Akt western blots on SL3 and SL3cis spheroid lysates (inset). (F) Viability (MTT) of SL3cis spheroids after 16 days of growth, treated with cisplatin and/or 102-5 anti-CLPTM1L at the indicated concentrations beginning at 4 days post-seeding. $*p<0.05$, $**p<0.005$. (G) Photomicrographs of SL3cis spheroids after 16 days of growth, treated with cisplatin and/or 102-5 anti-CLPTM1L. (H) Western blotting of SL3cis spheroid lysates for caspase cleavage and Akt phosphorylation after 16 days of growth, treated with cisplatin and/or 102-5 anti-CLPTM1L. (I) Western blotting of SL3cis monolayer cultures for phospho- and total Akt following treatment with control (PSB) or 102-5 anti-CLPTM1L at the indicated concentrations. Western blotting of SL3 patient-derived ovarian tumor cells demonstrates CRR9 and pAkt upregulation in response to chronic cisplatin exposure (data not shown).
Figures 13E, 13F, 13G, 13H, 13I:
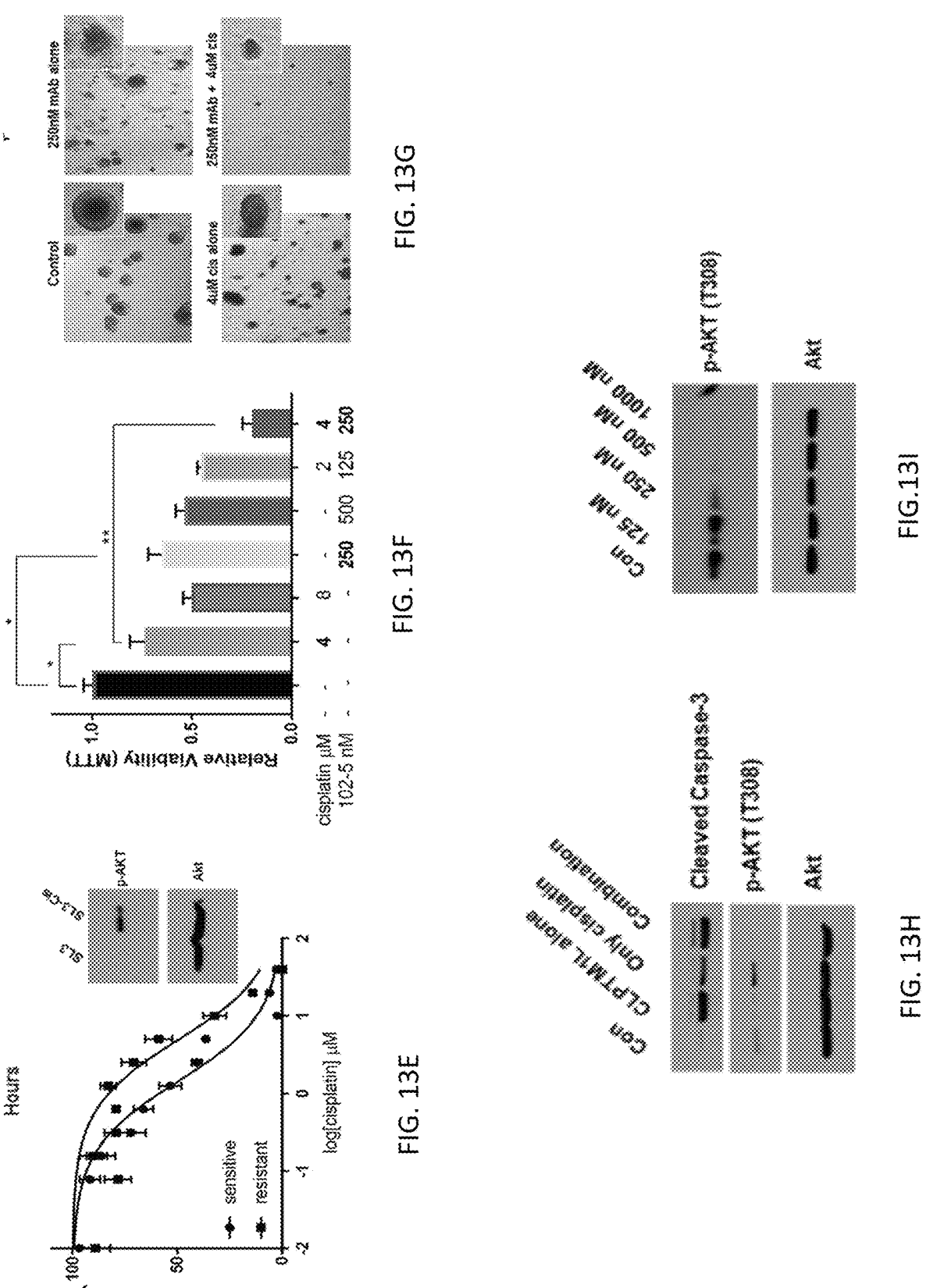
Figure 14:
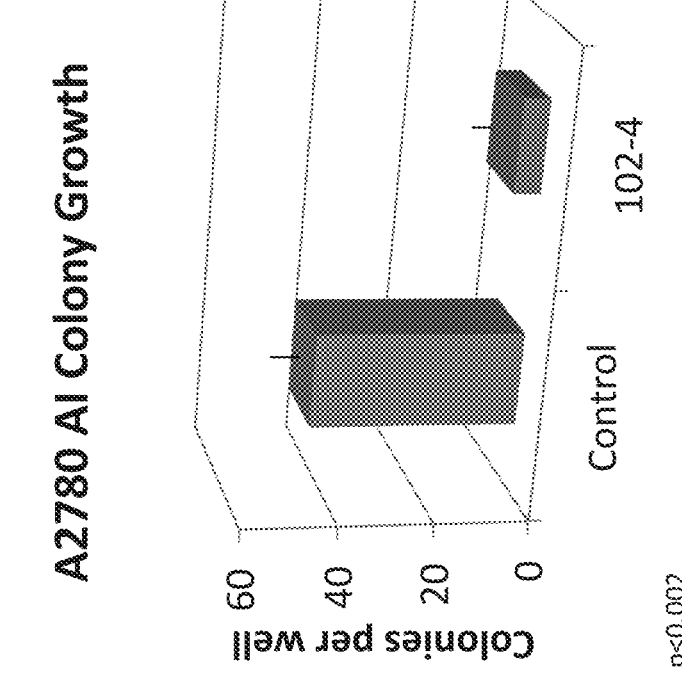
FIG. 14 demonstrates anchorage independent growth inhibition by "102" human anti-CRR9/CLPTM1L antibodies.
Figure 15:
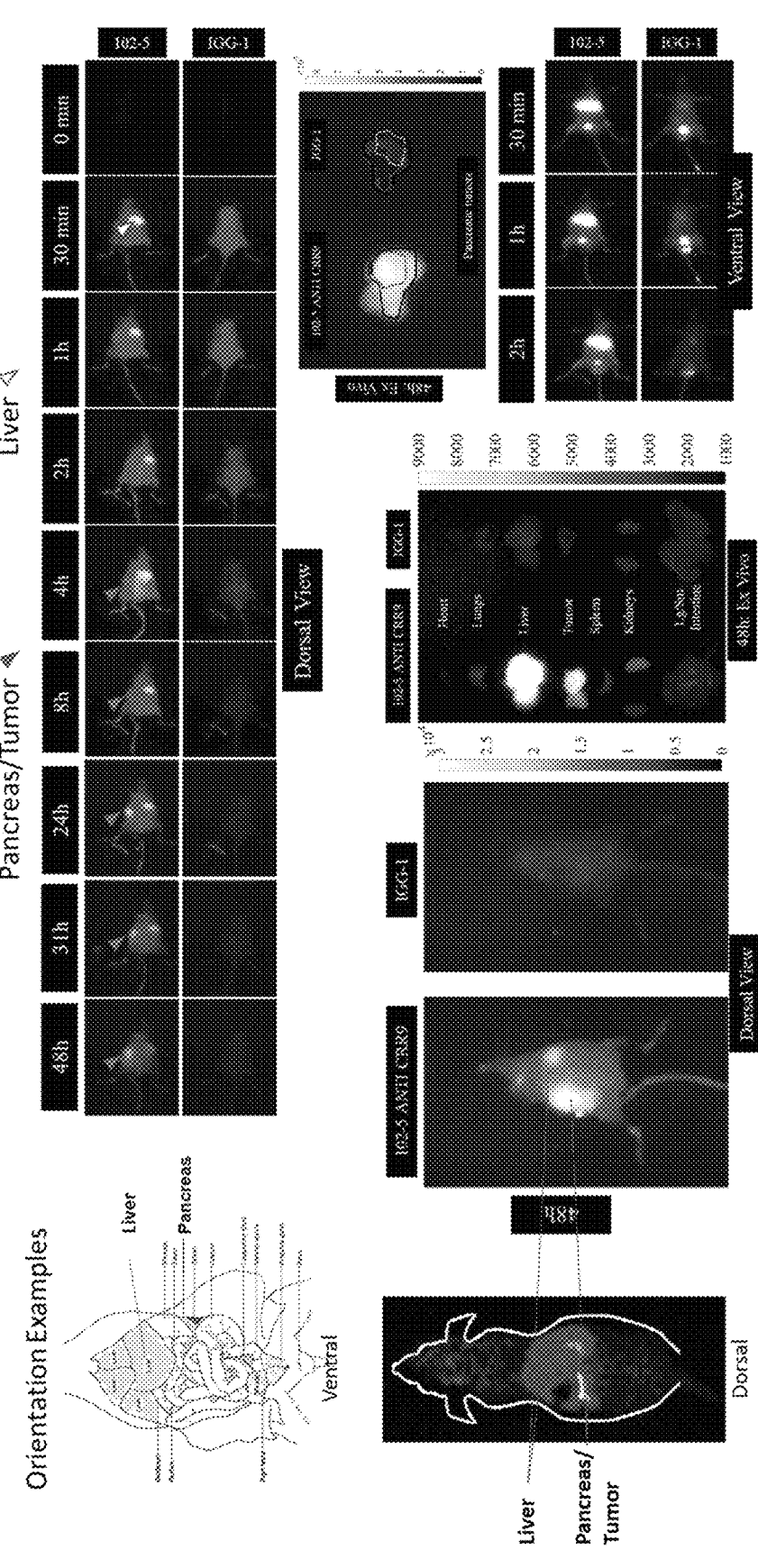
FIG. 15 demonstrates that "102" human anti-CRR9 antibodies accumulate specifically and stably in tumor tissues of a syngeneic mouse orthotopic pancreatic adenocarcinoma model.
Figure 17:
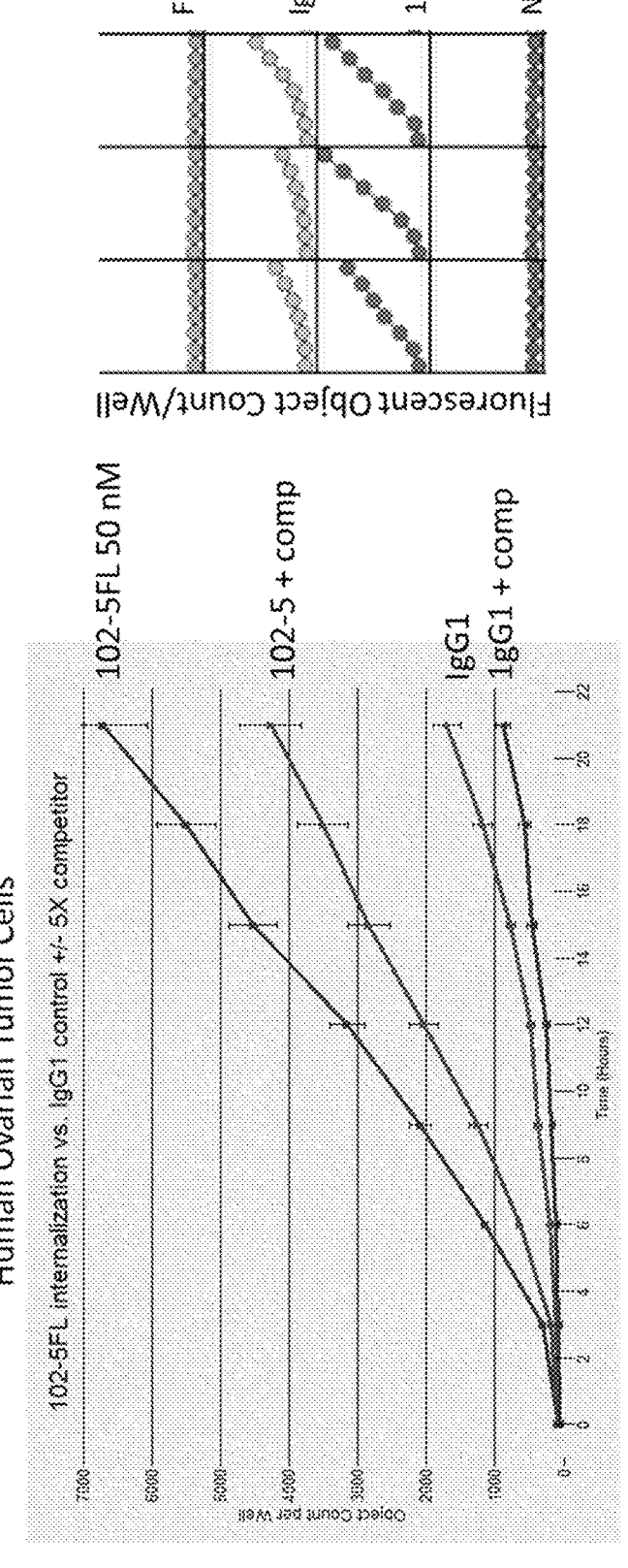
FIG. 17 demonstrates that 102-5 is internalized into ovarian tumor cells in a receptor-dependent fashion.
Figure 19:
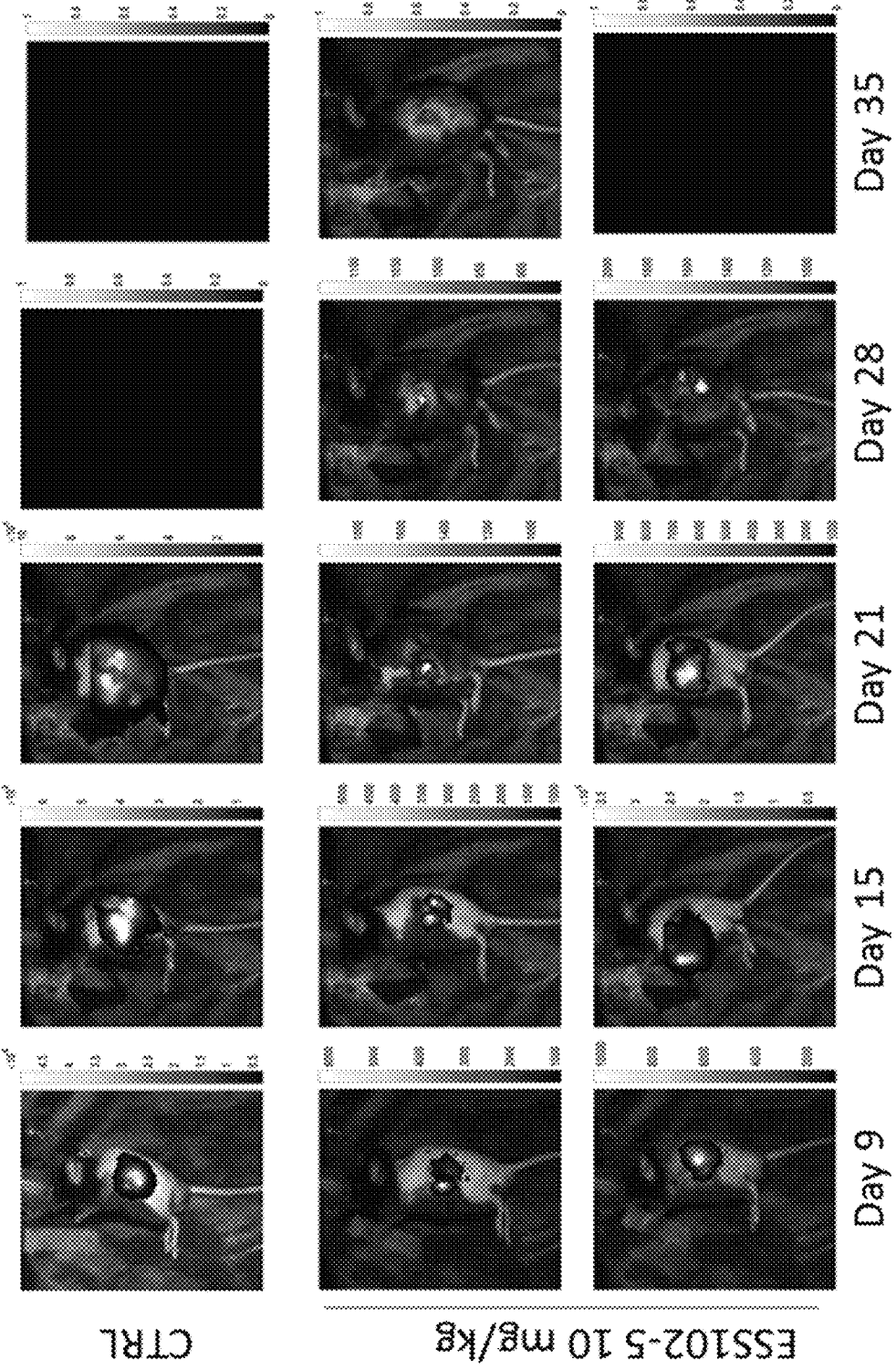
FIG. 19 demonstrates that prolonged survival was observed upon treatment with 102-5 in syngeneic orthotopic mouse models of pancreatic adenocarcinoma.
Figure 20:
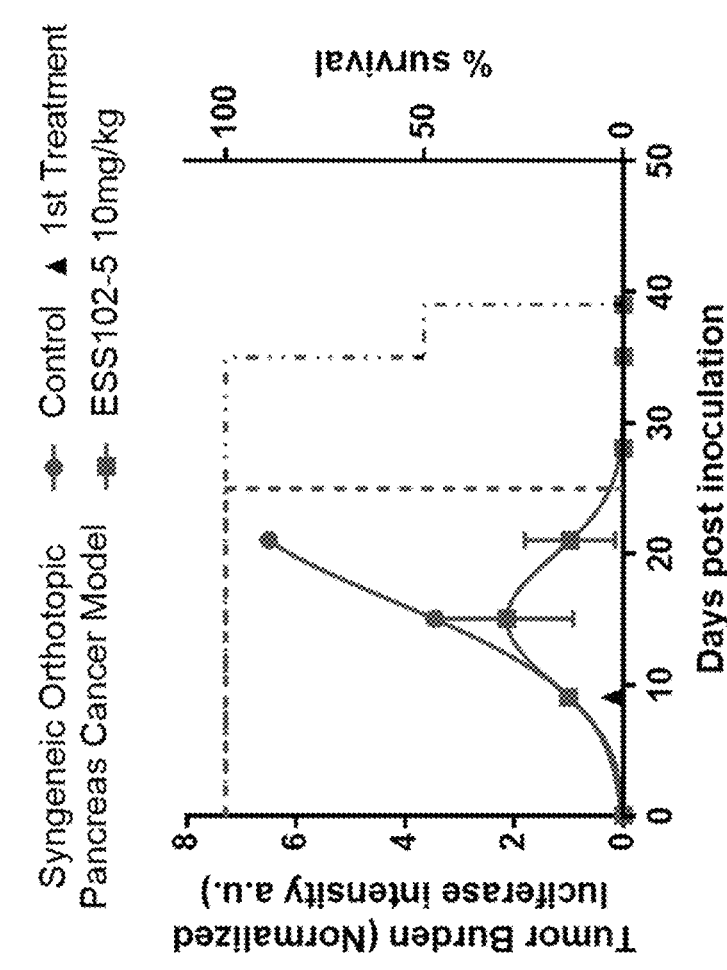
FIG. 20 demonstrates that tumor shrinkage was observed upon treatment with 102-5 in syngeneic orthotopic mouse models of pancreatic adenocarcinoma.
Figure 21:
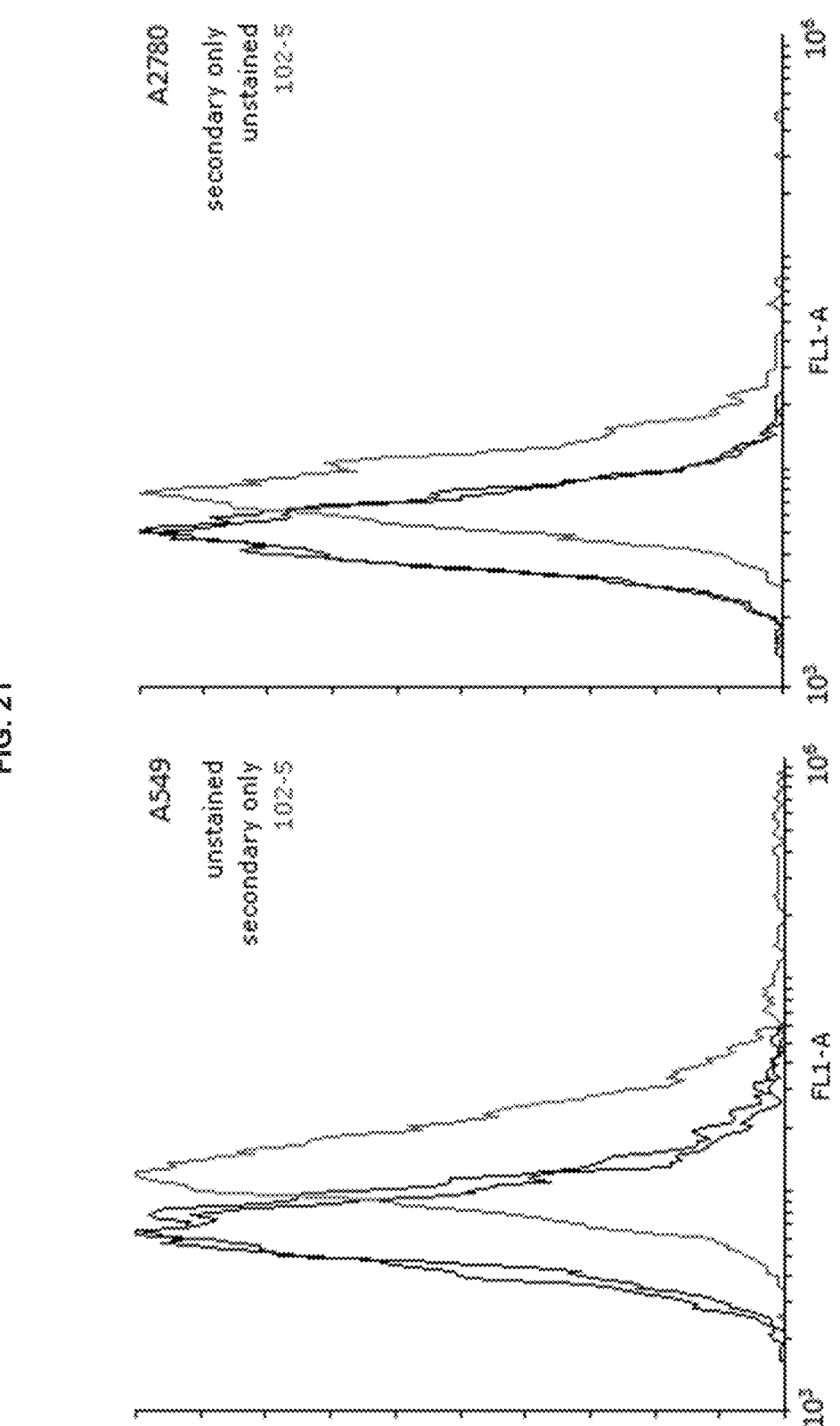
FIG. 21 shows flow cytometry data demonstrating binding of 102-5 to the surface of lung (A549) and ovarian (A2780) tumor cells, attached. Indirect flow cytometry was performed using 102-5 as a primary and anti-Human IgG (H+L) preadsorbed, alexafluor 488 conjugated secondary antibody.
Figure 22:
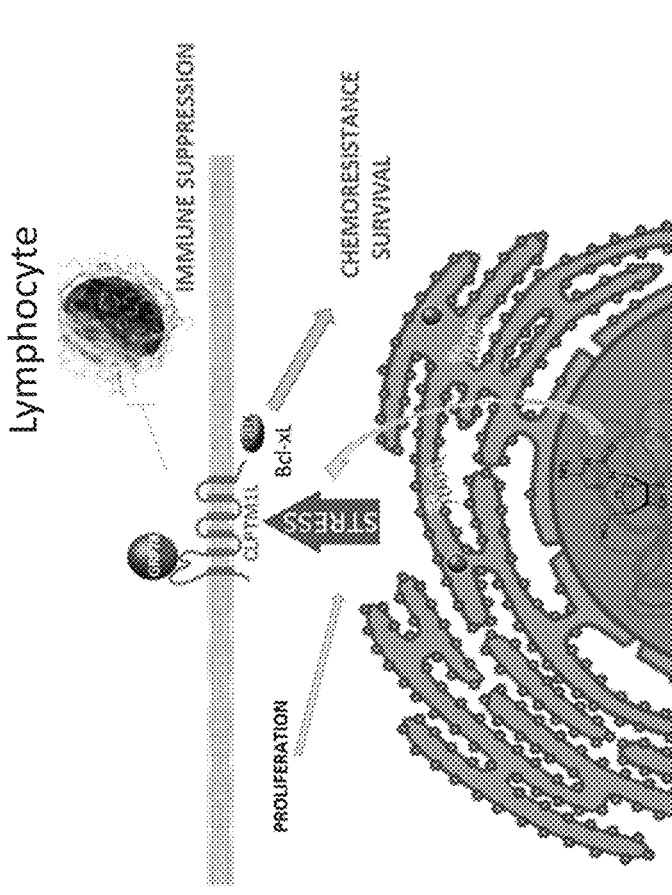
FIG. 22 is a schematic illustrating a mechanism of action for 102-5. 102-5 binds to CLPTM1L receptor and inhibits downstream survival signaling (Akt phosphorylation and Bcl-xL accumulation). This activity has been linked to anti-neoplastic activity of 102-5. We have also shown 102-5 to be internalized into human tumor cells and to cause decreased T-cell infiltration and a shift toward T-reg prevalence over CD4 T-cells in orthotopic mouse isografts models.
Figures 32A, 32B:
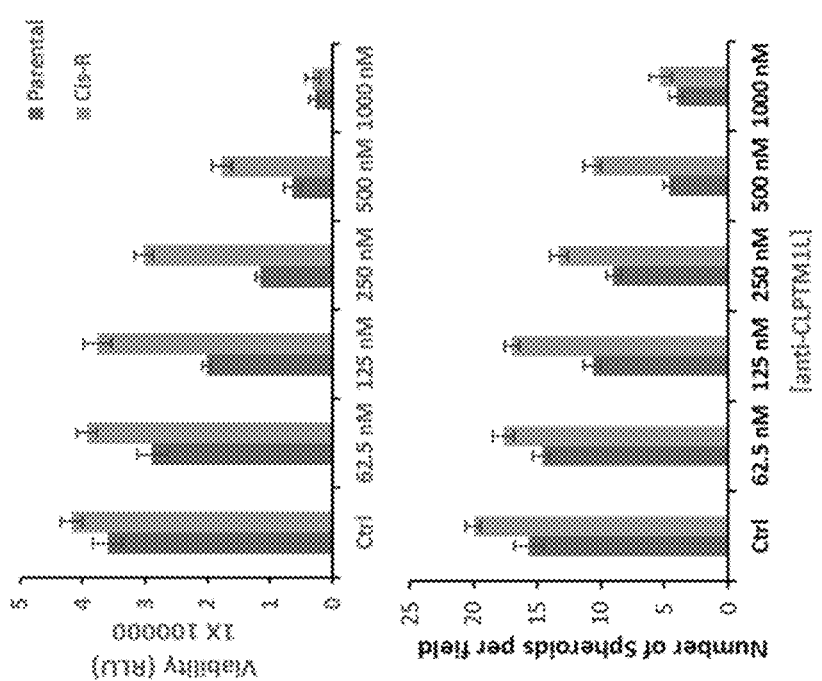
FIGS. 32A-32D demonstrate chemosensitization of ovarian tumor cells by 102-5. (A) Ovcar4 human ovarian serous adenocarcinoma cells were synergistically sensitized to carboplatin by treatment with 102-5 anti-CLPTM1L. (B) Graphs illustrate that dose-response of carboplatin killing in human ovarian tumor cells was also shifted by treatment with human anti-CLPTM1L. Re-sensitization of MCW-SL3cis cells to cisplatin killing by 102-5 anti-CLPTM1L was synergistic as measured by (C) two-way ANOVA (p<0.05) and (D) isobole and combination index (0.65).
Figure 32D:
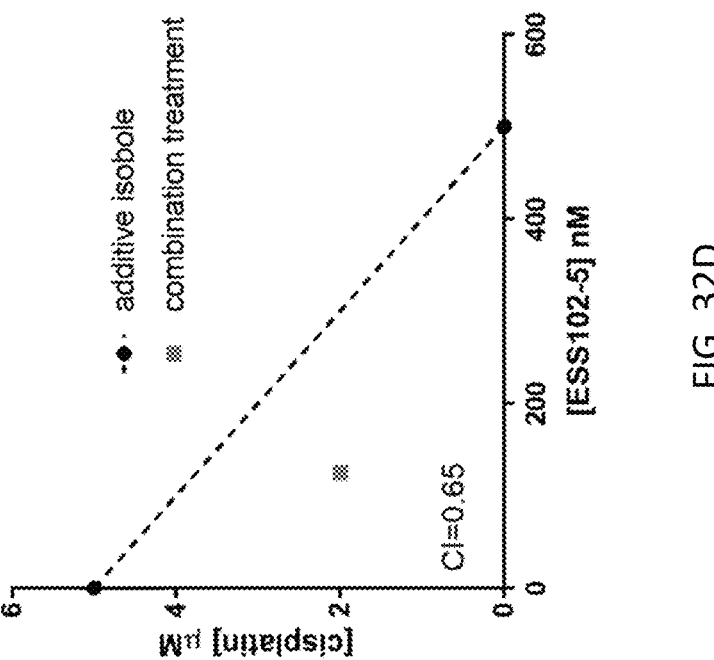
Figure 32C:
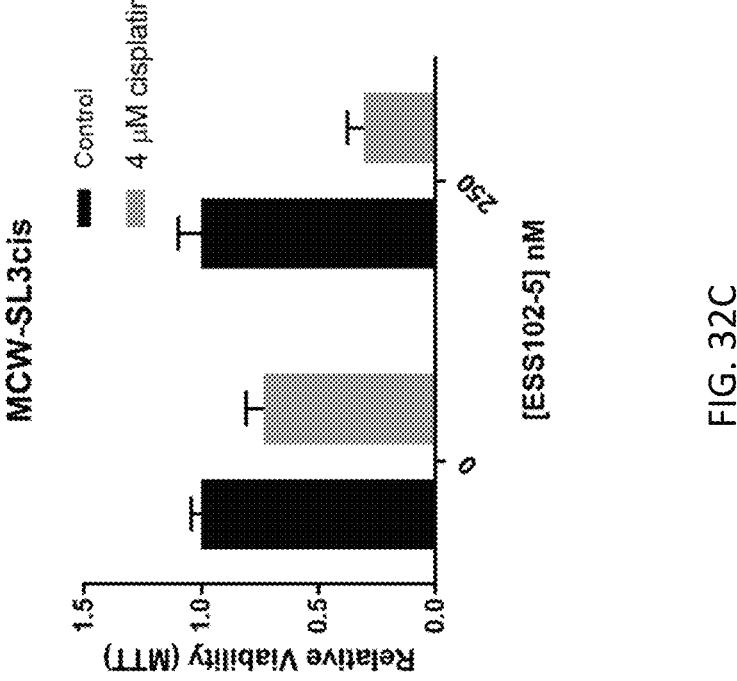

Treatment of platinum-resistant A2780 human ovarian tumor cells with either 102-5 anti-CLPTM1L increased the apoptotic killing response of 10 μM carboplatin with synergistic as determined by ANOVA (FIG. 13A). The dose-response of carboplatin killing in human ovarian tumor cells was also shifted by treatment with human anti-CLPTM1L (FIG. 13B). Live cell imaging measurement of cell death over a time course of 30 hours demonstrated killing by human anti-CLPTM1L alone but not by 10 μM carboplatin and synergistic killing by the combination of anti-CLPTM1L and carboplatin (FIG. 13C). 102-5 anti-CLPTM1L treatment resulted in decreased Akt phosphorylation at threonine 308 in both A2780 and A2780-cis (FIG. 13D). Similarly, Ovcar4 human ovarian serous adenocarcinoma cells were synergistically sensitized to carboplatin by treatment with 102-5 anti-CLPTM1L (FIG. 32A). MCW-SL3 primary, patient-derived ovarian epithelial carcinoma cells were induced to become resistant to cisplatin as described in the methods section and demonstrated in FIG. 13E (SL3cis). Like CLPTM1L induction in SL3cis (FIG. 12C), phosphorylation threonine 308 of Akt was increased in SL3cis compared to that in parental SL3 cells (FIG. 13E). Treatment of cisplatin resistant MCW-SL3cis cells with 102-5 anti-CLPTM1L abrogated resistance to cisplatin in a dose-dependent manner as measured by spheroid viability, size, and number over 16 days in culture with cisplatin and anti-CLPTM1L treatment beginning at day 4 in culture (FIGS. 13F, 13G, FIG. 32C). While anti-CLPTM1L treatment alone was sufficient to inhibit anchorage independent growth of MCW-SL3cis and parental MCW-SL3 cells in a dose-dependent manner (FIG. 32B) (ANOVA p<0.0005), re-sensitization of MCW-SL3cis cells to cisplatin killing by 102-5 anti-CLPTM1L was synergistic as measured by two-way ANOVA (p<0.05) and isobole combination index (0.65) (FIGS. 13F, 13G, FIGS. 32C, 32D). Caspase-3 cleavage was induced by both cisplatin treatment and 102-5 anti-CLPTM1L treatment, with signal being stronger in lysates from anti-CLPTM1L-treated SL3cis spheroids compared to cisplatin-treated spheroids (FIG. 13H). Akt phosphorylation at threonine 308 was induced by cisplatin treatment but abrogated by 102-5 anti-CLPTM1L treatment in these spheroids (FIG. 13H). In monolayer cultures of SL3cis cells, 102-5 anti-CLPTM1L treatment resulted in a dose-dependent inhibition of Akt phosphorylation at threonine 308 (FIG. 13I).

CLPTM1L Ectodomain-Dependent Intercellular Chemoresistance and its Inhibition by CLPTM1L mAb In human lung tumor cells expressing cell-surface CLPTM1L (FIG. 29A), treatment with supernatants from cells that had been pre-treated with cisplatin conferred protection from cisplatin toxicity, regardless of whether the cells producing the supernatant were wild-type or CLPTM1L knockdown cells (FIG. 29B, left). However, in cells depleted of CLPTM1L by knockdown, cytoprotection from cisplatin was dependent on CLPTM1L expression in the supernatant-producing cells (FIG. 29B, right). Likewise, conditioned supernatants from cells overexpressing CLPTM1L (Panc1-CLPTM1L) were protective against 100 nM gemcitabine killing compared to control supernatants with vector alone (Panc1-Vec) (FIG. 29C). The cytoprotective effect was greatly enhanced with supernatants from cells that were pre-treated with gemcitabine regardless of CLPTM1L overexpression. Human ovarian tumor cells also demonstrated resistance to carboplatin conferred by conditioned media from carboplatin-treated cells (FIG. 29D). Chemoresistance conferred by conditioned supernatants was abrogated by pre-treatment of the supernatants with human anti-CLPTM1L 102-5.

CLPTM1L in Extracellular Vesicles

Figures 30A, 30B, 30C, 30D:
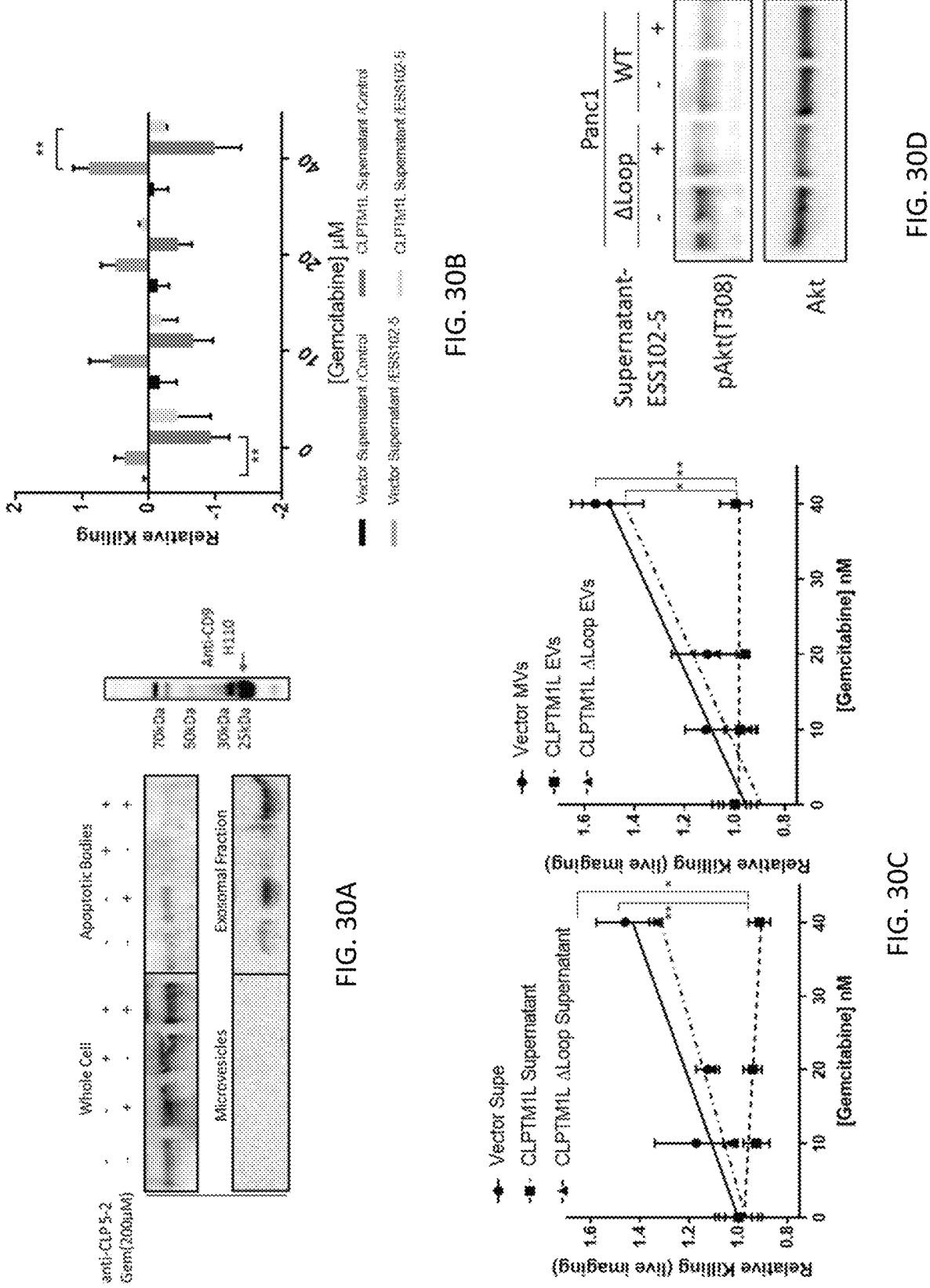
FIGS. 30A-30F demonstrate 102-5 inhibition of chemo-protection by extracellular vesicle- and supernatant-associated CLPTM1L ectodomain. (A) Western blotting of whole-cell, apoptotic bodies, extracellular vesicles, and microvesicles isolated from Panc1 cells treated with vehicle control or 200 nM gemcitabine. (B) Relative killing (live imaging cytotoxicity) of Panc1 cells treated for 48 hours with −40 nM gemcitabine and culture supernatants from donor cells with vector control or overexpressing CLPTM1L. (C) Relative killing (live imaging cytotoxicity) of Panc1 cells treated with 0-40 nM gemcitabine and culture supernatants (1:1 mix with fresh media) (top panel) or 25 μL extracellular vesicles (EVs) (ExoQuick exosomal fraction) per mL of media (bottom) from Panc1 donor cells with vector control, CLPTM1L overexpression, or CLPTM1L ectodomain deletion mutant (CLPTM1L ALoop) overexpression. (D) Western blotting of Panc1 lysates treated as above with the indicated supernatants and/or 102-5 anti-CLPTM1L for phospho-Akt (T308) and total Akt. (E) Characterization of extracellular vesicles isolated from human serum by ultra-centrifugation by western blotting for exosomal markers CD9 and CD63, and for CLPTM1L using 102-5 antibody (left); and by transmission electron microscopy (right). Scale bar=500 nM. (F) Relative killing of A2780 ovarian tumor cells treated with either vehicle control, human serum extracellular vesicles, or human serum extracellular vesicles pretreated for 24 hours with 200 nM 102-5, and then treated with 40 μM carboplatin for 4 days. *p<0.05.

CLPTM1L was present in the extracellular vesicle fraction of Panc1 pancreatic tumor cell culture media and its abundance increased in the extracellular vesicle fraction upon treatment of cultures with gemcitabine (FIG. 30A). A weaker signal for CLPTM1L was obtained in the apoptotic body fraction of culture supernatants, which was decreased upon treatment with anti-CLPTM1L. Treatment of human pancreatic tumor cells with full-length human anti-CLPTM1L 102-5 resulted in sensitization to gemcitabine killing. 102-5 also abrogated the cytoprotection conferred by supernatants, particularly those from CLPTM1L-overexpressing cells (FIG. 30B). This cytoprotection was ablated by pre-treatment of the conditioned supernatants with human anti-CLPTM1L 102-5.

Figure 30F:
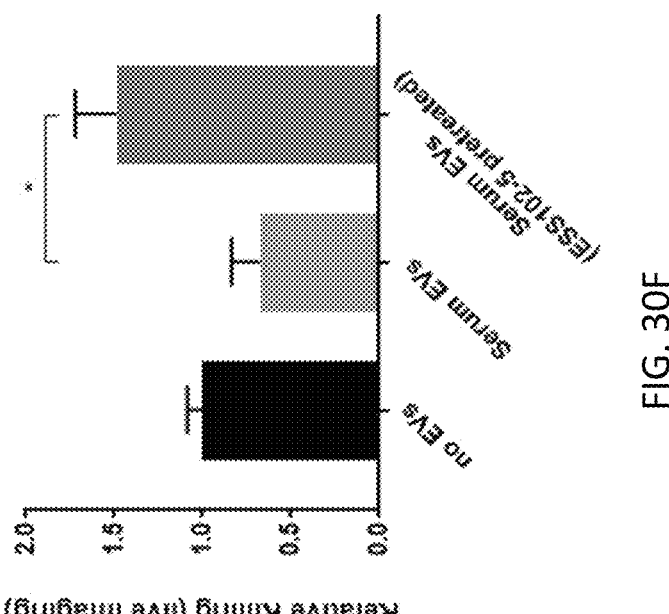
Figure 30E:
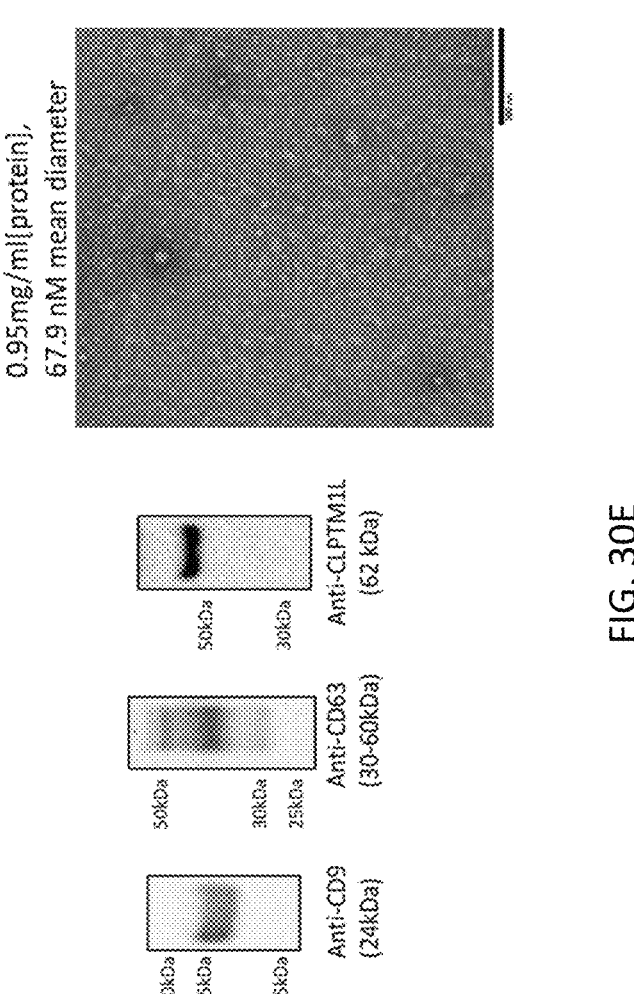
Figure 33:
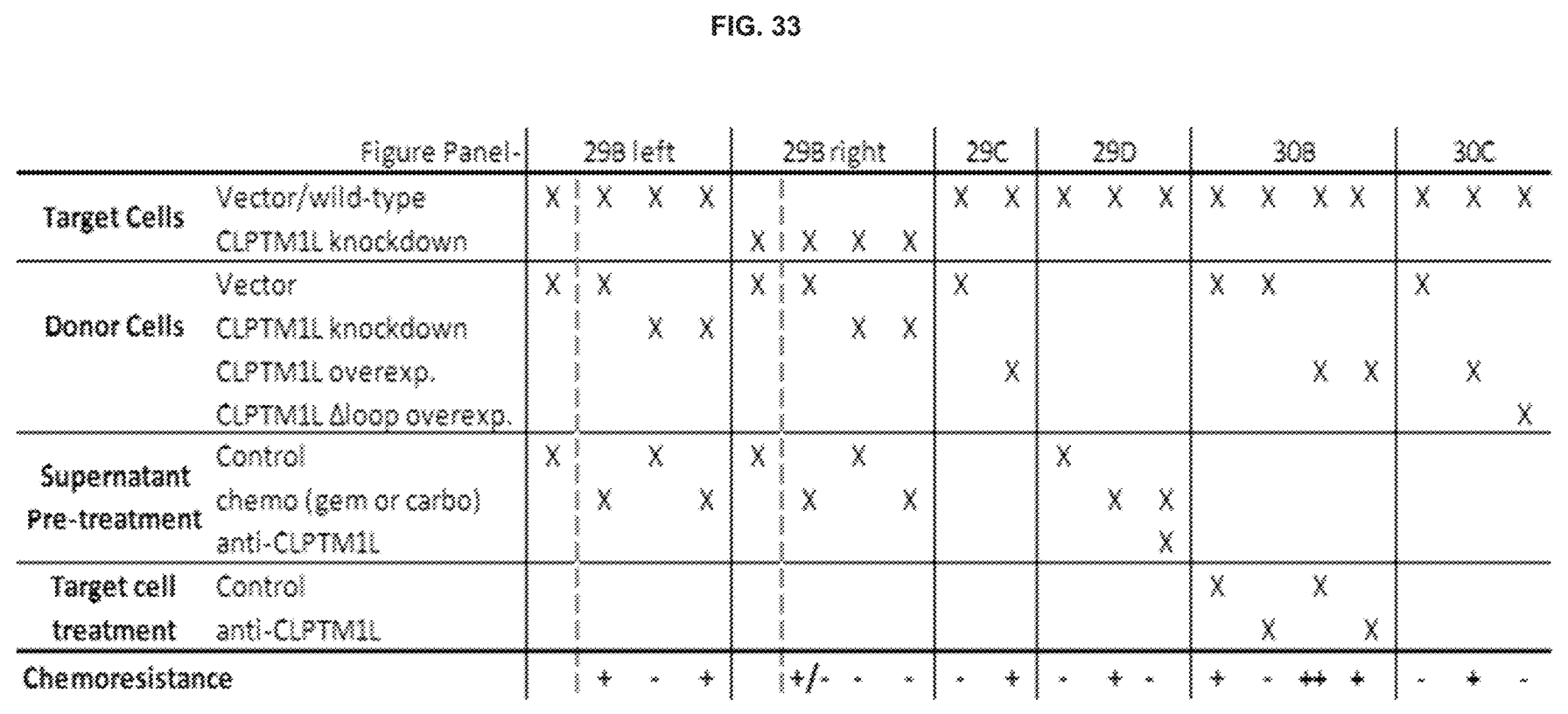

Cytoprotection from gemcitabine killing by either culture supernatants (FIG. 30C, left panel) or extracellular vesicles isolated using ExoQuick (FIG. 30C, right panel) from CLPTM1L overexpressing Panc1 cells was dependent on the ectodomain of the exogenously expressed CLPTM1L (FIG. 30C). Regardless of the presence of the ectodomain, inhibition of CLPTM1L using 102-5 resulted in decreased Akt phosphorylation at threonine 308 (FIG. 30D). Panc1 cells treated with supernatants from cells overexpressing wild-type CLPTM1L were protected from gemcitabine killing at concentrations up to 40 nM, while those treated with no supernatant or supernatants from vector or CLPTM1L exodomain deletion mutant (CLTPMIL ALoop) exhibited statistically similar dose-dependent gemcitabine killing. Results demonstrating the effect of extracellular CLPTM1L on chemosensitivity are summarized in Table 6. Extracellular vesicles isolated from human serum by ultracentrifugation and characterized by CD9 and CD63 expression and transmission electron microscopy contained CLPTM1L as detected by western blot (FIG. 30D). Carboplatin killing of A2780 ovarian tumor cells treated with serum extracellular vesicles trended lower compared to those not treated with extracellular vesicles (FIG. 30E). Pre-treatment of serum extracellular vesicles with 102-5 anti-CLPTM1L abrogated resistance to carboplatin with significantly increased killing compared to vesicles that were not pre-treated (FIG. 30E). FIG. 33 provides a table summarizing chemosensitivity data from FIGS. 29 and 30.

Figure 31B:
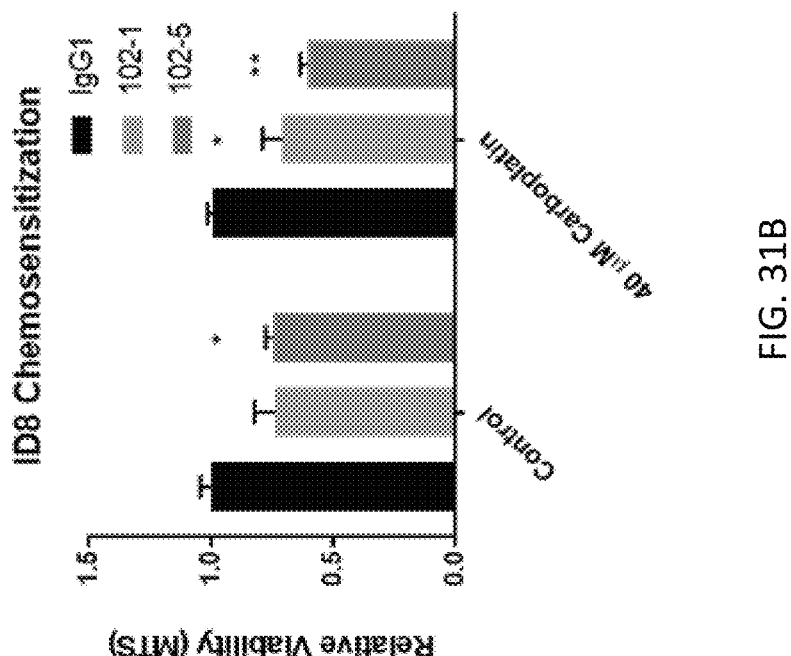
Figure 31A:
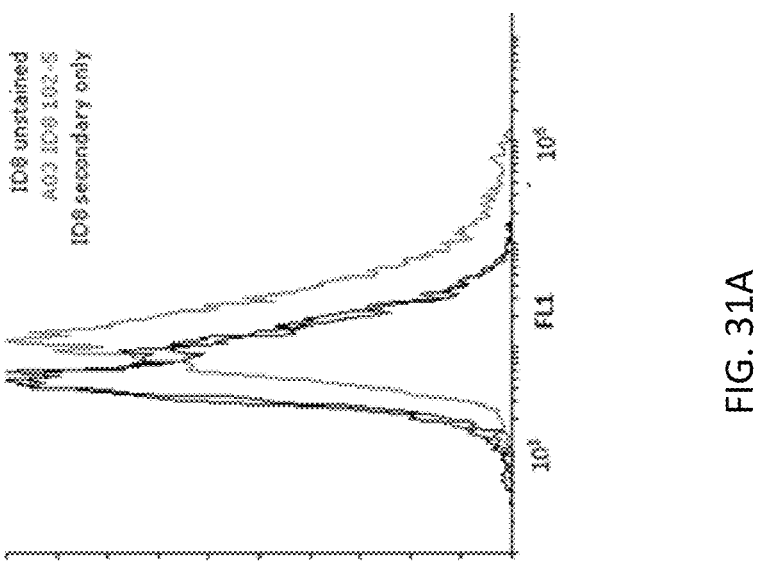

Anti-CLPTM1L Inhibition of Disseminated Ovarian tumorigenesis in an Syngeneic-Orthotopic and Xenograft Models Having demonstrated sensitization of tumor cells to genotoxic chemotherapeutic agents and tumoricidal activity by CLPTM1L inhibition, we sought to determine if anti-CLPTM1L mAb treatment could inhibit ovarian carcinoma in a relevant murine model. With disseminated peritoneal disease being the most common presentation upon recurrence of ovarian carcinoma, we utilized an orthotopic isograft model of disseminated peritoneal ovarian cancer. Human anti-CLPTM1L binding to luciferase-expressing ID8 ovarian tumor cells (ID8-luc) was detected by flow cytometry (FIG. 31A). Treatment of ID8-luc cells in vitro resulted in decreased viability (ANOVA p<0.0001) and increased carboplatin killing (ANOVA p<0.05) over 5 days in culture (FIG. 31B). ID8-luc cells were injected intraperitoneally into syngeneic C57bl/6 mice. Tumor load was monitored by luciferin luminescence using whole body imaging. Treatment of mice (weekly, I.P.) with 10 mg/kg 102-5 anti-CLPTM1L resulted in inhibition of tumor growth over 8 weeks (FIG. 31C). Control mice had an average increase in tumor load of 2.45-fold at day 42, while 102-5-treated mice had an average of 0.90-fold relative tumor load at day 42 (T-test p<0.005) (Paired t-test across time points, p=0.001). This anti-tumorigenic activity was similar to that of 10 mg/kg carboplatin administered weekly for three consecutive weeks (FIG. 31D). With combination treatments of carboplatin following anti-CLPTM1L treatment, tumor load was decreased (0.23 fold) over 35 days compared to mice treated with carboplatin alone, in which tumor load increased slightly by an average of 1.23 fold (T-test p<0.05) (FIG. 31D).

Figure 31F:
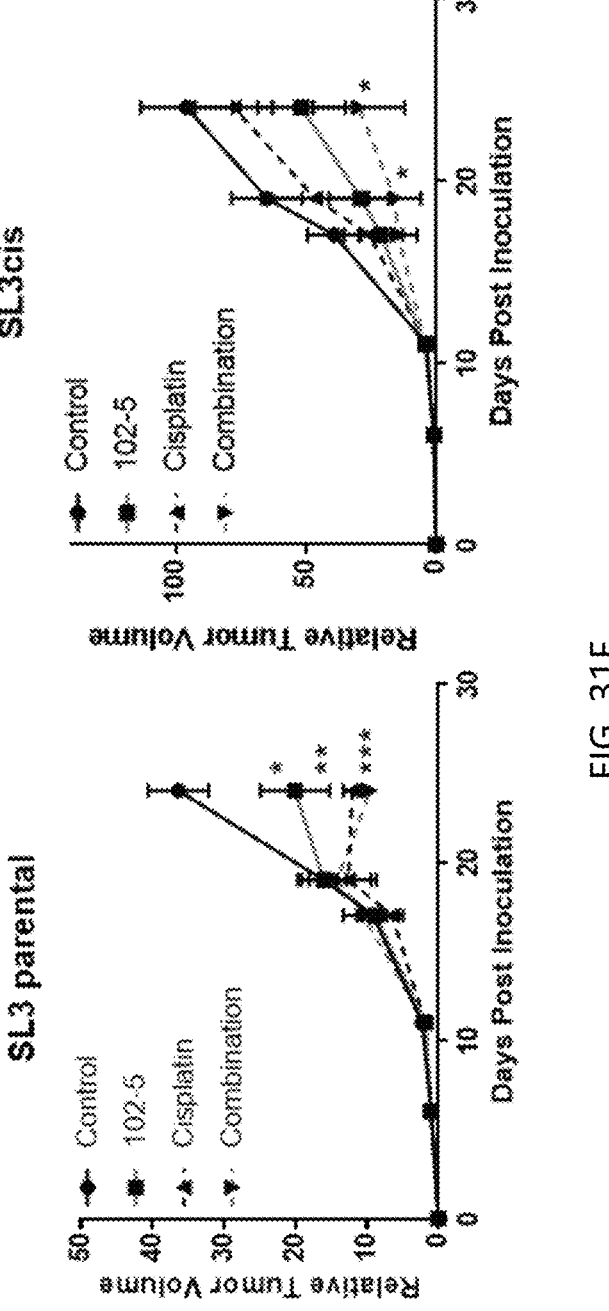

J/NU mice xenografted with SL3 parental or SL3-cis platinum resistant cells were treated weekly with control vehicles, 2.5 mg/kg cisplatin, and/or 5 mg/kg 102-5 anti-CLPTM1L. The effects of cisplatin and those of 102-5 on cisplatin treatment were investigated in this model rather than those of carboplatin since the SL3cis line was developed specifically as a cisplatin resistant line. Tumor growth and volumes, monitored over 24 days post-inoculation, were significantly inhibited by both cisplatin and 102-5 either as individual monotherapies or as a combination (FIGS. 31E, 31F). In SL3-cis platinum resistant xenografts, cisplatin significantly inhibited tumor growth only in combination therapy with 102-5 anti-CLPTM1L.

Discussion

The identity of CLPTM1L as a true oncofetal protein is gaining credence with the accumulation of knowledge regarding the pathologic function of the protein and recent evidence of fetal development function in genetically engineered CLPTM1L knockout mice (13). CLPTM1L anti-apoptotic properties may be critical during fetal development as both CLPTM1L and family member CLPTM1 have been implicated in cleft lip and palate syndrome (19, 20). In adult animals, cell-surface expression of CLPTM1L is restricted to iPS, ePS, and malignant cell populations (14, 21). Numerous consortia have demonstrated common over-expression of CLPTM1L in a variety of tumor types (2, 10-13, 15, 16, 22). High expression of CLPTM1L and CLPTM1L expression-controlling polymorphisms (23) in tumors are associated with poor prognosis as described here and previously in (24). The function of CLPTM1L is best understood in the context of anti-apoptotic activity (2, 10-12, 16, 17, 25).

Restriction of CLPTM1L surface expression to stem cell populations (14, 21) and tumor cells presents the potential to target quiescent residual tumor cells and to eliminate inherent or acquired resistance to multiple chemotherapeutic drugs. Therefore, CLPTM1L inhibition may be an attractive approach to adjunctive and/or maintenance therapy in ovarian cancer. Here we have demonstrated robust inhibition of tumorigenesis and sensitization of tumors to chemotherapeutic killing using anti-CLPTM1L monoclonal antibodies, which can also be achieved using shRNA depletion (10, 11). The restoration of platinum sensitivity in a patient-derived cisplatin-resistant xenografts as demonstrated in this study is notable. In the present study, we demonstrate that CLPTM1L accumulation is up-regulated in platinum resistant derivatives of human ovarian tumor cells. This did not correlate with higher Akt phosphorylation, although 102-5 anti-CLPTM1L did decrease Akt phosphorylation. The effect of 102-5 on Akt phosphorylation in A2780 cells could potentially be a result of off-target effects; however, shRNA depletion of CLPTM1L also decreases Akt phosphorylation, which is mechanistically linked to oncogenic transformation (10). Targeted therapies such as PARP and VEGF inhibitors are currently being used in ovarian cancer in the adjuvant setting and have been recently investigated in a maintenance therapy setting, although PARP inhibition may only be effective in a small subset of patients, for example those with homologous DNA damage repair defects (BRCA). VEGF inhibition has exhibited modest effect on overall survival.

Potentiation of genotoxic killing of tumors using chemotherapy drugs such as carboplatin using CLPTM1L inhibitors may be practical approach to mitigating therapy resistance in ovarian cancer. Equal protection from genotoxic killing by CLPTM1L supernatants and extracellular vesicles fractions in a CLPTM1L ectodomain-dependent manner is strong evidence that CLPTM1L in extracellular vesicles is indeed responsible for an observed transfer of cytoprotection by supernatants from CLPTM1L-expressing cultures. Treatment of tumor cells with supernatant from wild-type CLPTM1L overexpressing cells did not increase phosphorylation of Akt compared to those treated with supernatants from ALoop CLPTM1L overexpressing cells. However, inhibition of CLPTM1L decreased Akt phosphorylation in cells treated with both wild-type CLPTM1L and ALoop CLPTM1L. This suggests that while endogenous CLPTM1L may contribute to Akt phosphorylation in A2780 ovarian tumor cells, Akt phosphorylation may not a mechanism of chemoresistance conferred by delivery of CLPTM1L from extracellular sources.

Tumor-derived extracellular vesicles have been previously shown to mediate resistance to chemotherapy in bystander cells, including in ovarian cancer (26-28). Exosomes were found to promote an EMT phenotype, which may contribute to resistance (26). Interestingly, CLPTM1L interacting protein and ER-stress survival effector GRP78 can promote EMT in cancer (29). The role of PM or extracellular CLPTM1L in EMT in cancer is a provocative subject of further research. While increased CLPTM1L in the extracellular vesicles fraction of treated patients may be the result of generally increased vesicle shedding by tumor cells, we have demonstrated the concept that extracellular CLPTM1L can transfer chemoresistance. There are clearly secreted factors other than CLPTM1L that are induced by chemotherapeutic insult, as demonstrated by cytoprotection of CLPTM1L expressing cells by both vector control and CLPTM1L shRNA supernatants in (FIG. 29B). We have shown that in tumor cells depleted of CLPTM1L, intercellular CLPTM1L from supernatants becomes important for cytoprotection against chemotherapeutic toxicity. The abundance of CLPTM1L in the apoptotic body fraction was decreased upon anti-CLPTM1L treatment (FIG. 30A), supporting the concept of depletion of surface-CLPTM1L by anti-CLPTM1L monoclonal antibodies as described in Clarke et al. (2). The absence of an effect of anti-CLPTM1L on CLPTM1L abundance in extracellular vesicles may be due to internalization and incorporation of CLPTM1L into endosomes upon mAb treatment.

REFERENCES

1. Pommier A, Anaparthy N, Memos N, Kelley Z L, Gouronnec A, Yan R, et al. Unresolved endoplasmic reticulum stress engenders immune-resistant, latent pancreatic cancer metastases. Science. 2018; 360 (6394).
2. Clarke W R, Amundadottir L, James M A. CLPTM1L/CRR9 Ectodomain Interaction with GRP78 at the Cell Surface Signals for Survival and Chemoresistance upon ER Stress in Pancreatic Adenocarcinoma Cells. Int J Cancer. 2018.
3. Gifford J B, Huang W, Zeleniak A E, Hindoyan A, Wu H, Donahue T R, et al. Expression of GRP78, Master Regulator of the Unfolded Protein Response, Increases Chemoresistance in Pancreatic Ductal Adenocarcinoma. Mol Cancer Ther. 2016; 15 (5):1043-52.
4. Wang L, Zhang Y, Wang W, Zhu Y, Chen Y, Tian B. Gemcitabine treatment induces endoplasmic reticular (ER) stress and subsequently upregulates urokinase plasminogen activator (uPA) to block mitochondrial-dependent apoptosis in Panc-1 cancer stem-like cells (CSCs). PLOS One. 2017; 1 (8):e0184110.

5. Thakur P C, Miller-Ocuin J L, Nguyen K, Matsuda R, Singhi A D, Zeh H J, et al. Inhibition of endoplasmic-reticulum-stress-mediated autophagy enhances the effectiveness of chemotherapeutics on pancreatic cancer. J Transl Med. 2018; 16(1):190.

6. Santos J C, Lima N D S, Sarian L O, Matheu A, Ribeiro M L, Derchain S F M. Exosome-mediated breast cancer chemoresistance via miR-155 transfer. Sci Rep. 2018; 8(1):829.

7. Sharma A. Chemoresistance in cancer cells: exosomes as potential regulators of therapeutic tumor heterogeneity. Nanomedicine (Lond). 2017; 12(17):2137-48.

8. Patel G K, Khan M A, Bhardwaj A, Srivastava S K, Zubair H, Patton M C, et al. Exosomes confer chemoresistance to pancreatic cancer cells by promoting ROS detoxification and miR-155-mediated suppression of key gemcitabine-metabolising enzyme, DCK. Br J Cancer. 2017; 116(5):609-19.

9. Qiu J, Yang G, Feng M, Zheng S, Cao Z, You L, et al. Extracellular vesicles as mediators of the progression and chemoresistance of pancreatic cancer and their potential clinical applications. Mol Cancer. 2018; 17(1):2.

10. James M A, Vikis H G, Tate E, Rymaszewski A L, You M. CRR9/CLPTM1L regulates cell survival signaling and is required for Ras transformation and lung tumorigenesis. Cancer Res. 2014; 74(4):1116-27.

11. James M A, Wen W, Wang Y, Byers L A, Heymach J V, Coombes K R, et al. Functional characterization of CLPTM1L as a lung cancer risk candidate gene in the 5p15.33 locus. PLOS One. 2012; 7(6):e36116.

12. Puskas L G, Man I, Szebeni G, Tiszlavicz L, Tsai S, James M A. Novel Anti-CRR9/CLPTM1L Antibodies with Antitumorigenic Activity Inhibit Cell Surface Accumulation, PI3K Interaction, and Survival Signaling. Mol Cancer Ther. 2016.

13. Trezise S, Karnowski A, Fedele P L, Mithraprabhu S, Liao Y, D'Costa K, et al. Mining the Plasma Cell Transcriptome for Novel Cell Surface Proteins. Int J Mol Sci. 2018; 19(8).

14. Gundry R L, Riordon D R, Tarasova Y, Chuppa S, Bhattacharya S, Juhasz O, et al. A cell surfaceome map for immunophenotyping and sorting pluripotent stem cells. Mol Cell Proteomics. 2012; 11(8):303-16.

15. Jia J, Bosley A D, Thompson A, Hoskins J W, Cheuk A, Collins I, et al. CLPTM1L promotes growth and enhances aneuploidy in pancreatic cancer cells. Cancer Res. 2014.

16. Ni Z, Tao K, Chen G, Chen Q, Tang J, Luo X, et al. CLPTM1L is overexpressed in lung cancer and associated with apoptosis. PLOS One. 2012; 7(12):e52598.

17. Yamamoto K, Okamoto A, Isonishi S, Ochiai K, Ohtake Y. A novel gene, CRR9, which was up-regulated in CDDP-resistant ovarian tumor cell line, was associated with apoptosis. Biochem Biophys Res Commun. 2001; 280(4):1148-54.

18. Gyorffy B, Lanczky A, Szallasi Z. Implementing an online tool for genome-wide validation of survival-associated biomarkers in ovarian-cancer using microarray data from 1287 patients. Endocr Relat Cancer. 2012; 19(2):197-208.

19. Izzo G, Freitas E L, Krepischi A C, Pearson P L, Vasques L R, Passos-Bueno M R, et al. A microduplication of 5p15.33 reveals CLPTM1L as a candidate gene for cleft lip and palate. Eur J Med Genet. 2013; 56(4):222-5.

20. Yoshiura K, Machida J, Daack-Hirsch S, Patil S R, Ashworth L K, Hecht J T, et al. Characterization of a novel gene disrupted by a balanced chromosomal translocation t(2; 19)(q11.2; q13.3) in a family with cleft lip and palate. Genomics. 1998; 54(2):231-40.

21. da Cunha J P, Galante P A, de Souza J E, de Souza R F, Carvalho P M, Ohara D T, et al. Bioinformatics construction of the human cell surfaceome. Proc Natl Acad Sci U S A. 2009; 106(39):16752-7.

22. Colombo J, Fachel A A, De Freitas Calmon M, Cury P M, Fukuyama E E, Tajara E H, et al. Gene expression profiling reveals molecular marker candidates of laryngeal squamous cell carcinoma. Oncol Rep. 2009; 21(3): 649-63.

23. Mobuchon L, Battistella A, Bardel C, Scelo G, Renoud A, Houy A, et al. A GWAS in uveal melanoma identifies risk polymorphisms in the CLPTM1L locus. NPJ Genom Med. 2017; 2.

24. Lee H W, Park W J, Heo Y R, Park T I, Park S Y, Lee J H. TERT-CLPTM1 locus polymorphism (rs401681) is associated with the prognosis of hepatocellular carcinoma. Onco Targets Ther. 2017; 10:4853-8.

25. Zhang R, Chen X, Zhang S, Zhang X, Li T, Liu Z, et al. Upregulation of miR-494 Inhibits Cell Growth and Invasion and Induces Cell Apoptosis by Targeting Cleft Lip and Palate Transmembrane 1-Like in Esophageal Squamous Cell Carcinoma. Dig Dis Sci. 2015; 60(5): 1247-55.

26. Crow J, Atay S, Banskota S, Artale B, Schmitt S, Godwin A K. Exosomes as mediators of platinum resistance in ovarian cancer. Oncotarget. 2017; 8(7): 11917-36.

27. Zhang H D, Jiang L H, Hou J C, Zhong S L, Zhu L P, Wang D D, et al. Exosome: a novel mediator in drug resistance of cancer cells. Epigenomics. 2018.

28. Li X, Wang X. The emerging roles and therapeutic potential of exosomes in epithelial ovarian cancer. Mol Cancer. 2017; 16(1):92.

29. "Guidance for Industry: For the Submission of Chemistry, Manufacturing and Controls and Establishment Description Information for Human Blood and Blood Components Intended for Transfusion or for Further Manufacture and for the Completion of the Form FDA 356h, 'Application to Market a New Drug, Biologic or an Antibiotic Drug for Human Use;'" availability. Food and Drug Administration, HHS. Notice. Fed Regist. 1999; 64(89):25049-50.

SEQUENCE LISTING

Sequence total quantity: 71
SEQ ID NO: 1          moltype = DNA   length = 1617
FEATURE               Location/Qualifiers
source                1..1617
                      mol_type = genomic DNA -continued

```
                            organism = Homo sapiens
SEQUENCE: 1
atgtggagcg gccgcagctc cttcaccagc ttggtggtgg gcgtgttcgt ggtctacgtg  60
gtgcacacct gctgggtcat gtacggcatc gtctacaccc gcccgtgctc cggcgacgcc  120
aactgcatcc agccctacct ggcgcggcgg cccaagctgc agctgagcgt gtacaccacg  180
acgaggtccc acctgggtgc tgagaacaac atcgacctgg tcttgaatgt ggaagacttt  240
gatgtggagt ccaaatttga aaggacagtt aatgtttctg taccaaagaa aacgagaaac  300
aatgggacgt gtatgcctaa catcttcctc catcacgctg gggtcctgcc gtggcacgac  360
gggaagcagg tgcacctggt cagtcctctg accacctaca tggtccccaa gccagaagat  420
atcaacctgc tcaccgggga gtctgataca cagcagatcg aggcggagaa gaagccgacg  480
agtgccctgg atgagccagt gtcccactgg cgaccgcggc tggcgctgaa cgtgatggcg  540
gacaactttg tctttgacgg gtcctccctg cctgccgatg tgcatcggta catgaagatg  600
atccagctgg gaaaaccgt gcattacctg cccatcctgt tcatcgacca gctcagcaac  660
cgcgtgaagg acctgatggt cataaaccgc tccaccaccg agctgcccct caccgtgtcc  720
tacgacaagg tctcactggg gcggctcgc ttctggatcc acatgcagga cgccgtgtac  780
tccctgcagc agttcgggtt ttcagagaaa gatgctgatg aggtgaaagg aattttgta  840
gataccaact tatacttcct ggcgctgacc ttctttgtcg cagcgttcca tcttctcttt  900
gatttcctgg cctttaaaaa tgacatcagt ttctggaaga agaagaagag catgatcggc  960
atgtccacca aggcagtgct ctggcgctgc ttcagcaccg tggtcatctt tctgttcctg  1020
ctggacgagc agacgagcct gctggtgctg gtcccggcgg gtgttggagc cgccattgag  1080
ctgtggaaag tgaagaaggc attgaagatg actatttttt ggagaggcct gatgcccgaa  1140
tttcagtttg gcacttacag cgaatctgag aggaaaaccg aggtacgaca tactcaggcc  1200
atgaagtact tgtcatacct gctgtaccct ctctgtgtcg ggggtgctgt ctattcactc  1260
ctgaatatca aatataagag ctggtactcc tggttaatca acagcttcgt caacggggtc  1320
tatgcctttg gtttcctctt catgctgccc cagctctttg tgaactacaa gttgaagtca  1380
gtggcacatc tgcccctggaa ggccttcacc tacaaggctt tcaacacctt cattgatgac  1440
gtctttgcct tcatcatcac catgcccacg tctcaccggc tggcctgctt ccgggacgac  1500
gtggtgtttc tggtctacct gtaccagcgg tggctttatc ctgtcggataa acgcagagtg  1560
aacgagtttg gggagtccta cgaggagaag gccacgcggg cgccccacac ggactga  1617

SEQ ID NO: 2                moltype = AA  length = 538
FEATURE                     Location/Qualifiers
source                      1..538
                            mol_type = protein
                            organism = Homo sapiens
SEQUENCE: 2
MWSGRSSFTS LVVGVFVVYV VHTCWVMYGI VYTRPCSGDA NCIQPYLARR PKLQLSVYTT  60
TRSHLGAENN IDLVLNVEDF DVESKFERTV NVSVPKKTRN NGTLYAYIFL HHAGVLPWHD  120
GKQVHLVSPL TTYMVPKPEE INLLTGESDT QQIEAEKKPT SALDEPVSHW RPRLALNVMA  180
DNFVFDGSSL PADVHRYMKM IQLGKTVHYL PILFIDQLSN RVKDLMVINR STTELPLTVS  240
YDKVSLGRLR FWIHMQDAVY SLQQFGFSEK DADEVKGIFV DTNLYFLALT FFVAAFHLLF  300
DFLAFKNDIS FWKKKKSMIG MSTKAVLWRC FSTVVIFLFL LDEQTSLLVL VPAGVGAAIE  360
LWKVKKALKM TIFWRGLMPE FQFGTYSESE RKTEEYDTQA MKYLSYLLYP LCVGGAVYSL  420
LNIKYKSWYS WLINSFVNGV YAFGFLFMLP QLFVNYKLKS VAHLPWKAFT YKAFNTFIDD  480
VFAFIITMPT SHRLACFRDD VVFLVYLYQR WLYPVDKRRV NEFGESYEEK ATRAPHTD  538

SEQ ID NO: 3                moltype = DNA  length = 1759
FEATURE                     Location/Qualifiers
source                      1..1759
                            mol_type = genomic DNA
                            organism = Homo sapiens
SEQUENCE: 3
ctctgaccac ctacatggtc cccaagccag aagaaatcaa cctgctcacc ggggagtctg  60
atacacagca gatcgaggcg gagaagaagc gacgagtgc cctggatgag ccagtgtccc  120
actggcgacc gcggctggcg ctgaacgtga tggcggacaa ctttgtcttt gacgggtcct  180
ccctgcctgc cgatgtgcat cggtacatga agatgatcca gctggggaaa accgtgcatt  240
acctgcccat cctgttcatc gaccagctca gcaaccgcgt gaaggacctg atggtcataa  300
accgctccac caccgagctg cccctcaccg tgtcctacga caaggtctca ctggggcggc  360
tgcgcttctg gatccacatg caggacgccg tgtactccct gcagcagttc gggttttcag  420
agaaagatgc tgatgaggtg aaaggaattt tgtagatac caacttatac ttcctggcgc  480
tgaccttctt tgtcgcagcg ttccatcttc tctttgattt cctggccttt aaaaatgaca  540
tcagtttctg gaagaagaag aagagcatga tcggcatgtc caccaagctg tggaaagtga  600
agaaggcatt gaagatgact attttttgga gaggcctgat gcccgaattt cagtttggca  660
cttacagcga atctgagagg aaaaccgagg tacgacatac tcaggccatg aagtacttgt  720
catacctgct gtaccctctc tgtgtcgggg gtgctgtcta ttcactcctg aatatcaaat  780
ataagagctg gtactcctgg ttaatcaaca gcttcgtcaa cggggtctat gcctttggtt  840
tcctcttcat gctgccccag ctctttgtga actacaagtt gaagtcagtg gcacatctgc  900
cctggaaggc cttcacctac aaggctttca cacctttcat tgatgacgtc tttgccttca  960
tcatcaccat gcccacgtct caccggctgg cctgcttccg ggacgacgtg gtgtttctgg  1020
tctacctgta ccagcggtgg ctttatcctg tggataaacg cagagtgaac gagtttgggg  1080
agtcctacga ggagaaggcc acgcgggcgc ccacacgga ctgaaggccg cccgggctgc  1140
cgccagccaa gtgcaacttg aattgtcaat gagtattttt ggaagcattt ggaggaattc  1200
ctagacattg cgtttctgt gttgccaaaa tcccttcgga catttctcag acatctccca  1260
agttcccatc acgtcagatt tggagctggt agcgcttcac atgccccac gtgtgaacat  1320
ctgtcttggt cacagagctg ggtgctgccg gtcaccttga gctgtggtgg ctcccggcac  1380
acgagtgtcc ggggttcggc catgtcctca cgcgggcagg ggtgggagcc ctcacaggca  1440
agggggctgt ggatttccat tttcaggtgg ttttctaagt gctccttatg tgaatttcaa  1500
acacgtatgg aattcattcc gcatggactc tgggatcaaa ggctctttcc tcttttgttt  1560
gagagttggt tgtttaaaag cttaatgtat gtttctattt taaaataaat ttttctggct  1620
```

-continued

```
gtggcatttt tcttgacctg gtataatgaa agtatttcag atatttgagt ttaacccttt    1680
tccagaaagt aatacatgat atggatttat ttatgcatta aaagagcaaa tttaaagagc    1740
aaaaaaaaaa aaaaaaaaa                                                  1759

SEQ ID NO: 4               moltype = AA   length = 12
FEATURE                    Location/Qualifiers
source                     1..12
                           mol_type = protein
                           organism = Homo sapiens
SEQUENCE: 4
RRPKLQLSVY TT                                                          12

SEQ ID NO: 5               moltype = AA   length = 12
FEATURE                    Location/Qualifiers
source                     1..12
                           mol_type = protein
                           organism = Homo sapiens
SEQUENCE: 5
ENNIDLVLNV ED                                                          12

SEQ ID NO: 6               moltype = AA   length = 12
FEATURE                    Location/Qualifiers
source                     1..12
                           mol_type = protein
                           organism = Homo sapiens
SEQUENCE: 6
EDFDVESKFE RT                                                          12

SEQ ID NO: 7               moltype = AA   length = 12
FEATURE                    Location/Qualifiers
source                     1..12
                           mol_type = protein
                           organism = Homo sapiens
SEQUENCE: 7
HAGVLPWHDG KQ                                                          12

SEQ ID NO: 8               moltype = AA   length = 12
FEATURE                    Location/Qualifiers
source                     1..12
                           mol_type = protein
                           organism = Homo sapiens
SEQUENCE: 8
DGSSLPADVH RY                                                          12

SEQ ID NO: 9               moltype = AA   length = 12
FEATURE                    Location/Qualifiers
source                     1..12
                           mol_type = protein
                           organism = Homo sapiens
SEQUENCE: 9
HRYMKMIQLG KT                                                          12

SEQ ID NO: 10              moltype = AA   length = 12
FEATURE                    Location/Qualifiers
source                     1..12
                           mol_type = protein
                           organism = Homo sapiens
SEQUENCE: 10
TELPLTVSYD KV                                                          12

SEQ ID NO: 11              moltype = AA   length = 12
FEATURE                    Location/Qualifiers
source                     1..12
                           mol_type = protein
                           organism = Homo sapiens
SEQUENCE: 11
QQFGFSEKDA DE                                                          12

SEQ ID NO: 12              moltype = AA   length = 10
FEATURE                    Location/Qualifiers
source                     1..10
                           mol_type = protein
                           organism = Homo sapiens
SEQUENCE: 12
TRPCSGDANC                                                             10

SEQ ID NO: 13              moltype = AA   length = 12
FEATURE                    Location/Qualifiers
source                     1..12
```

-continued

```
                                 mol_type = protein
                                 organism = Homo sapiens
SEQUENCE: 13
RRPKLQLSVY TT                                                    12

SEQ ID NO: 14           moltype = AA  length = 11
FEATURE                 Location/Qualifiers
source                  1..11
                        mol_type = protein
                        organism = Homo sapiens
SEQUENCE: 14
ENNIDLVLNV E                                                     11

SEQ ID NO: 15           moltype = AA  length = 10
FEATURE                 Location/Qualifiers
source                  1..10
                        mol_type = protein
                        organism = Homo sapiens
SEQUENCE: 15
FDVESKFERT                                                       10

SEQ ID NO: 16           moltype = AA  length = 12
FEATURE                 Location/Qualifiers
source                  1..12
                        mol_type = protein
                        organism = Homo sapiens
SEQUENCE: 16
HAGVLPWHDG KQ                                                    12

SEQ ID NO: 17           moltype = AA  length = 10
FEATURE                 Location/Qualifiers
source                  1..10
                        mol_type = protein
                        organism = Homo sapiens
SEQUENCE: 17
TTYMVPKPEE                                                       10

SEQ ID NO: 18           moltype = AA  length = 10
FEATURE                 Location/Qualifiers
source                  1..10
                        mol_type = protein
                        organism = Homo sapiens
SEQUENCE: 18
INLLTGESDT                                                       10

SEQ ID NO: 19           moltype = AA  length = 10
FEATURE                 Location/Qualifiers
source                  1..10
                        mol_type = protein
                        organism = Homo sapiens
SEQUENCE: 19
ESDTQQIEAE                                                       10

SEQ ID NO: 20           moltype = AA  length = 11
FEATURE                 Location/Qualifiers
source                  1..11
                        mol_type = protein
                        organism = Homo sapiens
SEQUENCE: 20
KKPTSALDEP V                                                     11

SEQ ID NO: 21           moltype = AA  length = 10
FEATURE                 Location/Qualifiers
source                  1..10
                        mol_type = protein
                        organism = Homo sapiens
SEQUENCE: 21
DGSSLPADVH                                                       10

SEQ ID NO: 22           moltype = AA  length = 12
FEATURE                 Location/Qualifiers
source                  1..12
                        mol_type = protein
                        organism = Homo sapiens
SEQUENCE: 22
HRYMKMIQLG KT                                                    12

SEQ ID NO: 23           moltype = AA  length = 10
FEATURE                 Location/Qualifiers
```

-continued

```
source                  1..10
                        mol_type = protein
                        organism = Homo sapiens
SEQUENCE: 23
LPLTVSYDKV                                                              10

SEQ ID NO: 24           moltype = AA   length = 11
FEATURE                 Location/Qualifiers
source                  1..11
                        mol_type = protein
                        organism = Homo sapiens
SEQUENCE: 24
MQDAVYSLQQ F                                                            11

SEQ ID NO: 25           moltype = AA   length = 9
FEATURE                 Location/Qualifiers
source                  1..9
                        mol_type = protein
                        organism = Homo sapiens
SEQUENCE: 25
GFSEKDADE                                                               9

SEQ ID NO: 26           moltype = AA   length = 121
FEATURE                 Location/Qualifiers
REGION                  1..121
                        note = Synthetic- Anti-CRR9/CLPTM1L clone 102-1 heavy chain
                        V
source                  1..121
                        mol_type = protein
                        organism = synthetic construct
SEQUENCE: 26
EVQLLESGAE VKKPGSSVKV SCKASGGTFS SYAISWVRQA PGQGLEWMGI INPSGGSTSY  60
AQKFQGRVTM TRDTSTSTVY MELSSLRSED TAVYYCARGG LSRLEILLDN WGQGTLVTVS  120
S                                                                       121

SEQ ID NO: 27           moltype = AA   length = 111
FEATURE                 Location/Qualifiers
REGION                  1..111
                        note = Synthetic- Anti-CRR9/CLPTM1L clone 102-1 light chain
                        V
source                  1..111
                        mol_type = protein
                        organism = synthetic construct
SEQUENCE: 27
VHVILTQPPS LSAAPGQRVT ISCSGSDSNI GNNYVSWYRQ FPGTAPKLLI YDNNKRPSGV  60
PDRFSGSKSG TSAILDITGL QAGDEADYYC GSWDTSLDAW VFGGGTKLTV L             111

SEQ ID NO: 28           moltype = AA   length = 115
FEATURE                 Location/Qualifiers
REGION                  1..115
                        note = Synthetic- Anti-CRR9/CLPTM1L clone 102-4 heavy chain
                        V
source                  1..115
                        mol_type = protein
                        organism = synthetic construct
SEQUENCE: 28
EVQLLESGGG VVQPGGSLSL SCAASGFTFK NYGMHWVRQA PGKGLEWVSG ISWNSGSIGY  60
ADSVKGRFTI SRDNAKNSLY LQMNSLRAED TAVYYCARSR YSDYWGQGTL VTVSS         115

SEQ ID NO: 29           moltype = AA   length = 107
FEATURE                 Location/Qualifiers
REGION                  1..107
                        note = Synthetic- Anti-CRR9/CLPTM1L clone 102-4 light chain
                        V
source                  1..107
                        mol_type = protein
                        organism = synthetic construct
SEQUENCE: 29
DIQMTQSPSS LSASVGDRVT IACRASQGIR NDLGWYQQKP GKAPKLLIYA ASSLQSGVPS  60
RFSGSGSGTD FTLTIIILQP EDYATYYCLQ DYNYPWTFGQ RTKLDIK                  107

SEQ ID NO: 30           moltype = AA   length = 122
FEATURE                 Location/Qualifiers
REGION                  1..122
                        note = Synthetic- Anti-CRR9/CLPTM1L clone 102-5 heavy chain
                        V
source                  1..122
                        mol_type = protein
                        organism = synthetic construct
```

```
SEQUENCE: 30
EVQLLESGGG LVQPGGSLRL SCAASGFSFS SYEMNWVRQA PGKGPEWISY ISSGGGTIYY  60
ADSVRGRFTI SRDNSNNTLY LQMNSLRPDD TAIYYCARDR GRKWLQLLFD SWGQGTLVTV  120
SS                                                                 122

SEQ ID NO: 31            moltype = AA  length = 111
FEATURE                  Location/Qualifiers
REGION                   1..111
                         note = Synthetic- Anti-CRR9/CLPTM1L clone 102-5 light chain
                          V
source                   1..111
                         mol_type = protein
                         organism = synthetic construct
SEQUENCE: 31
QAVLTQPPSA SGTPGQKVTI SCSGSSSNIG SNTVNWYQQL PGTAPKLLIY TNNQRPSGVP  60
DRFSGSKSGA SASLAISGLQ SKDEADYYCA AWDDSLNGWV FGGGTKLTVL G          111

SEQ ID NO: 32            moltype = AA  length = 114
FEATURE                  Location/Qualifiers
REGION                   1..114
                         note = Synthetic- Anti-CRR9/CLPTM1L clone 102-22 heavy
                          chain V
source                   1..114
                         mol_type = protein
                         organism = synthetic construct
SEQUENCE: 32
EVQLVESGGG VVRPGGSLRL SCAASGFTFD DYGMSWVRQA PGKGLEWVSG INWNGGSTGY  60
ADSVKGRFTI SRDNAKNSLY LQMNSLRAED TAVYYCASLT GGYHGMDVWG QGTL        114

SEQ ID NO: 33            moltype = AA  length = 111
FEATURE                  Location/Qualifiers
REGION                   1..111
                         note = Synthetic- Anti-CRR9/CLPTM1L clone 102-22 light
                          chain V
source                   1..111
                         mol_type = protein
                         organism = synthetic construct
SEQUENCE: 33
QSVLTQPPSA SGTPGQRVTI SCSGSSSNIG SNYVYWYQQL PGTAPKLLIY RNNQRPSGVP  60
DRFSGSKSGT SASLAISGLR SEDEADYYCA AWDDSLSGPW VFGGGTKVTV L           111

SEQ ID NO: 34            moltype = AA  length = 122
FEATURE                  Location/Qualifiers
REGION                   1..122
                         note = Synthetic- Anti-CRR9/CLPTM1L clone 102-27 heavy
                          chain V
source                   1..122
                         mol_type = protein
                         organism = synthetic construct
SEQUENCE: 34
EVQLVESGAE VKKPGSSVKV SCKASGGTFS IYATNWVRQA PGQGPEWMGG IIPMIDTTNY  60
AQKFRGRLTV TADKSTRTAY MELINLTSDD TAVYYCAGDP RRYGDYEYFE FWGQGTLVTV  120
SS                                                                 122

SEQ ID NO: 35            moltype = AA  length = 109
FEATURE                  Location/Qualifiers
REGION                   1..109
                         note = Synthetic- Anti-CRR9/CLPTM1L clone 102-27 light
                          chain V
source                   1..109
                         mol_type = protein
                         organism = synthetic construct
SEQUENCE: 35
QTVVTQEPSL TVSPGGTVTL TCASSTGAVT SGYFPNWFQQ KPGQAPRALI YSTSNRHPWT  60
PARFSGSLLG GKAALTLSGV QPEDEADYYC LIYSGGVYVF GTGTKLTVL              109

SEQ ID NO: 36            moltype = AA  length = 7
FEATURE                  Location/Qualifiers
REGION                   1..7
                         note = Synthetic- Anti-CRR9/CLPTM1L clone 102-1 VH CDR1
source                   1..7
                         mol_type = protein
                         organism = synthetic construct
SEQUENCE: 36
GGTFSSY                                                              7

SEQ ID NO: 37            moltype = AA  length = 6
FEATURE                  Location/Qualifiers
REGION                   1..6
```

-continued

```
                                    note = Synthetic- Anti-CRR9/CLPTM1L clone 102-1 VH CDR2
source                              1..6
                                    mol_type = protein
                                    organism = synthetic construct
SEQUENCE: 37
NPSGGS                                                                                 6

SEQ ID NO: 38                       moltype = AA   length = 11
FEATURE                             Location/Qualifiers
REGION                              1..11
                                    note = Synthetic- Anti-CRR9/CLPTM1L clone 102-1 VH CDR3
source                              1..11
                                    mol_type = protein
                                    organism = synthetic construct
SEQUENCE: 38
GGLSRLEILL D                                                                          11

SEQ ID NO: 39                       moltype = AA   length = 13
FEATURE                             Location/Qualifiers
REGION                              1..13
                                    note = Synthetic- Anti-CRR9/CLPTM1L clone 102-1 VL CDR1
source                              1..13
                                    mol_type = protein
                                    organism = synthetic construct
SEQUENCE: 39
SGSDSNIGNN YVS                                                                        13

SEQ ID NO: 40                       moltype = AA   length = 7
FEATURE                             Location/Qualifiers
REGION                              1..7
                                    note = Synthetic- Anti-CRR9/CLPTM1L clone 102-1 VL CDR2
source                              1..7
                                    mol_type = protein
                                    organism = synthetic construct
SEQUENCE: 40
DNNKRPS                                                                                7

SEQ ID NO: 41                       moltype = AA   length = 11
FEATURE                             Location/Qualifiers
REGION                              1..11
                                    note = Synthetic- Anti-CRR9/CLPTM1L clone 102-1 VL CDR3
source                              1..11
                                    mol_type = protein
                                    organism = synthetic construct
SEQUENCE: 41
GSWDTSLDAW V                                                                          11

SEQ ID NO: 42                       moltype = AA   length = 7
FEATURE                             Location/Qualifiers
REGION                              1..7
                                    note = Synthetic- Anti-CRR9/CLPTM1L clone 102-4 VH CDR1
source                              1..7
                                    mol_type = protein
                                    organism = synthetic construct
SEQUENCE: 42
GFTFKNY                                                                                7

SEQ ID NO: 43                       moltype = AA   length = 6
FEATURE                             Location/Qualifiers
REGION                              1..6
                                    note = Synthetic- Anti-CRR9/CLPTM1L clone 102-4 VH CDR2
source                              1..6
                                    mol_type = protein
                                    organism = synthetic construct
SEQUENCE: 43
SWNSGS                                                                                 6

SEQ ID NO: 44                       moltype = AA   length = 6
FEATURE                             Location/Qualifiers
REGION                              1..6
                                    note = Synthetic- Anti-CRR9/CLPTM1L clone 102-4 VH CDR3
source                              1..6
                                    mol_type = protein
                                    organism = synthetic construct
SEQUENCE: 44
SRYSDY                                                                                 6

SEQ ID NO: 45                       moltype = AA   length = 11
FEATURE                             Location/Qualifiers
```

-continued

```
REGION                    1..11
                          note = Synthetic- Anti-CRR9/CLPTM1L clone 102-4 VL CDR1
source                    1..11
                          mol_type = protein
                          organism = synthetic construct
SEQUENCE: 45
RASQGIRNDL G                                                              11

SEQ ID NO: 46             moltype = AA   length = 7
FEATURE                   Location/Qualifiers
REGION                    1..7
                          note = Synthetic- Anti-CRR9/CLPTM1L clone 102-4 VL CDR2
source                    1..7
                          mol_type = protein
                          organism = synthetic construct
SEQUENCE: 46
AASSLQS                                                                   7

SEQ ID NO: 47             moltype = AA   length = 9
FEATURE                   Location/Qualifiers
REGION                    1..9
                          note = Synthetic- Anti-CRR9/CLPTM1L clone 102-4 VL CDR3
source                    1..9
                          mol_type = protein
                          organism = synthetic construct
SEQUENCE: 47
LQDYNYPWT                                                                 9

SEQ ID NO: 48             moltype = AA   length = 7
FEATURE                   Location/Qualifiers
REGION                    1..7
                          note = Synthetic- Anti-CRR9/CLPTM1L clone 102-5 VH CDR1
source                    1..7
                          mol_type = protein
                          organism = synthetic construct
SEQUENCE: 48
GFSFSSY                                                                   7

SEQ ID NO: 49             moltype = AA   length = 6
FEATURE                   Location/Qualifiers
REGION                    1..6
                          note = Synthetic- Anti-CRR9/CLPTM1L clone 102-5 VH CDR2
source                    1..6
                          mol_type = protein
                          organism = synthetic construct
SEQUENCE: 49
SSGGGT                                                                    6

SEQ ID NO: 50             moltype = AA   length = 13
FEATURE                   Location/Qualifiers
REGION                    1..13
                          note = Synthetic- Anti-CRR9/CLPTM1L clone 102-5 VH CDR3
source                    1..13
                          mol_type = protein
                          organism = synthetic construct
SEQUENCE: 50
DRGRKWLQLL FDS                                                            13

SEQ ID NO: 51             moltype = AA   length = 13
FEATURE                   Location/Qualifiers
REGION                    1..13
                          note = Synthetic- Anti-CRR9/CLPTM1L clone 102-5 VL CDR1
source                    1..13
                          mol_type = protein
                          organism = synthetic construct
SEQUENCE: 51
SGSSSNIGSN TVN                                                            13

SEQ ID NO: 52             moltype = AA   length = 7
FEATURE                   Location/Qualifiers
REGION                    1..7
                          note = Synthetic- Anti-CRR9/CLPTM1L clone 102-5 VL CDR2
source                    1..7
                          mol_type = protein
                          organism = synthetic construct
SEQUENCE: 52
TNNQRPS                                                                   7

SEQ ID NO: 53             moltype = AA   length = 11
```

-continued

| FEATURE | Location/Qualifiers |
|---|---|
| REGION | 1..11 |
| | note = Synthetic- Anti-CRR9/CLPTM1L clone 102-5 VL CDR3 |
| source | 1..11 |
| | mol_type = protein |
| | organism = synthetic construct |

SEQUENCE: 53
AAWDDSLNGW V                                                                    11

| SEQ ID NO: 54 | moltype = AA   length = 7 |
|---|---|
| FEATURE | Location/Qualifiers |
| REGION | 1..7 |
| | note = Synthetic- Anti-CRR9/CLPTM1L clone 102-22 VH CDR1 |
| source | 1..7 |
| | mol_type = protein |
| | organism = synthetic construct |

SEQUENCE: 54
GFTFDDY                                                                         7

| SEQ ID NO: 55 | moltype = AA   length = 6 |
|---|---|
| FEATURE | Location/Qualifiers |
| REGION | 1..6 |
| | note = Synthetic- Anti-CRR9/CLPTM1L clone 102-22 VH CDR2 |
| source | 1..6 |
| | mol_type = protein |
| | organism = synthetic construct |

SEQUENCE: 55
NWNGGS                                                                          6

| SEQ ID NO: 56 | moltype = AA   length = 10 |
|---|---|
| FEATURE | Location/Qualifiers |
| REGION | 1..10 |
| | note = Synthetic- Anti-CRR9/CLPTM1L clone 102-22 VH CDR3 |
| source | 1..10 |
| | mol_type = protein |
| | organism = synthetic construct |

SEQUENCE: 56
LTGGYHGMDV                                                                      10

| SEQ ID NO: 57 | moltype = AA   length = 13 |
|---|---|
| FEATURE | Location/Qualifiers |
| REGION | 1..13 |
| | note = Synthetic- Anti-CRR9/CLPTM1L clone 102-22 VL CDR1 |
| source | 1..13 |
| | mol_type = protein |
| | organism = synthetic construct |

SEQUENCE: 57
SGSSSNIGSN YVY                                                                  13

| SEQ ID NO: 58 | moltype = AA   length = 7 |
|---|---|
| FEATURE | Location/Qualifiers |
| REGION | 1..7 |
| | note = Synthetic- Anti-CRR9/CLPTM1L clone 102-22 VL CDR2 |
| source | 1..7 |
| | mol_type = protein |
| | organism = synthetic construct |

SEQUENCE: 58
RNNQRPS                                                                         7

| SEQ ID NO: 59 | moltype = AA   length = 12 |
|---|---|
| FEATURE | Location/Qualifiers |
| REGION | 1..12 |
| | note = Synthetic- Anti-CRR9/CLPTM1L clone 102-22 VL CDR3 |
| source | 1..12 |
| | mol_type = protein |
| | organism = synthetic construct |

SEQUENCE: 59
AAWDDSLSGP WV                                                                   12

| SEQ ID NO: 60 | moltype = AA   length = 7 |
|---|---|
| FEATURE | Location/Qualifiers |
| REGION | 1..7 |
| | note = Synthetic- Anti-CRR9/CLPTM1L clone 102-27 VH CDR1 |
| source | 1..7 |
| | mol_type = protein |
| | organism = synthetic construct |

SEQUENCE: 60
GGTFSIY                                                                         7

```
SEQ ID NO: 61            moltype = AA  length = 6
FEATURE                  Location/Qualifiers
REGION                   1..6
                         note = Synthetic- Anti-CRR9/CLPTM1L clone 102-27 VH CDR2
source                   1..6
                         mol_type = protein
                         organism = synthetic construct
SEQUENCE: 61
IPMIDT                                                                    6

SEQ ID NO: 62            moltype = AA  length = 13
FEATURE                  Location/Qualifiers
REGION                   1..13
                         note = Synthetic- Anti-CRR9/CLPTM1L clone 102-27 VH CDR3
source                   1..13
                         mol_type = protein
                         organism = synthetic construct
SEQUENCE: 62
DPRRYGDYEY FEF                                                           13

SEQ ID NO: 63            moltype = AA  length = 14
FEATURE                  Location/Qualifiers
REGION                   1..14
                         note = Synthetic- Anti-CRR9/CLPTM1L clone 102-27 VL CDR1
source                   1..14
                         mol_type = protein
                         organism = synthetic construct
SEQUENCE: 63
ASSTGAVTSG YFPN                                                          14

SEQ ID NO: 64            moltype = AA  length = 7
FEATURE                  Location/Qualifiers
REGION                   1..7
                         note = Synthetic- Anti-CRR9/CLPTM1L clone 102-27 VL CDR2
source                   1..7
                         mol_type = protein
                         organism = synthetic construct
SEQUENCE: 64
STSNRHP                                                                   7

SEQ ID NO: 65            moltype = AA  length = 9
FEATURE                  Location/Qualifiers
REGION                   1..9
                         note = Synthetic- Anti-CRR9/CLPTM1L clone 102-27 VL CDR3
source                   1..9
                         mol_type = protein
                         organism = synthetic construct
SEQUENCE: 65
LIYSGGVYV                                                                 9

SEQ ID NO: 66            moltype = DNA  length = 750
FEATURE                  Location/Qualifiers
misc_feature             1..750
                         note = Synthetic- anti-CRR9 clone 102-21 codon-optimized
                         DNA sequence
source                   1..750
                         mol_type = other DNA
                         organism = synthetic construct
SEQUENCE: 66
cacgtgatcc tgacacagcc tcctagcctg tctgctgccc ctggacagag agtgaccatc   60
agctgtagcg gcagcgacag caacatcggc aacaactacg tgtcctggta cagacagttc  120
cccggcacag cccctaagct gctgatctac gacaacaaca agcggcctag cggcgtgccc  180
gatagatttt ctggcagcaa gagcggcacc agcgccatcc tggatattac aggactgcag  240
gccggcgacg aggccgatta ctattgtggc agctgggaca ccagcctgga cgcttgggtt  300
ttcggcggag gcacaaagct gacagtgctt ggaggcggag gatctggcgg cggaggaagc  360
ggaggcggtt ctggcggtgg tggatctgaa gttcagctgc tggaatctgg cgccgaagtg  420
aagaaacctg gcagcagcgt gaaggtgtcc tgcaaagctt ctggcggcac cttcagcagc  480
tacgccatct cttgggttcg acaggcccca ggacaaggcc tggaatggat gggcatcatc  540
aatccaagcg gcggcagcac aagctacgcc cagaaatcc agggcagagt gacaatgacc  600
agagacacca gcacctccac cgtgtacatg aactgagca gcctgagaag cgaggacacc  660
gccgtgtact actgtgctag aggcggcctg agcggctgg aaatcctgct ggataattgg  720
ggccagggca ccctggtcac agtgtcatct                                    750

SEQ ID NO: 67            moltype = DNA  length = 723
FEATURE                  Location/Qualifiers
misc_feature             1..723
                         note = Synthetic- anti-CRR9 clone 102-4 codon-optimized DNA
                         sequence
source                   1..723
```

```
                       mol_type = other DNA
                       organism = synthetic construct
SEQUENCE: 67
gaagtgcagc tgctggaatc tggtggcgga gttgttcagc ctggcggctc tctgtctctg   60
tcttgtgccg ccagcggctt caccttcaag aactacggca tgcactgggt ccgacaggcc  120
cctggaaaag gccttgaatg ggtgtccggc atcagctgga atagcggctc tatcggctac  180
gccgacagcg tgaagggcag attcaccatc agccgggaca cgccaagaa cagcctgtac  240
ctgcagatga actccctgag agccgaggac accgccgtgt actactgtgc cagaagccgg  300
tacagcgact attggggcca gggcacactg gtcacagttt ctagcggagg cggaggaagt  360
ggcggcggag gatctggcgg tggtagtggc ggtggcggt ctgacattca gatgacacag  420
agccccagca gcctgtctgc ctctgtggga gacagagtga caatcgcctg cagagccagc  480
cagggcatca gaaatgacct cggctggtat cagcagaagc ccggcaaagc ccctaagctg  540
ctgatctatg ccgcctcctc tctgcaatct ggcgtgccct ctagatttc cggctctggc  600
agcggcaccg acttcaccct gaccatcatc atcctgcagc ctgaggacta cgccacctac  660
tactgcctgc aagactacaa ctaccctgg accttcggcc agaggaccaa gctggatatc  720
aag                                                                723

SEQ ID NO: 68          moltype = DNA  length = 741
FEATURE                Location/Qualifiers
misc_feature          1..741
                       note = Synthetic- anti-CRR9 clone 102-5 codon-optimized DNA
                       sequence
source                1..741
                       mol_type = other DNA
                       organism = synthetic construct
SEQUENCE: 68
caggctgtgc tgactcagcc gccctcagcg tctgggaccc ccgggcagaa ggtcaccatc   60
tcttgttctg gaagcagctc caacatcgga agtaatactg taaactggta ccaacagctc  120
ccaggaacgg cccccaaact cctcatctat actaataatc agcggccctc aggggtccct  180
gaccgattct ctggctccaa gtctggcgcc tcagcctcc tgggccatcag tgggctccag  240
tctaaggatg aggctgatta ttactgtgca gcatgggatg acagcctgaa tggttgggtg  300
ttcggcggag ggaccaagct caccgtccta ggtgagggta atcttccgg atctggttcc  360
gaatccaaag ctagcgaggt gcagctgttg gagtctgggg gaggcttggt tcagccggga  420
gggtccctga gactctcctg tgcagcctct ggattcagtt tcagtagtta tgaaatgaac  480
tgggtccgcc aggctccagg caaggggccg gagtggattt catacatcag cagtggtggt  540
ggtaccatat actacgcaga ctccgtgagg ggccgattca ccatctccag agacaactcc  600
aacaacactc tgtatctgca aatgaacagc ctgagacctg acgacacggc tatttattac  660
tgtgcgagag accggggacg gaaatggcta caactattgt ttgactcctg gggccagggc  720
accctggtca ccgtctcctc a                                            741

SEQ ID NO: 69          moltype = DNA  length = 747
FEATURE                Location/Qualifiers
misc_feature          1..747
                       note = Synthetic- anti-CRR9 clone 102-22 codon-optimized
                       DNA sequence
source                1..747
                       mol_type = other DNA
                       organism = synthetic construct
SEQUENCE: 69
cagtctgtgc tgacacagcc tccatctgcc tctggcacac ctggccagag agtgaccatc   60
agctgtagcg gcagcagcag caacatcggc agcaactacg tgtactggta tcagcagctg  120
cccggcacag cccctaaact gctgatctac cggaacaacc agcggcctag cggcgtgcca  180
gatagatttt ctggcagcaa gagcggcacc tctgccagcc tggctatctc tggactgaga  240
agcgaggacg aggccgacta ctattgtgcc gctgggatg atagcctgag cggcccttgg  300
gttttcggcg gaggcacaaa agtgacagtg ctcggaacgg aggatctgg tggcggaggt  360
agtggcggtg gttctggcgg aggcggttct gaagttcagc tggtggaaag tggcggcgga  420
gtcgttagac ctggcggatc tctgagactg tcttgcgccg ccagcggctt caccttcgat  480
gattacggca tgagctgggt ccgacaggcc cctggaaaag gccttgaatg ggtgtccggc  540
atcaactgga atggcggctc tacaggctac gccgactctg tgaagggcag attcaccatc  600
agccgggaca cgccaagaa cagcctgtac ctgcagatga actccctgag agccgaggac  660
accgccgtgt actactgtgc atctctgaca ggcggctacc acggcatgga tgtttgggga  720
cagggcaccc tggtcaccgt ttcttct                                      747

SEQ ID NO: 70          moltype = DNA  length = 750
FEATURE                Location/Qualifiers
misc_feature          1..750
                       note = Synthetic- anti-CRR9 clone 102-27 codon-optimized
                       DNA sequence
source                1..750
                       mol_type = other DNA
                       organism = synthetic construct
SEQUENCE: 70
cagaccgtgg tcacacaaga gcctagcctg acagtgtctc ctggcggcac agtgacactg   60
acatgtgcct cttctactgg cgccgtgacc agcggctact ccccaattg gttccagcag  120
aagcctggac aggcccctag ggctctgatc tacagcacca gcaacagaca ccctggaca  180
cccgccagat tttctggctc tctgctcgga ggaaaggccg ctctgacact gtctggtgtc  240
cagcctgagg acgaggccga ttactactgc ctgatctact ctggcggcgt gtacgtgttc  300
ggcaccggca caaaactgac agtgcttggc ggcgaggat ctggcggagg tggaagcgga  360
ggcggtagtg tggtggcgg atctgaagtg cagctggtgg aatctggcgc cgaagtgaag  420
```

```
aaacctggca gcagcgtgaa ggtgtcctgc aaagctagcg gcggcacctt cagcatctac   480
gccacaaact gggtccgaca ggctccagga caaggccctg aatggatggg cggcatcatc   540
cccatgatcg acaccaccaa ctacgcccag aagttccggg gcagactgac cgtgacagcc   600
gacaagtcta cccggaccgc ctacatggaa ctgatcaacc tgaccagcga cgacaccgcc   660
gtgtactatt gtgctggcga ccccagaaga tacggcgact acgagtactt cgagttctgg   720
ggccagggca ccctggtcac agtttcttct                                    750

SEQ ID NO: 71          moltype = AA  length = 369
FEATURE                Location/Qualifiers
source                 1..369
                       mol_type = protein
                       organism = Homo sapiens
SEQUENCE: 71
MVPKPEEINL LTGESDTQQI EAEKKPTSAL DEPVSHWRPR LALNVMADNF VFDGSSLPAD   60
VHRYMKMIQL GKTVHYLPIL FIDQLSNRVK DLMVINRSTT ELPLTVSYDK VSLGRLRFWI   120
HMQDAVYSLQ QFGFSEKDAD EVKGIFVDTN LYFLALTFFV AAFHLLFDFL AFKNDISFWK   180
KKKSMIGMST KLWKVKKALK MTIFWRGLMP EFQFGTYSES ERKTEEYDTQ AMKYLSYLLY   240
PLCVGGAVYS LLNIKYKSWY SWLINSFVNG VYAFGFLFML PQLFVNYKLK SVAHLPWKAF   300
TYKAFNTFID DVFAFIITMP TSHRLACFRD DVVFLVYLYQ RWLYPVDKRR VNEFGESYEE   360
KATRAPHTD                                                           369
```

I claim:

1. A method for treating a tumor in a subject in need thereof, the method comprising: administering an effective amount of an antibody or antigen binding fragment thereof, to the subject, wherein the antibody comprises (a) a heavy chain variable region comprising a CDRH1 of SEQ ID NO:36, a CDRH2 of SEQ ID NO:37, and a CDRH3 of SEQ ID NO:38; and a light chain variable region comprising a CDRL1 of SEQ ID NO:39, a CDRL2 of SEQ ID NO:40, and a CDRL3 of SEQ ID NO:41;

(b) a heavy chain variable region comprising a CDRH1 of SEQ ID NO:42, a CDRH2 of SEQ ID NO:43, and a CDRH3 of SEQ ID NO:44; and a light chain variable region comprising a CDRL1 of SEQ ID NO:45, a CDRL2 of SEQ ID NO:46, and a CDRL3 of SEQ ID NO:47;

(c) a heavy chain variable region comprising a CDRH1 of SEQ ID NO:48, a CDRH2 of SEQ ID NO:49, and a CDRH3 of SEQ ID NO:50; and a light chain variable region comprising a CDRL1 of SEQ ID NO:51, a CDRL2 of SEQ ID NO:52, and a CDRL3 of SEQ ID NO:53;

(d) a heavy chain variable region comprising a CDRH1 of SEQ ID NO:54, a CDRH2 of SEQ ID NO:55, and a CDRH3 of SEQ ID NO:56; and a light chain variable region comprising a CDRL1 of SEQ ID NO:57, a CDRL2 of SEQ ID NO:58, and a CDRL3 of SEQ ID NO:59; or (e) a heavy chain variable region comprising a CDRH1 of SEQ ID NO:60, a CDRH2 of SEQ ID NO:61, and a CDRH3 of SEQ ID NO:62; and a light chain variable region comprising a CDRL1 of SEQ ID NO:63, a CDRL2 of SEQ ID NO:64, and a CDRL3 of SEQ ID NO:65.

2. The method of claim 1, wherein the antibody is a monoclonal antibody.

3. The method of claim 2, wherein the monoclonal antibody is a chimeric antibody, human antibody, humanized antibody, recombinant antibody, engineered antibody, conjugated antibody, bispecific monoclonal antibody, or fragment thereof.

4. The method of claim 1, wherein the antibody is an immunoconjugate comprising a therapeutic agent selected from a pharmacologic agent, radioisotope, and toxin; and a linker.

5. The method of claim 1, wherein the tumor is a solid tumor selected from the group consisting of glioblastoma, sarcoma, carcinoma, and lymphoma.

6. The method of claim 1, wherein the tumor is associated with a cancer or preneoplastic lesion selected from the group consisting of lung cancer, pancreatic cancer, prostate cancer, skin cancer, bladder cancer, kidney cancer, ovarian cancer, colon cancer, colorectal cancer, breast cancer, cervical cancer, brain cancer, esophageal cancer, and stomach cancer, or a precancerous lesion thereof.

7. The method of claim 6, wherein the tumor is associated with lung cancer or preneoplastic lesion thereof.

8. The method of claim 1, wherein the tumor exhibits resistance to a chemotherapeutic agent.

9. The method of claim 8, wherein the chemotherapeutic agent is selected from cisplatin, gemcitabine, carboplatin, carmustine (BCNU), methotrexate, fluorouracil (5-FU), goserelin, leuprolide, tamoxifen, docetaxel, paclitaxel, aldesleukin, interleukin-2, etoposide (VP-16), interferon α, tretinoin (ATRA), bleomycin, dactinomycin, daunorubicin, doxorubicin, mitomycin, vinblastine, and vincristine.

10. The method of claim 1, wherein the antibody is administered with a pharmaceutically acceptable carrier.

* * * * *